US006518248B1

(12) United States Patent
Yamazaki et al.

(10) Patent No.: US 6,518,248 B1
(45) Date of Patent: Feb. 11, 2003

(54) METHOD OF TREATING GASTRIC OR COLON CANCER BY ADMINISTRATION OF A SULFOQUINOVOSYLACYLGLYCEROL ESTER

(75) Inventors: Takayuki Yamazaki, Noda (JP); Fumio Sugawara, Niiza (JP); Keisuke Ohta, Abiko (JP); Kazuyoshi Masaki, Sakado (JP); Kotaro Nakayama, Yotsukaido (JP); Kengo Sakaguchi, Tsukuba (JP)

(73) Assignee: Toyo Suisan Kaisha, Ltd., Tokyo (JP)

( * ) Notice: Subject to any disclaimer, the term of this patent is extended or adjusted under 35 U.S.C. 154(b) by 0 days.

(21) Appl. No.: 09/258,617

(22) Filed: Feb. 26, 1999

(30) Foreign Application Priority Data

Sep. 4, 1998 (JP) .......................... 10-251261
Dec. 28, 1998 (JP) .......................... 10-373480

(51) Int. Cl.$^7$ .............................. A61K 31/70
(52) U.S. Cl. ..................... 514/25; 536/4.1; 536/58; 536/118; 536/124
(58) Field of Search .................. 536/4.1, 54, 118, 536/124; 514/25

(56) References Cited

FOREIGN PATENT DOCUMENTS

| JP | 03052815 | * | 3/1991 |
| JP | 03052816 | * | 3/1991 |
| JP | 03066603 | * | 3/1991 |
| JP | 03246203 | * | 11/1991 |
| JP | 7-149786 | | 6/1995 |
| JP | 11106395 | * | 4/1999 |
| WO | WO 91/02521 | | 3/1991 |
| WO | WO 97/40838 | | 11/1997 |

OTHER PUBLICATIONS

Wang et al., "Tobacco Smoking and Cancer: The Promise of Molecular Epidemiology," *Salud Publica Mex., 39*(4), 331–345 (1997); supplied copy included text only, apparently from journal internet web site, Copy supplied by applicant.*

Keisuke Ohta et al., "Sulfoquinovosyldiacylglycerol, KM043, a New Potent Inhibitor of Eukaryotic DNA Polymerases and HIV–Reverse Transcriptase Type 1 from a Marine Red Alga, *Gigartina tenella*", *Chem. Pharm. Bull., 46*(4), 684–696 (1998). (Apr., 1998).

Yoshiyuki Mizushina et al., "Studies on Inhibitors of Mammalian DNA Polymerase α and β", *Biochemical Pharmacology, 55*, 537–541 (1998).

H. Sahara et al., "In vivo anti–tumour effect of 3'–sulphonoquinovosyl 1'–monoacylglyceride isolated form sea urchin (Strongylocentrotus intermedius) intestine", *British Journal of Cancer, 75*(3), 324–332 (1997).

Dana M. Gordon et al., "Synthesis of a Cyanobacterial Sulfolipid: Confirmation if Its Structure, Sterochemistry, and Anti–HIV–1 Activity", *J. Amer. Chem. Soc., 114*, 659–663 (1992). (Issue No. 2).

Roy Gigg et al, "Synthesis of 3–0–(6–Deoxy–6–sulpho–α–D–glucopranosyl)–1,2–di–O–hexadecanoyl–L–glycerol, 'Sulphoquinovosyl Diglyceride'" *Journal of the Chemical Society Perkin Transaction I*, 2490–2493 (1980).

Hideaki Shirahashi et al., "Isolation and Identification of Anti–tumor–Promoting Principles from the Fresh–Water Cyanobacterium *Phormidium tenue*", *Chem. Pharm. Bull., 41*(9), 1664–1666 (1993). (Sep., 1993).

*Pharm Quang Lien et al., "Structures, teneurs et compositions des esters sulfuriques, sulfoniques, phosphoriques des glycosyldiglycerides de trois fucasees", *Biochimie, 58*, 1367–1380 (1976).

Michael Keusgen et al., "Sulfoquinovosyl Diacylglycerols form the Alga *Heterosigma carterae*", *Lipids*, 1101–1112, 32, (1997). (Issue No. 10).

Byeng Wha Son, "Glycolipids from Gracilaria Verrucosa", *Phytochemistry, 29*, 307–309 (1990). (Issue No. 1).

Luca Rastrelli, "Glycolipids from Byrsonima Crassifolia", *Phytochemistry, 45*, 647–650 (1997). (Issue No. 4).

Tulloch et al., "Combination and Positional Distribution of Fatty Acids in Plant Sulfolipids," *Hoppe–Seyler's Zeitschrift Physiol. Chem., 354*, 879–889 (Aug., 1973).*

Fusetani et al., "Structures of Two Water Soluble Hemolysins Isolated form the Green Alga *Ulva pertusa,*" *Agricultural and Biological Chemistry,39*(10), 2021–2025 (Oct., 1975).*

Kitagawa et al., "Sulfoglycolipid from the Sea Urchin *Anthocidaris vrassisspina* A. Agassiz," *Chemical & Pharmaceutical Bulletin, 27*(8), 1934–1937 (Aug., 1979).*

(List continued on next page.)

*Primary Examiner*—Ralph Gitomer
*Assistant Examiner*—L. Eric Crane
(74) *Attorney, Agent, or Firm*—Frishauf, Holtz, Goodman, Langer & Chick, P.C.

(57) ABSTRACT

An anticancer drug includes a compound represented by Formula (1):

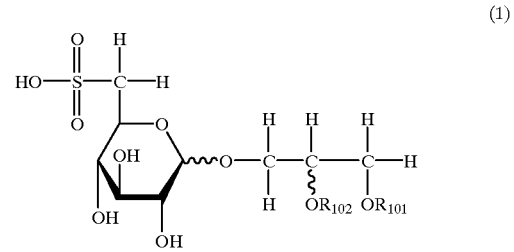

where $R_{101}$ represents an acyl moiety of a saturated higher fatty acid, and $R_{102}$ represents a hydrogen atom or an acyl moiety of a saturated higher fatty acid, and/or a pharmaceutically acceptable salt thereof.

13 Claims, 28 Drawing Sheets

OTHER PUBLICATIONS

Gustafson et al., "AIDS–Antiviral Sulfolipids From Cyanobacteria (Blue–Green Algae)," *Journal of the National Cancer Institute(USA)*, 81(16), 1255–1258 (Aug. 16, 1989).*

Adebodun et al., "Spectroscopic Studies of Lipids and Biological Membranes: Carbon–13 and Proton Magic–Angle Sample–Spinning Nuclear Magnetic Resonance Study of Glycolipid–Water Systems," *Biochemistry*, 31(18), 4502–4509 (May, 1992).*

Gage et al., "Commparison of Sulfoquinovosyl Diacylglycerol from Spinach and the Purple Bacterium *Rhodobacter sphaeroides* by Fast Atom Bombardment Tandem Mass Spectrometry," *Lipids*, 27(8), 632–636 (Aug., 1992).*

Morimoto et al., "Studies on Glycolipids. VII. Isolation of Two New Sulfoquinovosyl Diacylglycerols form the Green Alga *Chlorella vulgaris*," *Chemical & Pharmaceutical Bulletin*, 41(9), 1545–1548 (Sep., 1993).*

Amarquaye et al., "A New Glycolipid form *Byrsonima crassifolia*," *Planta Medica*, 60(1), 85–86 (Feb., 1994).*

Murakami et al., "Enzymatic Transformation of Glyceroglycolipids into sn–1 and sn–2 Lysoglyceroglycolipids by Use of *Rhizopus arrhizus* Lipase," *Tetrahedron*, 50(7), 1993–2002 (Feb. 14, 1994).*

Vishwanath et al., "Interaction of Plant Lipids with 14 kDa Phospholipase $A_2$ Enzymes," *Biochemical Journal*, 320(1), 93–99 (Nov. 15, 1996).*

Golik et al., "Isolation and Structure Determination of Sulfonoquinovosyl Dipalmitoyl Glyceride, a P–Selectin Receptor Inhibitor from the Alga *Dictyochloris fragrans*," *Journal of Natural Products*, 60(4), 387–389 (Apr., 1997).*

Vaspänge et al., "A Sulfonoglycolipids form the Fern *Polypodium decumanum* and its Effect on the Platelet Activating–factor Receptor in Human Neutrophils," *Journal of Pharmaceutical Pharmacology*, 49(5), 562–566 (May, 1997).*

Kim et al., "Structural Identification of Glycerolipid Molecular Species Isolated from Cyanobacterium *Synechocytis* sp. PCC 6803 Using Fast Atom Bombardment Tandem Mass Spectrometry," *Analytical Biochemistry*, 267, 260–270 (1990).*

* cited by examiner

METHOD OF TREATING GASTRIC OR COLON CANCER BY ADMINISTRATION OF A SULFOQUINOVOSYLACYLGLYCEROL ESTER

BACKGROUND OF THE INVENTION

The present invention relates to an anticancer drug, and in particular to an anticancer drug comprising, as an effective ingredient, a certain sulfoquinovosylacylglycerol derivative and/or a salt thereof.

Among the sulfoquinovosylacylglycerol derivatives that are the effective ingredients of the anticancer drug of the present invention, the β-anomers of sulfoquinovosylacylglycerol derivatives are novel compounds. Thus, the present invention also relates to these novel β-anomers of sulfoquinovosylacylglycerol derivatives.

Further, the present invention relates to a novel pyranoside that is useful as an intermediate for producing sulfopyranosylacylglycerol derivatives including the sulfoquinovosylacylglycerol derivatives of the present invention, and a process for producing the same.

Sulfoquinovosylacylglycerol derivatives have, as a basic skeleton, 6-deoxy-6-sulfo-D-glycopyranosylglycerol wherein the hydroxyl group bonded to carbon at the 6-position of D-glucose (carbon at the n-position of a sugar is sometimes referred to as "C-n" hereinafter) is substituted by a sulfo group and glycerol is introduced to the hydroxyl group bonded to the C-1. Either one or both of two hydroxyl groups in the glycerol moiety form ester bonds with a fatty acid or acids. As the sulfoquinovosylacylglycerol derivatives, there are various derivatives in accordance with sorts of the fatty acid ester-bonded to the glycerol. Among these sulfoquinovosylacylglycerol derivatives, some derivatives are known to exhibit physiological activity which may be applied to medicinal drugs.

For example, in Chemical & Pharmaceutical Bulletin, 46(4), (1998), Ohta et al. report that a certain sulfoquinovosylacylglycerol derivative obtained from marine red alga, Gigartina tenella exhibits inhibitory activity against eukaryotic DNA polymerases α and β, and inhibitory activity against HIV-reverse transcriptase.

In Biochemical Pharmacology, 55, 537–541 (1998), Mizushina et al. describe that a certain sulfoquinovosylacylglycerol derivative obtained from a pteridophyte exhibits inhibitory activity against calf DNA polymerase α and rat DNA polymerase β, but does not have any influence on the inhibitory activity against HIV-reverse transcriptase.

On the other hand, in British Journal of Cancer, 75 (3), 324–332 (1997), Sahara et al. state that a sulfoquinovosylacylglycerol fraction contained in a solvent extract of sea urchin intestines exhibits an anticancer effect in vivo and in vitro. However, the sulfoquinovosylacylglycerol fraction whose anticancer effect was found by Sahara et al. is in a from of mixture which mainly contains monoacylglycerol wherein its fatty acid acyl moiety is an acyl moiety of a $C_{16}$ saturated fatty acid, but also contains monoacylglycerol wherein its acyl moiety is an acyl moiety of other fatty acid as well as monoacylglycerol wherein its acyl moiety is an acyl moiety of an unsaturated fatty acid. Thus, an independent effect of each of the derivatives is not made clear. Additionally, Sahara et al. state in the same literature that a fraction containing a mixture of sulfoquinovosyldiacylglycerol derivatives contained in the solvent extract of sea urchin intestines did not exhibit any anticancer effect.

Usually, sulfoquinovosylacylglycerol derivatives are extracted from natural products such as algae and higher plants. In many cases, however, the sulfoquinovosylacylglycerol derivatives extracted from natural products are mixtures of acylglycerols wherein acyl moieties of fatty acids constituting glyceride moieties are different. Therefore, in order to obtain a single sulfoquinovosylacylglycerol derivative, a further purification is required. Moreover, according to such an extraction method from a natural product, it is difficult to obtain natural raw materials quantitatively and qualitatively stably.

Jpn. Pat. Appln. KOKAI Publication No. 7-149786 discloses a glyceroglycolipid as a carcinogenesis promoter inhibiting agent, and a process for synthesizing the same. However, the glyceroglycolipid disclosed in this publication is a compound wherein all the hydroxyl groups of galactose constituting the sugar moiety of the glyceroglycolipid are either protected by protecting groups such as benzyl groups, or non-substituted. In other words, the glyceroglycolipid disclosed in this publication is not any sulfopyranoside having a sulfo group at the C-6. According to the synthesizing process disclosed in this publication, basically glycerol is directly bonded to galactose. In this synthesizing process, many steps are necessary for protection or de-protection of not only the hydroxyl groups of the galactose, but also of the hydroxyl groups of the glycerol. For example, two hydroxyl groups of the glycerol are protected before they are bonded to the C-1 of the galactose, and after the bonding, the hydroxyl groups are de-protected. Then, they are again protected for reaction for the galactose. After the reaction, they are de-protected and then fatty acids are introduced thereto.

Furthermore, Dona M, Gordon and Samuel J, Danishefsky have reported a process for producing sulfoquinovosylacylglyceride by reacting glucal with isopropylideneglycerol (J. Am. Chem. Soc., 1992, 114, 659–663). However, glucal, which is used as the starting material in this synthesizing process, is very expensive.

BRIEF SUMMARY OF THE INVENTION

Accordingly, an object of the present invention is to provide a novel anticancer drug comprising, as an effective ingredient, a certain sulfoquinovosylacylglyceride.

Another object of the present invention is to provide a compound which can be used as an intermediate useful for industrially synthesizing sulfopyranosylacylglycerol derivatives such as sulfoquinovosylacylglycerol derivatives, in large quantities and high yields at low costs by fewer steps, as well as a process for producing the same.

The present inventors have now found that a compound represented by the following Formula (1):

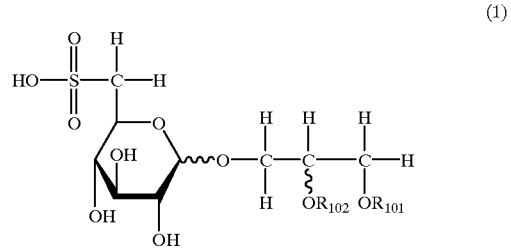

(1)

where $R_{101}$ represents an acyl moiety of a saturated higher fatty acid, and $R_{102}$ represents a hydrogen atom or an acyl moiety of a saturated higher fatty acid, or a pharmaceutically acceptable salt thereof exhibits an anticancer effect, even in a single form.

Furthermore, the present inventors have found that sulfoquinovosylacylglycerol derivatives can be effectively produced in fewer steps than steps for protecting/de-protecting many hydroxyl groups in the glycerol moiety, as are needed in the process of synthesizing glyceroglycolipid disclosed in Jpn. Pat. Appln. KOKAI Publication No. 7-149786, by using, as an intermediate, a pyranose derivative having 2-propenyloxyl group substituted at the C-1 and having an alkyl- or arylsulfonyloxy group, or a substituted carbonylthio group substituted at C-6.

Thus, the present invention provides an anticancer drug comprising, as an active ingredient, at least one compound selected from the group consisting of the compounds represented by the above-mentioned Formula (1) and the pharmaceutically acceptable salts thereof.

Among the compounds represented by Formula (1), compounds wherein the bond between the C-1 of the glucose and the glycerol is a β-bond are new compounds. These new β-anomers of the sulfoquinovosylacylglycerol derivatives (which may be referred to as "β-derivatives" hereinafter) are represented by the following Formula (2):

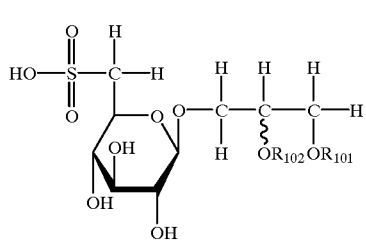

(2)

where $R_{101}$ and $R_{102}$ are as defined in Formula (1).

The present invention also provides, as an intermediate useful for production of sulfopyranosylacylglycerol derivatives such as sulfoquinovosylacylglycerol derivatives, a 1-O-(2-propenyl)-6-O-sulfonylpyranoside represented by the following Formula (A):

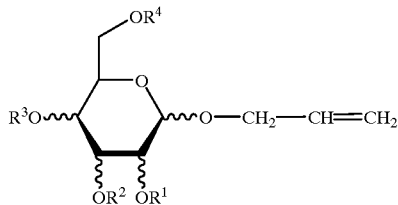

(A)

where $R^1$, $R^2$ and $R^3$ each independently represents an alkyl or substituted silyl group, and $R^4$ represents an alkylsulfonyl or arylsulfonyl group, as well as a 1-O-(2-propenyl)-6-deoxy-6-carbonylthiopyranoside represented by the following Formula (B):

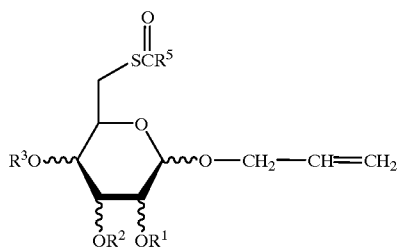

(B)

wherein $R^1$, $R^2$ and $R^3$ each independently represents an alkyl or substituted silyl group, and $R^5$ represents a hydrogen atom, or an alkyl or aryl group.

The pyranoside represented by Formula (B) according to the present invention can be produced by substituting the alkyl- or arylsulfonyloxy group (—$OR^4$) bonded to the C-6 of the pyranoside represented by Formula (A) with a substituted carbonylthio group (—SC(=O)$R^5$).

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a $^1$H NMR chart of 2,3,4-tri-O-benzyl-1-O-(2-propenyl)-6-O-(4-tolylsulfonyl)-α-D-glucose, which was produced in Example 1 which will be described later;

FIG. 2 is a $^{13}$C NMR chart of 2,3,4-tri-O-benzyl-1-O-(2-propenyl)-6-O-(4-tolylsulfonyl)-α-D-glucose, which was produced in Example 1 which will be described later;

FIG. 4 is a $^{13}$C NMR chart of 2,3,4-tri-O-(t-butyldimethylsilyl)-1-O-(2-propenyl)-6-O-(4-tolylsulfonyl)-α-D-glucose, which was produced in Example 2 which will be described later;

FIG. 5 is a $^1$H NMR chart of 2,3,4-tri-O-benzyl-1-O-(2-propenyl)-6-O-(4-tolylsulfonyl)-α-D-mannose, which was produced in Example 3 which will be described later;

FIG. 6 is a $^{13}$C NMR chart of 2,3,4-tri-O-benzyl-1-O-(2-propenyl)-6-O-(4-tolylsulfonyl)-α-D-mannose, which was produced in Example 3 which will be described later;

FIG. 8 is a ¹³C NMR chart of 2,3,4-tri-O-benzyl-6-deoxy-1-O-(2-propenyl)-6-acetylthio-α-D-glucose, which was produced in Example 4 which will be described later;

FIG. 9 is a ¹H NMR chart of 2,3,4-tri-O-(t-butyldimethylsilyl)-6-deoxy-1-O-(2-propenyl)-6-acetylthio-α-D-glucose, which was produced in Example 5 which will be described later;

FIG. 10 is a ¹³C NMR chart of 2,3,4-tri-O-(t-butyldimethylsilyl)-6-deoxy-1-O-(2-propenyl)-6-acetylthio-α-D-glucose, which was produced in Example 5 which will be described later;

FIG. 11 is a ¹H NMR chart of 2,3,4-tri-O-benzyl-6-deoxy-1-O-(2-propenyl)-6-acetylthio-α-D-mannose, which was produced in Example 6 which will be described later;

FIG. 12 is a ¹³C NMR chart of 2,3,4-tri-O-benzyl-6-deoxy-1-O-(2-propenyl)-6-acetylthio-α-D-mannose, which was produced in Example 6 which will be described later;

FIG. 13 is a ¹H NMR chart of a sodium salt of 3-O-(6-deoxy-6-sulfo-β-D-glucopyranosyl)-1-O-palmitoylglycerol, which was produced in Example 9 which will be described later; and FIG. 14 is a ¹³C NMR chart of a sodium salt of 3-O-(6-deoxy-6-sulfo-β-D-glucopyranosyl)-1-O-palmitoylglycerol, which was produced in Example 9 which will be described later.

DETAILED DESCRIPTION OF THE INVENTION

Figure 1A:
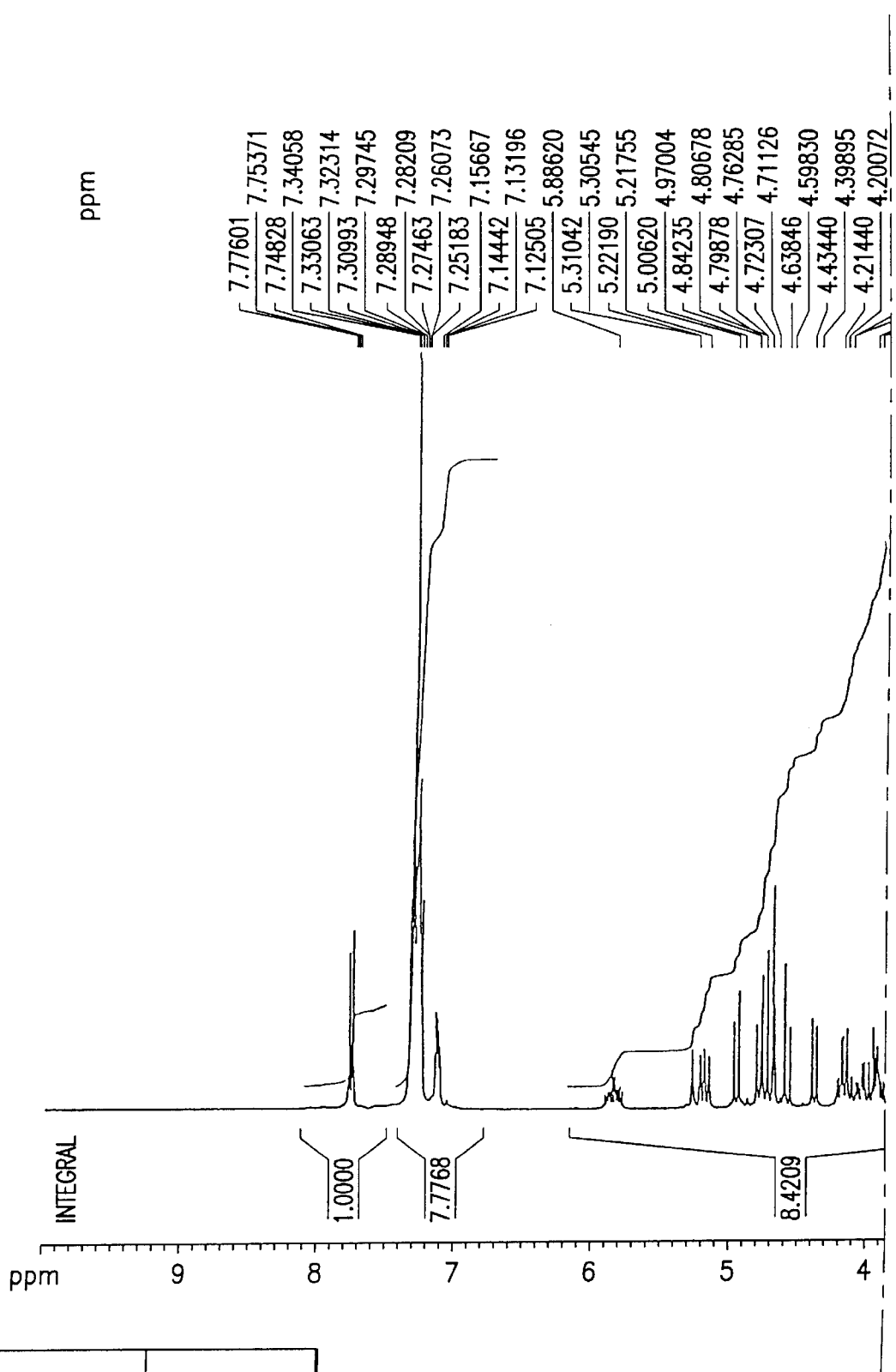
FIGS. 1A and 1B comprise a $^1$H NMR chart of 2,3,4-tri-O-benzyl-1-O-(2-propenyl)-6-O-(4-tolylsulfonyl)-α-D-glucose, which was produced in Example 1, which is described hereinbelow.

First, the anticancer drug of the present invention will be described in detail.

As described above, the anticancer drug of the present invention comprises, as an effective ingredient, at least one compound selected from the group consisting of sulfoquinovosylacylglycerol derivatives represented by the following Formula (1), and/or pharmaceutically acceptable salts thereof:

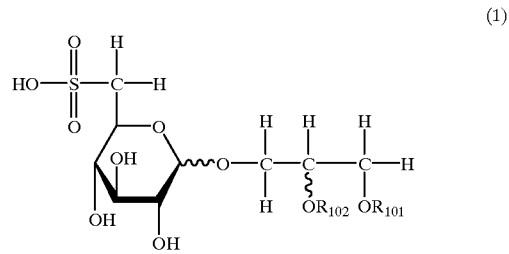

(1)

The glycerol structure may take a boat or chair conformation. Further, the absolute configuration at the carbon of the 2-position of the glycerol moiety of the compound of Formula (1) (asymmetric carbon) may be the S- or R-configuration. As the effective ingredient, a mixture of S-form and R-form may be used.

Preferably, the anticancer drug of the present invention contains only the glycerol derivative or derivatives represented by Formula (1) or a salt thereof, as a sulfoquinovosylacylglycerol derivative or a salt thereof.

In Formula (1), $R_{101}$ represents an acyl moiety of a saturated higher fatty acid. Fatty acids which can provide the acyl moiety of the saturated higher fatty acid represented by $R_{101}$ include straight chain or branched, saturated higher fatty acids. From the viewpoint of an anticancer effect against, especially, colon cancer or gastric cancer, $R_{101}$ is preferably an acyl moiety of a straight chain saturated higher fatty acid, and more preferably is a group represented by $CH_3(CH_2)_nCO-$ where n is an integer of 12–24, and preferably n is an even number of 12–24. This acyl moiety can be represented by RCO— where R is a non-substituted straight chain alkyl group having 13–25 carbon atoms, and is preferably a non-substituted straight chain alkyl group having carbon atoms in an odd number of 13–25.

In Formula (1), $R_{102}$ represents a hydrogen atom or an acyl moiety of a saturated higher fatty acid. Fatty acids which can provide the acyl moiety of the saturated higher fatty acid include straight chain or branched, saturated higher fatty acids. The saturated higher fatty acid represented by $R_{102}$ is usually the same as the saturated higher fatty acid described about $R_{101}$. Thus, the acyl moiety, $R_{102}$, can also be represented by RCO— as described above. From the viewpoint of particularly an anticancer effect against colon cancer or gastric cancer, $R_{101}$ is preferably a hydrogen atom. Exceptionally, however, in the case where $R_{101}$ is $CH_3(CH_2)_{12}CO-$, even if $R_{102}$ is $CH_3(CH_2)_{12}CO-$, the resultant compound or a salt there of exhibits a preferable anticancer effect as the compound wherein $R_{102}$ is a hydrogen atom.

In the anticancer drug of the present invention, the bond between the sulfo-substituted glucose and the glyceride in the compound represented by Formula (1) may be an α- or β-bond. From the viewpoint of particularly an anticancer effect against colon cancer or gastric cancer, the α-bond is preferred.

Among the compounds represented by Formula (1) which are used in the anticancer drug of the present invention, compounds preferred from the viewpoint of particularly an anticancer effect against colon cancer or gastric cancer are listed in the following Table 1.

TABLE 1

[Structure of Formula (1): sulfo-substituted glucopyranose linked via O to glyceride with $OR_{101}$ and $OR_{102}$ groups]

(1)

| Compound | $R_{101}-$ | $R_{102}-$ | Bond between the C-1 of the glucose and the glyceride |
|---|---|---|---|
| SQAG 1 | $CH_3(CH_2)_{12}CO-$ | $CH_3(CH_2)_{12}CO-$ | α |
| SQAG 2 | $CH_3(CH_2)_{12}CO-$ | H | α |
| SQAG 3 | $CH_3(CH_2)_{14}CO-$ | $CH_3(CH_2)_{14}CO-$ | α |
| SQAG 4 | $CH_3(CH_2)_{14}CO-$ | H | α |
| SQAG 5 | $CH_3(CH_2)_{16}CO-$ | $CH_3(CH_2)_{16}CO-$ | α |
| SQAG 6 | $CH_3(CH_2)_{16}CO-$ | H | α |
| SQAG 7 | $CH_3(CH_2)_{14}CO-$ | $CH_3(CH_2)_{14}CO-$ | β |
| SQAG 8 | $CH_3(CH_2)_{14}CO-$ | H | β |
| SQAG 9 | $CH_3(CH_2)_{16}CO-$ | $CH_3(CH_2)_{16}CO-$ | β |
| SQAG 10 | $CH_3(CH_2)_{16}CO-$ | H | β |
| SQAG 11 | $CH_3(CH_2)_{18}CO-$ | H | α |
| SQAG 12 | $CH_3(CH_2)_{20}CO-$ | H | α |
| SQAG 13 | $CH_3(CH_2)_{22}CO-$ | H | α |
| SQAG 14 | $CH_3(CH_2)_{24}CO-$ | H | α |

Among the above-mentioned compounds SQAG 1–SQAG 14, the compounds SQAG 1, SQAG 2, SQAG 4, SQAG 6, SQAG 8, SQAG 11, SQAG 12, SQAG 13 and SQAG 14 are especially preferred from the viewpoint of an anticancer effect against colon cancer or gastric cancer.

The compounds represented by Formula (1) may be in the form of pharmaceutically acceptable salts. Examples of such pharmaceutically acceptable salts include salts of a monovalent cation such as a sodium or potassium ion, but the pharmaceutically acceptable salts are not limited to these salts. The compound of Formula (1) or a pharmaceutically acceptable salt thereof is sometimes referred to as "anticancer active substance", hereinafter.

The anticancer active substance of the present invention can be orally or parenterally administered. Medicinal drugs can be produced from the anticancer active substance of the present invention by combining the substance with, for example, a suitable, pharmaceutically acceptable excipient or a diluent in accordance with an administration route.

The forms of an agent suitable for oral administration include, for example, the forms of solid, semi-solid, liquid, gas states. Specific examples include tablet, capsule, powder, granule, solution, suspension, syrup, and elixir agents. However, the forms of agents are not limited to these forms.

In order to formulate the anticancer active substance of the present invention into tablets, capsules, powders, granules, solutions or suspensions, the anticancer active substance of the present invention is mixed with a binder, a disintegrating agent and/or a lubricant, and, if necessary, the resultant is mixed with a diluent, a buffer, an infiltrating agent, a preservative and/or a flavor, using a known method. Examples of the binder include crystalline cellulose, cellulose derivatives, cornstarch, and gelatin. Examples of the disintegrating agent include cornstarch, potato starch, and sodium carboxymethylcellulose. Examples of the lubricant include talc and magnesium stearate. Furthermore, additives, which have been conventionally used, such as lactose and mannitol, may also be used.

Moreover, the anticancer active substance of the present invention may be administered in the form of aerosol or inhalant prepared by charging the active substance in the form of liquid or fine powder, together with a gaseous or liquid spraying agent and if necessary a known auxiliary agent such as an inflating agent, into a non-pressurized container such as an aerosol container or a nebulizer. As the spraying agent, a pressurized gas of, for example, dichlorofluoromethane, propane or nitrogen may be used.

For parenteral administration, the anticancer drug of the invention can be administered rectally or by injection.

For the rectal administration, a suppository can be used. The suppository may be prepared by mixing the anticancer active substance of the present invention with an excipient that can be melted at body temperature but is solid at room temperature, such as cacao butter, carbon wax or polyethylene glycol and molding the resultant material, by a known method.

For the administration by injection, the anticancer drug of the invention can be injected hypodermically, intracutaneously, intravenously or intramuscularly. Medicinal drugs for such injection may be prepared by dissolving, suspending or emulsifying the anticancer active substance of the invention into an aqueous or non-aqueous solvent such as vegetable oil, glyceride of synthetic resin acid, ester of higher fatty acid, or propylene glycol by a known method, and if desired, further adding an additive such as a solubilizing agent, an osmoregulating agent, an emulsifier, a stabilizer, or a preservative, which has been conventionally used.

For Formulating the anticancer drug of the invention into suspensions, syrups or elixirs, a pharmaceutically acceptable solvent such as sterilized water for injection or normalized physiological saline solution may be used.

The anticancer active substance of the invention may be used together with a compound that has other pharmaceutically acceptable activity, to prepare a medicinal drug.

The dose of the anticancer drug of the present invention may be appropriately set or adjusted in accordance with an administration form, an administration route, a degree or stage of a target disease, and the like. For example, in case of oral administration, administration by injection, or rectal administration, a dose may be set at 1–10 mg/kg body weight/day, 1–5 mg/kg body weight/day, or 1–5 mg/kg body weight/day, respectively, of an anticancer active substance of the invention, but is not limited thereto.

Cancers for which the anticancer drug of the invention is effective include those that have a property as a malignant tumor, such as adenocarcinoma, epithelioma, sarcoma, gliomatosis, melanoma, lymphoma and leukemia of mammals including human being.

The present invention also provides pyranosides represented by the above-mentioned Formulae (A) and (B) which are useful for intermediates for efficiently preparing sulfopyranosylacylglycerol derivatives including sulfoquinovosylacylglycerol derivatives of the invention. The sulfoquinovosylacylglycerol derivatives of the invention can be prepared by using the compounds of Formula (A) wherein its pyranose is D-glucose, or the compounds of Formula (B) derived therefrom. The compounds of Formula (A) or the compounds of Formula (B) derived from them are useful for preparing not only sulfopyranosylacylglycerol derivatives having an acyl moiety of a saturated fatty acid as an acyl group, but also sulfopyranosylacylglycerol derivatives having an acyl moiety of an unsaturated fatty acid as an acyl group.

The pyranosides represented by Formula (A) will now be described below in detail.

Examples of a pyranose that is a sugar skeleton which constitutes pyranoside (1-O-(2-propenyl)-6-O-sulfonylpyranoside) represented by Formula (A) of the present invention:

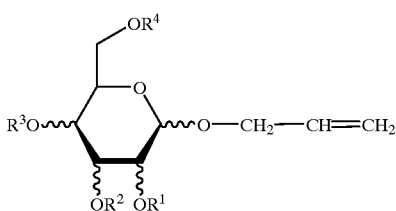

(A)

include α-D-glucose, β-D-glucose, α-D-galactose, β-D-galactose, α-D-mannose, and β-D-mannose. These sugar skeletons may be in a boat or chair conformation. From the viewpoint of stability, however, the chair form is more preferable.

In Formula (A), the bond between the C-1 and the 2-propenyl group may be an α-bond or a β-bond.

In Formula (A), $R^1$, $R^2$ and $R^3$ each in dependently represents an alkyl group or a substituted silyl group, and may be the same or different. From the viewpoint of easiness of preparation, however, these three substituents are preferably the same.

The alkyl groups represented by $R^1$, $R^2$ and $R^3$ in Formula (A) include non-substituted or substituted alkyl groups. The alkyl moiety of the non-substituted or substituted alkyl groups is preferably a lower alkyl, and more preferably an alkyl having 1–2 carbon atoms (methyl or ethyl). In the case where the alkyl group is a substituted one, examples of the substituent on the alkyl moiety include lower alkoxy groups, preferably alkoxy groups having 1–2 carbon atoms (a methoxy group or an ethoxy group), and non-substituted or substituted aryl groups. The non-substituted or substituted aryl groups preferably have 6 carbon atoms in the aryl moiety, and include a phenyl group and a p-methoxyphenyl group.

Particularly preferable alkyl groups represented by $R^1$, $R^2$ and $R^3$ include benzyl group, p-methoxybenzyl group and methoxymethyl group.

The substituents of the substituted silyl groups represented by $R^1$, $R^2$ and $R^3$ in Formula (A) include lower alkyl groups, preferably alkyl groups having 1–4 carbon atoms (for example, methyl, ethyl, isopropyl, and t-butyl groups); and aryl groups, preferably aryl groups having 6 carbons (for example, phenyl group).

The substituted silyl groups represented by $R^1$, $R^2$ and $R^3$ preferably include tri-substituted silyl groups, and more preferably include t-butyldimethylsilyl, trimethylsilyl, and triisopropylsilyl groups.

From the viewpoint of stability as protecting groups, the groups represented by $R^1$, $R^2$ and $R^3$ are preferably benzyl groups, considering that the compound represented by Formula (A) is used as an intermediate of sulfopyranosylacylglycerol derivatives having an acyl moiety of a saturated fatty acid as an acyl group. Moreover, the groups represented by $R^1$, $R^2$ and $R^3$ are preferably p-methoxybenzyl, t-butyldimethylsilyl or triethylsilyl groups, when the compound represented by Formula (A) is used as an intermediate of sulfopyranosylacylglycerol derivatives having an acyl moiety of an unsaturated fatty acid as an acyl group because these groups can easily be eliminated (deprotected) in the reaction for synthesizing such sulfopyranosylacylglycerol derivatives.

In Formula (A), $R^4$ represents an alkylsulfonyl or arylsulfonyl group.

The alkyl moiety of the alkylsulfonyl group may be non-substituted or substituted alkyl group, and is preferably a lower alkyl and more preferably an alkyl having 1–2 carbon atoms (methyl and ethyl). The alkyl moiety of the alkylsulfonyl group is preferably a non-substituted alkyl group. The alkylsulfonyl groups specifically include methanesulfonyl and ethanesulfonyl groups.

The aryl moiety of the arylsulfonyl group may be a non-substituted or substituted aryl group, and is preferably an aryl having 6 carbon atoms (that is, phenyl). In the case where the aryl group is a substituted one, examples of the substituent on the aryl moiety include p-methyl and p-methoxy groups. The arylsulfonyl groups specifically include p-toluenesulfonyl (tosyl), p-methoxybenzenesulfonyl, and benzenesulfonyl groups. Among these arylsulfonyl groups, the tosyl group is preferred from the viewpoint of stability of reaction.

Next the pyranoside represented by Formula (B) will described below in detail.

The pyranose that is a sugar skeleton which constitutes the pyranoside represented by Formula (B):

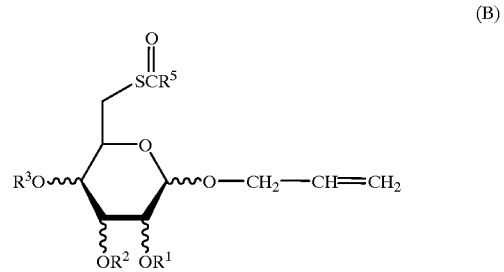

(B)

is identical to the pyranose which constitutes the pyranoside represented by Formula (A).

In Formula (B), the bond between the C-1 and the 2-propenyl group may be an α-bond or a β-bond as in the case of Formula (A).

In Formula (B), $R^1$, $R^2$ and $R^3$ are also identical to $R^1$, $R^2$ and $R^3$ in Formula (A), respectively.

In Formula (B), $R^5$ represents a hydrogen atom, or an alkyl or aryl group.

The alkyl group represented by $R^5$ include non-substituted or substituted alkyl group. The alkyl moiety thereof is preferably a lower alkyl and more preferably an alkyl group having 1–2 carbon atoms (methyl or ethyl).

The aryl groups represented by $R^5$ include a non-substituted or substituted aryl group. The aryl moiety thereof is preferably an aryl having 6 carbon atoms (that is, phenyl).

The group represented by $R^5$ is preferably methyl group from the viewpoint of stability of reaction.

There will now be described a process of preparing the compound represented by Formula (A) (steps A–E) and a process of preparing the compound represented by Formula (B)(step F), referring to the schemes illustrated below:

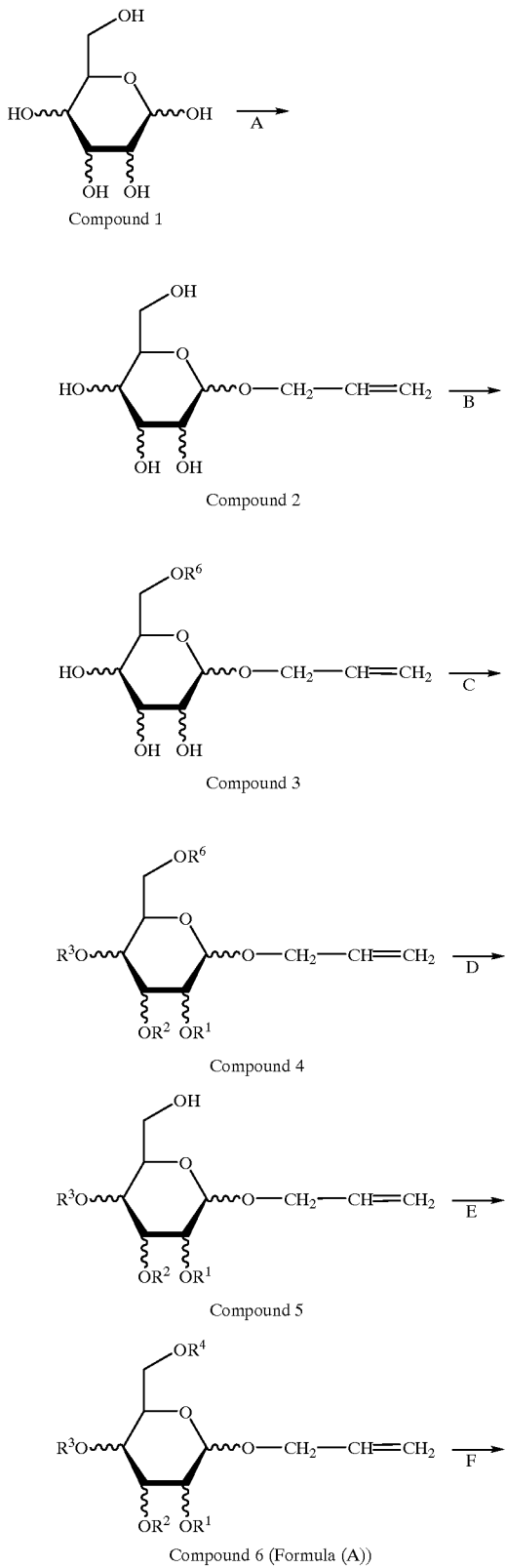

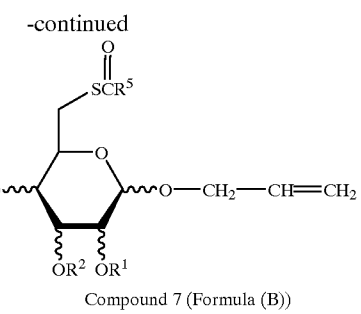

Compound 7 (Formula (B))

Step A: The hydroxyl group at the C-1 position of the non-substituted pyranose (compound 1) is subjected to 2-propenylation to give compound 2.

The 2-propenylation can be carried out by dissolving the pyranose in allyl alcohol and reacting both usually at a temperature from room temperature to 100° C., preferably from 80 to 90° C. in the presence of a strong acid such as trifluoromethanesulfonic acid. Usually, a pyranose including D-glucose is in the form of a mixture of α- and β-anomers in solution.

Step B: The hydroxyl group at the C-6 of the compound 2 is protected to be converted into —$OR^6$ where $R^6$ represents an alkyl or substituted silyl group to give compound 3.

Examples of the alkyl group represented by $R^6$ include bulky non-substituted or substituted alkyl groups. The alkyl moiety of the non-substituted or substituted alkyl group ($R^6$) is preferably an alkyl having 1–4 carbon atoms (for example, methyl or t-butyl). From the viewpoint of easiness of reaction, the alkyl group represented by $R^6$ is preferably a triaryl-substituted alkyl group, and especially preferably trityl group.

The substituent of the substituted silyl group represented by $R^6$ includes a non-substituted or substituted alkyl group, preferably, an alkyl group whose alkyl moiety is preferably a lower alkyl and more preferably an alkyl having 1–4 carbon atoms (for example, methyl, ethyl, isopropyl and t-butyl); and a non-substituted or substituted aryl group, preferably, an aryl group whose the aryl moiety has 6 carbon atoms (that is, phenyl). The substituted silyl group represented by $R^6$ is preferably a tri-substituted silyl group, and more preferably includes t-butyldiphenylsilyl group.

The protection of the hydroxyl group in the step B can be carried out by adding a hydroxyl group-protecting compound that can protect hydroxyl group, such as trityl chloride, to a solution of the compound 2 dissolved in an organic solvent such as anhydrous pyridine, and reacting the mixture in the presence of a catalyst such as dimethylaminopyridine (DMAP). The hydroxyl group-protecting compound can be represented by $R^6$—X where $R^6$ is the same as defined above, and X represents a halogen such as chlorine or bromine.

If trityl chloride is used as the hydroxyl group-protecting compound, the compound 3 is obtained wherein $R^6$ is trityl group. Trityl chloride can be preferably used from the viewpoint of preparing costs. As the hydroxyl group-protecting compound, t-butyldiphenylsilylchloride can also be used to proceed reaction at room temperature in the presence of a catalyst such as an imidazole. In this case, the compound 3 wherein $R^6$ is t-butyldiphenylsilyl group can be obtained.

Step C: The hydroxyl groups which are bonded to the C-2, the C-3 and C-4 are protected to be converted into —$OR^1$, OR² and —OR³, respectively, where R¹–R³ are as defined in Formula (A), respectively, to give compound 4.

The protection of these hydroxyl groups can be carried out by activating, by sodium hydride, the hydroxyl groups bonded to the C-2, the C-3 and the C-4 of the compound 3 dissolved in an organic solvent such as dimethylformamide (DMF), and reacting the activated compound with a hydroxyl group-protecting compound, such as benzylbromide, at room temperature. The hydroxyl group-protecting compound can be represented by R′—X where R′ is the above-mentioned R¹, R² or R³, and X is a halogen such as chlorine or bromine.

If benzyl bromide is used as the hydroxyl group-protecting compound, the compound 4 can be obtained wherein all of R¹, R² and R³ are benzyl groups. Benzylbromide can be preferably used from the viewpoint of stability of the protecting groups. As the hydroxyl group-protecting compound, there may also be used p-methoxybenzyl bromide, t-butyldimethylsilyl chloride or trimethylsilyl chloride. In this case, the compound 4 can be obtained wherein all of R¹, R² and R³ are p-methoxybenzy, t-butyldimethylsilyl or triethylsilyl groups, respectively. The reaction in the case of using such hydroxyl group-protecting compounds can be carried out under a suitable reaction condition for the respective protecting groups.

Step D: The protecting group for the hydroxyl group at the C-6 of the compound 4 is de-protected to give compound 5.

The de-protection may be carried out by reacting a solution of the compound 4 dissolved in an organic solvent such as methanol at room temperature in the presence of a catalyst such as toluenesulfonic acid.

Step E: R⁴, that is, an alkylsulfonyl or arylsulfonyl group is bonded to the hydroxyl group at the C-6 position of the compound 5, so that the hydroxyl group is converted into —OR⁴ to give a compound of Formula (A) (compound 6).

The introduction of R⁴ to the hydroxyl group at the C-6 can be carried out by adding a corresponding sulfonyl compound to a solution of the compound 5 dissolved in an organic solvent such as pyridine or dichloromethane and then reacting the resultant mixture. This reaction may be carried out at room temperature in the presence of a catalyst such as DMAP, if necessary. The sulfonyl compound can be represented by R⁴—X where R⁴ is as defined above and X is a halogen such as chlorine.

Specific examples of the alkylsufolnyl compound include methanesulfonyl chloride and ethanesufonyl chloride. If methanesulfonyl chloride or ethanesufonyl chloride is used, the compounds 6 is obtained wherein the group represented by R⁴ is methanesulfonyl or ethanesulfonyl group, respectively.

Specific examples of the arylsulfonyl compound include p-toluenesulfonyl chloride, p-methoxybenzenesulfonyl chloride and benzenesulfonyl chloride. If p-toluenesulfonyl chloride is used, the compound 6 is obtained wherein the group represented by R⁴ is p-toluenesulfonyl group (tosyl group). If p-methoxybenzenesulfonyl chloride is used, the compound 6 is obtained wherein the group represented by R⁴ is p-methoxybenzenesulfonyl group.

Among these sulfonyl compounds, the tosyl compound is preferred from the viewpoint of easiness of reaction.

The alkyl or arylsulfonyl group (R⁴) introduced in this step E can easily be eliminated, together with the oxygen atom adjacent to this group (that is, in the form of —OR⁴), from the C-6 in the substitution reaction in the next step F.

From the pyranoside of Formula (A) (the compound 6) thus obtained as above, a pyranoside of Formula (B) (compound 7) can be produced by substituting the sulfonyloxy group (—OR⁴) of the compound 6 with a substituted carbonylthio group (—SC(═O)R⁵) (step F).

Specifically, in the step F, the pyranoside of Formula (B) can be produced by reacting the pyranoside of Formula (A) in an organic solvent with a compound which is capable of substituting the alkyl- or arylsulfonyloxy group with the substituted carbonylthio group (which may be referred to as a "O→S compound" hereinafter).

Examples of the O→S compound include alkali metal or alkali earth metal salts of thiocarboxylic acid (S-acid). The thiocarboxylic acid can be represented by R⁵—C(═O)SH where R⁵ is as defined above. Examples include thioformic acid; lower thiocarboxylic acids, preferably thiocarboxylic acids having an aliphatic with 1–2 carbon atoms, for example, thioacetic acid or thiopropionic acid, as well as thiocarboxylic acids having an aromatic group with 6 carbon atoms, for example, thiobenzoic acid.

The alkali metal that forms a salt with the thiocarboxylic acid includes potassium and sodium, and the alkali earth metal includes magnesium and calcium.

Considering stability of reaction and the fact that the compound of Formula (B) is used as an intermediate for sulfopyranosylacylglycerol derivatives, salts of thioacetic acid are preferred, among the above-mentioned thiocarboxylic acids. This is because the carbonyl group can easily be eliminated in a subsequent step for producing the sulfopyranosylacylglycerol derivatives.

The addition amount of the O→S compound varies dependently on the compound used. Usually, however, the amount may be set to one to two times an amount of the compound of Formula (A) used.

Examples of an organic solvent used in the reaction include alcohol, preferably lower alcohols, for example, methanol, ethanol and propanol. The amount of the organic solvent used may be set to from an amount at which the compound of Formula (A) can be dissolved thereinto to about 2–10 times said amount.

Usually, the above-mentioned reaction may be carried out at room temperature to the boiling point of the solvent used and for 1–24 hours.

As described previously, the non-substituted pyranose, the starting material, is usually a mixture of an α-anomer and a β-anomer in solution. Therefore, the compound 6 and the compound 7 will also be obtained in a mixture of an α-anomer and a β-anomer, respectively. If necessary, the α- and β-anomers can be separated by converting the compound 2 (a mixture of α- and β-anomers thereof) into, for example, benzylidene derivatives after the step A, followed by crystallization, or subjecting the compound obtained in any one of the steps A–F to chromatography.

Sulfopyranosylacylglycerol derivatives in a salt form can be produced by using a method of subjecting the thus produced pyranoside of Formula (B) to reactions in four steps (steps G–J) as illustrated in the following schemes:

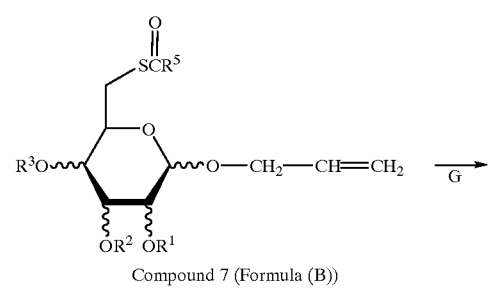

Compound 7 (Formula (B))

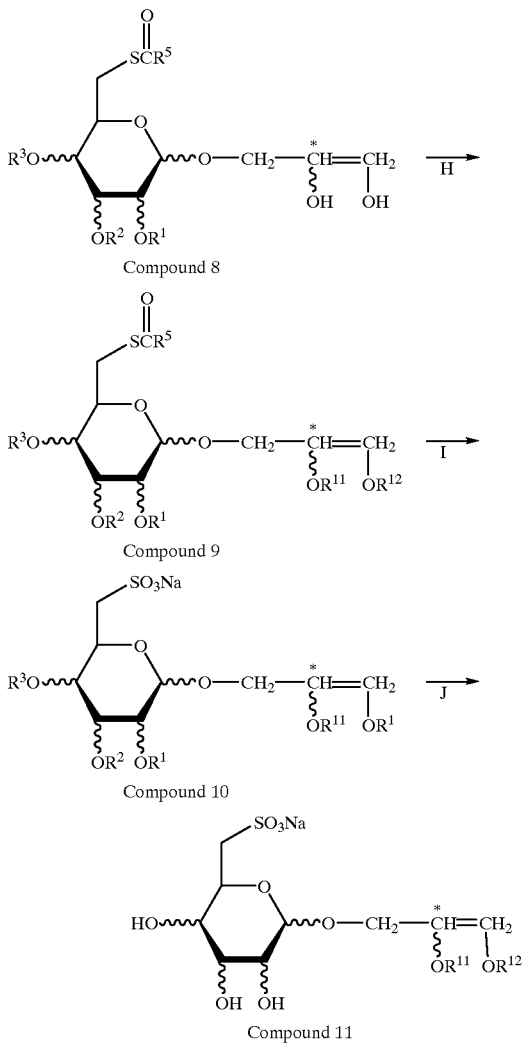

Compound 8

Compound 9

Compound 10

Compound 11

The steps G–J will be described below in detail.

First, in the step G, two hydroxyl groups are introduced to the allyl group of the compound 7 (the compound represented by Formula (B)) to give a diol compound 8.

The introduction of the two hydroxyl groups can be carried out by adding an oxidizing agent such as osmium tetraoxide to a solution of the compound 7 (the compound represented by Formula (B) dissolved in a mixed solvent such as a mixture of t-butanol and water, and then reacting the resultant mixture in the presence of a re-oxidizing agent such as trimethylamine N-oxide at room temperature. The compound 7 and the reoxidizing agent can usually be reacted in mole ratios of from 1/2 to 1/5.

Next, in the step H, at least one of the two hydroxyl groups of the compound 8 is esterified to give compound 9, wherein $R_{11}$ represents a hydrogen atom or an acyl group, and $R_{12}$ represents an acyl group.

The esterification reaction in the step H makes it possible to obtain a sulfopyranosylacylglycerol derivative, wherein a desired fatty acid is esterbonded to the glycerol. This reaction can be carried out by adding a fatty acid corresponding to a final product to a solution of the compound 5 dissolved in a suitable solvent such as dichloromethane and then reacting the resultant mixture, if necessary in the presence of a suitable catalyst such as ethyldimethylaminopropylcarbodiimide (EDCI)-DMAP system.

The reaction in the step H makes it possible to obtain a mixture of a monoester wherein $R_{11}$ is a hydrogen atom and $R_{12}$ is an acyl residue of the added fatty acid and a diester wherein both of $R_{11}$ and $R_{12}$ are acyl moieties of the added fatty acid.

As the fatty acid added, use may be made of a straight chain or branched, saturated or unsaturated fatty acid. The saturated fatty acid which can be used may be a fatty acid having an acyl group represented by $R_{101}$ in Formula (1) (that is, RCOOH wherein R is as defined above). A mixture of fatty acids may be used. Two or more fatty acids are added, it is possible to obtain a mixture of a monoester wherein $R_{11}$ is a hydrogen atom and $R_{12}$ is an acyl residue of any one of the added fatty acids and a diester wherein both of $R_{11}$ and $R_{12}$ are acyl moiety of any one of the added fatty acids.

If necessary, the mixture of the monoester and diester can be isolated into the individual esters by, for example, chromatography, and can be subjected to the next reaction in the step I.

If desired, the monoester can be reacted with a fatty acid having other acyl moiety than the acyl moiety of $R_{12}$ obtained in the step H to give a diester wherein $R_{11}$ and $R_{12}$ are different acyl residues. The reaction conditions of this further esterification may be the same as in the step H, except that the fatty acids are different.

Next, in the step I, the substituted carbonylthio group of the compound 9 is converted into a sulfonate salt to give compound 10.

The conversion into the sulfonate salt can be carried out by adding an oxidizing agent such as OXONE ($2KHSO_5$+ $KHSO_4$+$K_2SO_4$) into a solution of the compound 9 dissolved in an organic solvent, which is buffered with glacial acetic acid and potassium acetate, and then reacting the resultant mixture at room temperature.

Finally, in the step J, the protecting groups bonded at the C-2 to C-4 of the compound 10 are de-protected to give a target salt of the sulfopyranosylacylglycerol derivative (compound 11).

The de-protection of the protecting groups at the C-2 to C-4 in the step J can be carried out by reacting a solution of the compound 10 dissolved in an organic solvent such as ethanol in the presence of a catalyst such as palladium-activated carbon (Pd—C) under hydrogen gas atmosphere at room temperature.

The compound of Formula (A) wherein the groups represented by $R^1$–$R^3$ are substituted silyl groups and the group represented by $R^4$ is an alkylsulfonyl or arylsulfonyl group can also be produced through three steps (the steps K–M), as illustrated in the following scheme:

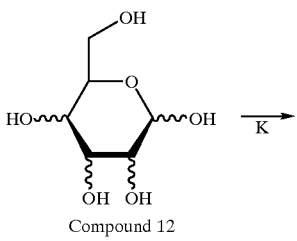

Compound 12

-continued

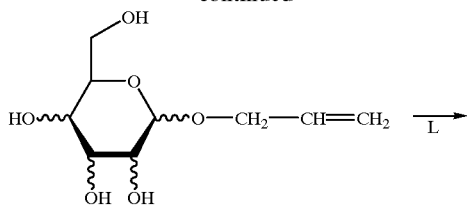

Compound 13

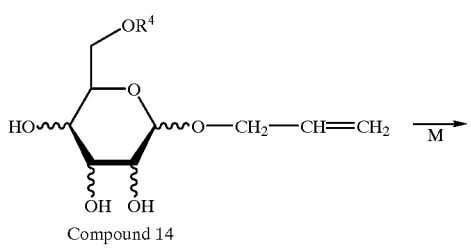

Compound 14

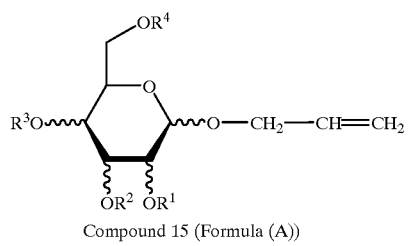

Compound 15 (Formula (A))

The steps K–M will be described below in detail.

The step K is identical to the step A described above. Thus, the compound 12 is identical to the compound 1, and the compound 13 is identical to the compound 2.

Next, in the step L, the hydroxyl group at the C-6 of the compound 13 is converted into —$OR^4$ by bonding $R^4$ (which is an alkylsulfonyl or arylsulfonyl group as described above) to this hydroxyl group. $R^4$ is preferably an arylsulfonyl group.

The step L can be carried out under the same conditions as in the step E.

Thereafter, in the step M, substituted silyl groups are introduced to the C-2 to C-4 of the compound 14. The substituted silyl group is preferably a tri-substituted silyl group, and more preferably includes t-butyldimethylsilyl, trimethylsilyl, triethylsilyl, and triisopropylsilyl. From the viewpoint of stability of a resultant product (compound 15), t-butyldimethylsilyl is especially preferred.

This reaction can be carried out by adding a hydroxyl group-protecting compound, such as t-butyldimethylsilyltrifluoromethane sulfonate to a solution of the compound 14 dissolved in an organic solvent such as anhydrous dichloromethane, and then keeping the resultant mixture at room temperature in the presence of a catalyst such as 2,6-lutidine.

From the compound of Formula (A) obtained in the step M, a corresponding compound represented by Formula (B) can be produced through the step F described above.

From the compound of Formula (B) obtained in the step F, a corresponding sulfonate salt of the sulfopyranosylacylglycerol derivative can be produced through the steps G–J described above.

Furthermore, a sulfopyranosylacylglycerol derivative can be produced by subjecting the sulfonate salt obtained in the step J to titration with an acid such as hydrochloric acid.

Needless to say, the sulfoquinovosylacylglycerol derivatives of Formula (1) can be produced by using D-glucose as the starting pyranose in the method described above.

Among the above-mentioned sulfopyranosylacylglycerol derivatives, the β-anomers represented by the following Formula (2) are novel compounds:

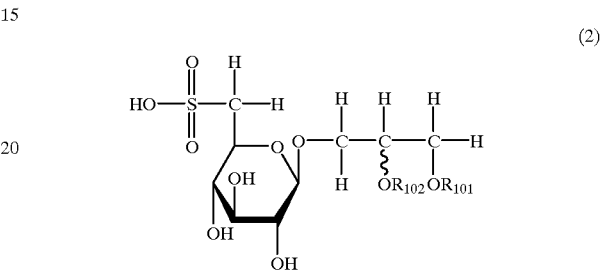

(2)

where $R_{101}$ and $R_{102}$ are as defined above. Of course, the β-derivatives are included in the compounds represented by Formula (1) above.

The sulfoquinovosylacylglycerol β-derivatives can be produced in the same manner as the sulfopyranosylacylglyserol derivatives described above, using D-glucose as the starting non-substituted pyranose. In this case, since D-glucose is usually in the form of a mixture of α- and β-anomers of D-glucose as described above, a further step for separating β-anomer is required. The separating step may be applied at a suitable stage of the method for producing the sulfopyranosylacylglyserol derivatives described above. For example, the separating step may be carried out after the step D or F. The separating method may be carried out by a known manner, for example, silica gel chromatography using a suitable solvent.

The sulfoquinovosylacylglycerol β-derivatives represented by Formula (2) can also be produced by the following method. That is, all the hydroxyl groups in the D-glucose are acetylated and then the C-1 is halogenated. This halogenated glucose is reacted with allyl alcohol. The allyl alcohol is selectively β-bonded to the glucose. The resultant β-anomer product is de-acetylated to give 1-(O)-(2-propenyl)-β-D-glucose. The acetylation, halogenation and reaction with allyl alcohol are known per se in the art. The β-derivatives represented by Formula (2) of the invention can be produced by subjecting 1-(O)-(2-propenyl)-β-D-glucose, which is a product from the above-mentioned reactions, to the steps B–J described above.

The present invention will now be described by way of its Examples. However, the present invention is not limited to these Examples.

Physiological Assay on the Compounds represented by Formula (1) According to the Present Invention In the following assays, each of the sulfoquinovosylacylglycerol derivatives used was a mixture of S- and R-configurations.

<Assay 1>

An assay on inhibitory effect against a DNA polymerase α was carried out in the following manner.

0.05 U of a DNA polymerase α isolated from the bovine thymus and purified with an antibody column was mixed with each of compounds SQAG 1 to SQAG 14 listed in Table 1 above, each of which was dissolved in DMSO. Each mixture was added with a buffer of an inorganic salt necessary for the enzymatic reaction, [$^3$H]-labeled dTTP, and a compound for reaction containing a template DNA chain, and was incubated at 37° C. for 60 minutes.

After the enzymatic reaction was stopped, the resultant product was fixed on a dedicated filter to make measurement by a liquid scintillation counter. The amount of enzymatically synthesized dTTP was calculated as a radiation dose (cpm) of [$^3$H].

The results are shown as $IC_{50}$ in Table 2 below.

TABLE 2

| Inhibition Activity against DNA Polymerase α | | | | | | | |
|---|---|---|---|---|---|---|---|
| Compound | SQAG 1 | SQAG 2 | SQAG 3 | SQAG 4 | SQAG 5 | SQAG 6 | SQAG 7 |
| $IC_{50}$ (μg/mL) | 0.80 | 4.50 | 0.40 | 3.50 | 0.30 | 2.40 | 0.30 |
| Compound | SQAG 8 | SQAG 9 | SQAG 10 | SQAG 11 | SQAG 12 | SQAG 13 | SQAG 14 |
| $IC_{50}$ (μg/mL) | 4.00 | 0.30 | 3.00 | 1.20 | 1.00 | 1.00 | 1.00 |

As is clear from Table 2, the compounds subjected to the assay exhibited different inhibitory activity levels, i.e., from low levels to high levels, against the DNA polymerase α.

Colon cancer cells and gastric cancer cells used in the following two assays are merely examples of cancer cells for which the anticancer drug of the present invention is effective. Thus, these assays are not intended to limit cancer cells for which the anticancer drug of the invention is effective.

<Assay 2>

An assay on anticancer activity against cultured colon cancer cells was carried out in the following manner.

Colon cancer cells DLD-1 were maintained and subcultured in RPMI 1640 medium (containing 10% calf serum). Each of compounds SQAG 1, SQAG 2, SQAG 4, SQAG 6, SQAG 8, SQAG 11, SQAG 12, SQAG 13 and SQAG 14 shown in Table 1 was suspended and diluted in the medium, and then was cultivated in a 96-well plate together with the cancer cells at 3×10$^3$ cells/well. After the culture has been incubated for 48 hours, the MTT assay (Mosmann, T: Journal of immunological Method, 65, 55–63 (1983)) was carried out to compare viability rates.

The results are shown as $IC_{50}$ in Table 3.

TABLE 3

| Anti-Cancer Activity against Colon Cancer Cells | | | | | | | | |
|---|---|---|---|---|---|---|---|---|
| Compound | SQAG 1 | SQAG 2 | SQAG 4 | SQAG 6 | SQAG 8 | SQAG 11 | SQAG 12 | SQAG 13 | SQAG 14 |
| $IC_{50}$ (μg/mL) | 38 | 40 | 31 | 30 | 42 | 28 | 20 | 20 | 18 |

As is clear from Table 3, all of the compounds tested have a significant anticancer activity against the colon cancer cells.

It can be considered that each of the compounds independently has an anticancer activity equal to or more than that of a mixture of the sulfoquinovosylacylglycerol derivatives disclosed by Sahara et al. (British journal of cancer, 75 (3), 324–332 (1997)) described previously.

<Assay 3>

An assay on anticancer activity against cultured gastric cancer cells was carried out in the same manner as in the assay 2 except that gastric cancer cells NUGC-3 were used instead of the colon cancer cells DLD-1.

The results are shown as $IC_{50}$ in Table 4.

TABLE 4

| Anticancer Activity against Gastric Cancer Cells | | | | | | | | |
|---|---|---|---|---|---|---|---|---|
| Compound | SQAG 1 | SQAG 2 | SQAG 4 | SQAG 6 | SQAG 8 | SQAG 11 | SQAG 12 | SQAG 13 | SQAG 14 |
| $IC_{50}$ (μg/mL) | 32 | 40 | 40 | 37.5 | 50 | 24 | 23 | 20 | 20 |

As is clear from Table 4, all of the compounds tested have a significant anticancer activity against the gastric cancer cells.

It can be considered that each of the compounds tested singly has an anticancer activity equal to or more than that of a mixture of the sulfoquinovosylacylglycerol derivatives disclosed by Sahara et al. (British journal of cancer, 75 (3), 324–332 (1997)).

SYNTHESIS EXAMPLE

The following will describe examples wherein compounds represented by Formulae (A), (B), (1), and (2) were produced.

The following scheme 1 illustrates examples of the method for producing compounds represented by Formulae (A), (B) and (1).

Scheme 1
Synthetic Route for α-Anomer

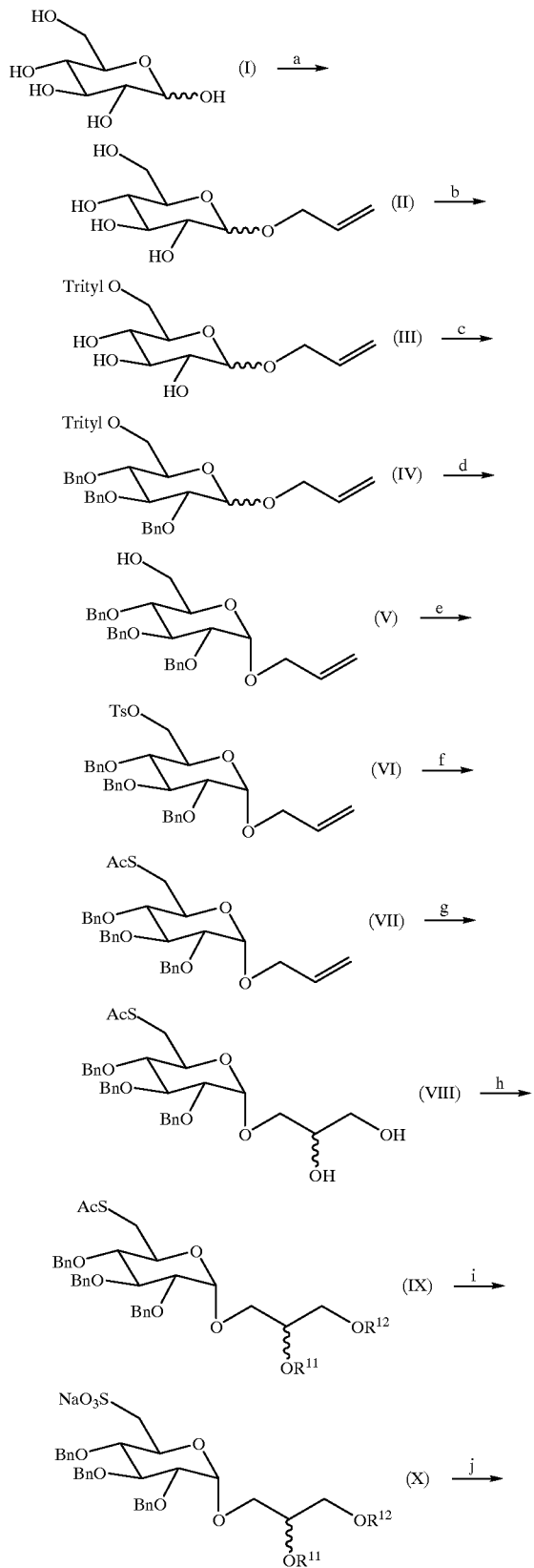

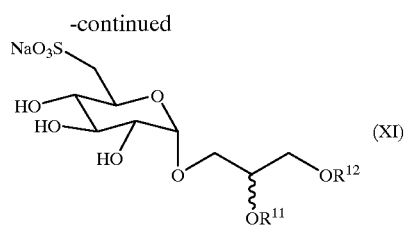

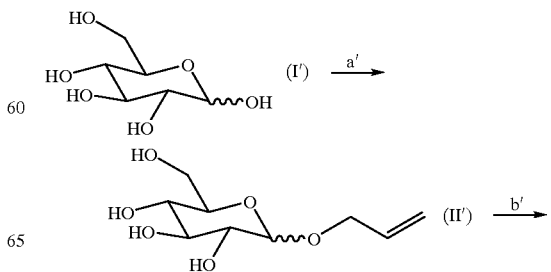

where Trityl=trityl group, Bn=benzyl group, Ts=tosyl group, AcS=acetylthio group, $R_{11}$ represents hydrogen or a saturated or unsaturated acyl group, and $R_{12}$ represents a saturated or unsaturated acyl group.

<Reaction condition>:

a: allyl alcohol; trifluoromethanesulfonic acid; 80° C.,
b: trityl chloride; dimethylaminopyridine; pyridine; room temperature
c: dimethylformamide; sodium hydride; benzyl bromide; room temperature
d: p-toluenesulfonic acid monohydrate; methanol; room temperature
e: p-toluenesulfonyl chloride; dimethylaminopyridine; pyridine; room temperature
f: potassium thioacetate; ethanol; reflux
g: osmium tetraoxide; trimethylamine N-oxide dihydrate; t-butanol; water; room temperature
h: fatty acid; EDCl, dichloromethane; dimethylaminopyridine; room temperature
i: OXONE; glacial acetic acid; potassium acetate; room temperature
j: hydrogen; palladium-activated carbon; ethanol; room temperature The above scheme 1 illustrates a synthesis route of only an α-anomer separated by silica gel flash chromatography carried out after the step d. However, in a similar manner, β-anomer of the sulfopyranosylacylglycerol derivative can also be synthesized. The mixture of the monoester and the diester obtained after the step h can be separated by chromatography, and each of the esters can be subjected to the step i.

The following scheme 2 is a suitable reaction scheme for synthesis of compounds of Formulae (A) and (B) wherein $R^1$–$R^3$ are substituted silyl groups, and of the corresponding sulfoquinovosylacylglycerol derivatives. According to the reaction illustrated in this scheme 2, through the steps b' and c' only an α-anomer can be selectively synthesized without undergoing any separating step carried out after the step d in the reaction scheme 1.

Scheme 2
Synthetic Route for α-Anomer

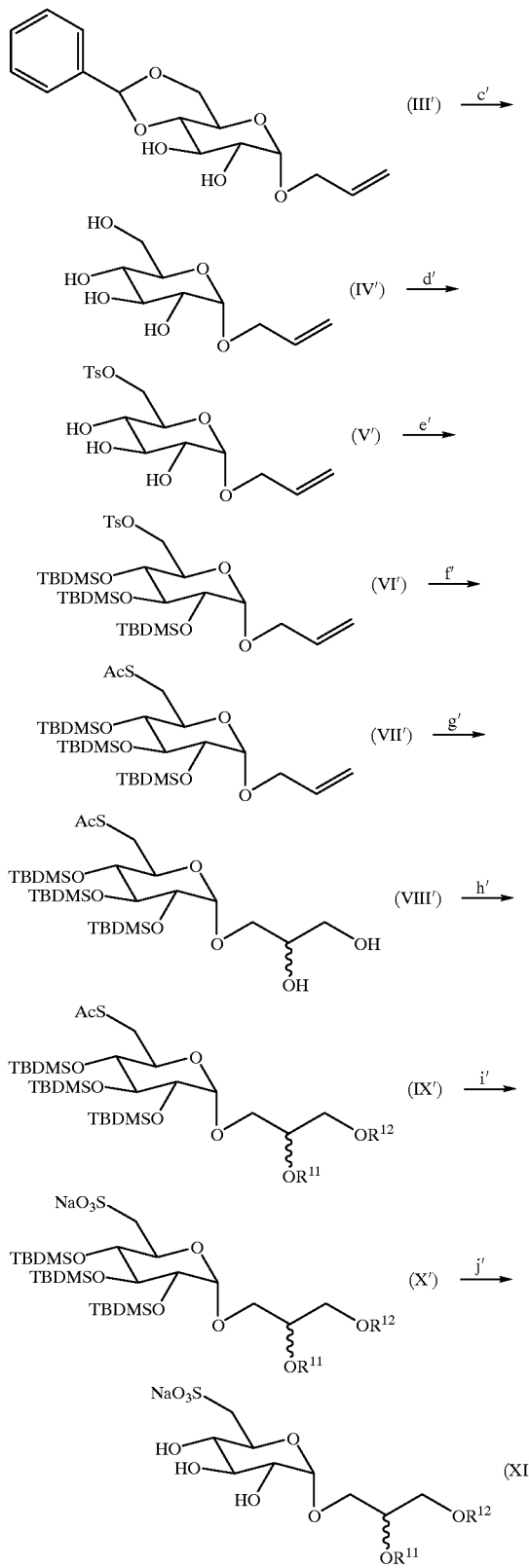

where Ts=tosyl group, TBDMS=t-butyldimethylsilyl group, AcS=acetylthio group, $R_{11}$ represents hydrogen or a saturated or unsaturated acyl residue, and $R_{12}$ represents a saturated or unsaturated acyl group.

\<Reaction condition\>:
a': allyl alcohol; trifluoromethanesulfonic acid; 80° C.
b': benzaldehyde; zinc chloride; room temperature
c': acetic acid; water; 100° C.
d': p-toluenesulfonyl chloride; dimethylaminopyridine; pyridine, room temperature
e': t-butyldimethylsilyltrifluoromethanesulfonic acid; 2,6-lutidine; dichloromethane; room temperature
f': potassium thioacetate; ethanol; reflux
g': osmium tetraoxide; trimethylamine N-oxide dihydrate; t-butanol; water; room temperature
h': fatty acid, EDCl, dichloromethane, dimethylaminopyridine, room temperature
i': OXONE; glacial acetic acid; potassium acetate; room temperature
j': acetic acid; tetrahydrofuran; trifluoroacetic acid; water; room temperature Example 1

Synthesis (1) of compounds represented by Formula (A)

Starting from D-glucose, 2,3,4-tri-O-benzyl-1-O-(2-propenyl)-6-O-(4-tolylsulfonyl)-α-D-glucose (VI) was prepared as follows.

1-1) Step a: Synthesis of 1-O-(2-propenyl)-D-glucose (II)

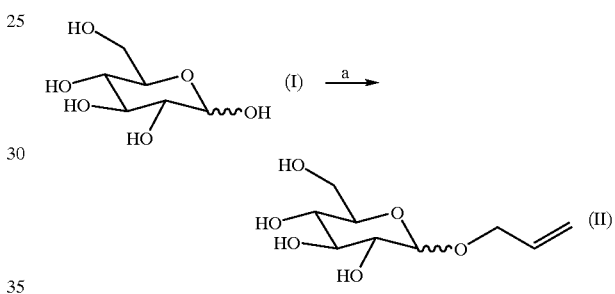

One hundred grams of D-glucose (I) were added into 250 mL of allyl alcohol and sufficiently dissolved therein. To the solution, 0.8 mL of trifluoromethanesulfonic acid were slowly added under an ice-cooled condition. Then, the solution was reacted in an oil bath at 80° C. for 30 hours, while stirring. Then the reaction mixture was neutralized with 1 mL of triethylamine, and was concentrated in vacuo to give the title compound. Thin layer chromatography demonstrated a yield of about 60–70%.

1-2) Step b: Synthesis of 1-O-(2-propenyl)-6-O-triphenylmethyl-D-glucose (III).

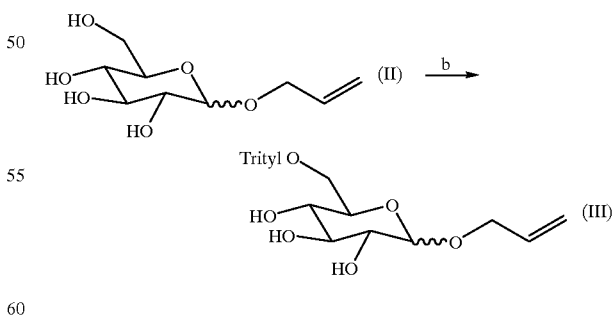

One hundred grams (455 mmol) of 1-O-(2-propenyl)-D-glucose (II) were dissolved in 350 mL of anhydrous pyridine, and the solution was added with 170 g (610 mmol) of tritylchloride and 1.0 g (8.20 mmol) of DMAP. The reaction mixture was reacted for 36 hours at room temperature, while stirring. Then, the reaction was quenched by addition of 800 mL of cold distilled water, and then extracted with ethyl acetate (500 mL×3 times). The organic layers were combined, acidified to pH 4 by diluted hydrochloric acid, washed with saturated aqueous sodium chloride (500 mL×2 times), dried over anhydrous sodium sulfate, filtered, concentrated in vacuo, and purified by silica gel flash chromatography (dichloromethane:methanol=20:1) to give the title compound. Thin layer chromatography demonstrated a yield of about 80%.

1-3) Step c: Synthesis of 2,3,4-tri-O-benzyl-1-O-(2-propenyl)-6-O-triphenylmethyl-D-glucose (IV)

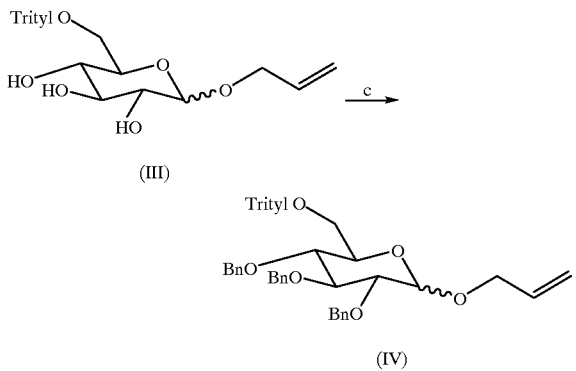

Two grams (83.3 mmol) of 80% sodium hydride dispersed in a mineral oil were put into a reactor, and were sufficiently washed with 50 mL of anhydrous hexane. Then, the hexane was removed from the reactor, to which 10.0 g (21.6 mmol) of 1-O-(2-propenyl)-6-O-triphenylmethyl-D-glucose (III) were slowly added under an ice-cooled condition. After 15 minutes, the reaction mixture was returned to room temperature, and reacted for 1 hour while stirring.

Next, 12.0 g (70.2 mmol) of benzylbromide were slowly added to the reaction mixture again under an ice-cooled condition. After 15 minutes, the reaction mixture was returned to room temperature, and was reacted for 3 hours while stirring. Then, 20 mL of methanol and 30 mL of cold distilled water were added to the reaction mixture to quench the reaction, and the reaction mixture was extracted with ethyl acetate (50 mL×3 times). The organic layers were combined, washed with saturated aqueous sodium chloride (100 mL×2 times), dried over anhydrous sodium sulfate, filtered, concentrated in vacuo, and purified by silica gel flash chromatography (hexane:ethyl acetate=10:1) to give 9.6 g (13.8 mmol) of the title compound. Yield: 63.9%.

1-4) Step d: Synthesis of 2,3,4-tri-O-benzyl-1-O-(2-propenyl)-α-D-glucose (V)

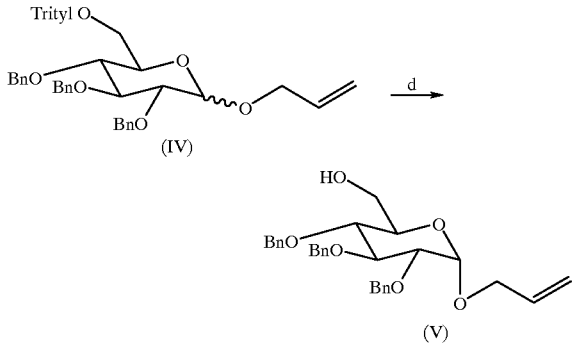

Into 100 mL of methanol, 9.6 g (13.8 mmol) of 2,3,4-tri-O-benzyl-1-O-(2-propenyl)-6-O-triphenylmethyl-D-glucose (IV) were dissolved, and 3.8 g (20.0 mmol) of p-toluenesulfonic acid monohydrate were added. The solution was reacted for 16 hours while stirring. Then, the reaction was quenched by adding 100 mL of cold distilled water, and the reaction mixture was extracted with ethyl acetate (200 mL×3 times). The organic layers were combined, washed with saturated aqueous sodium chloride (300 mL×2 times), dried over anhydrous sodium sulfate, filtered, concentrated in vacuo, and applied to silica gel flash chromatography (hexane:ethyl acetate=11:2→4:1→2:1), separating and purifying α- and β-anomers. The α-anomer in 2.70 g (5.50 mmol) with yield of 39.8%; and the β-anomer in 1.52 g (3.10 mmol) with yield of 22.5%.

1-5) Step e: Synthesis of 2,3 4-tri-O-benzyl-1-O-(2-propenyl)-6-O-(4-tolylsulfonyl)-α-D-glucose (VI)

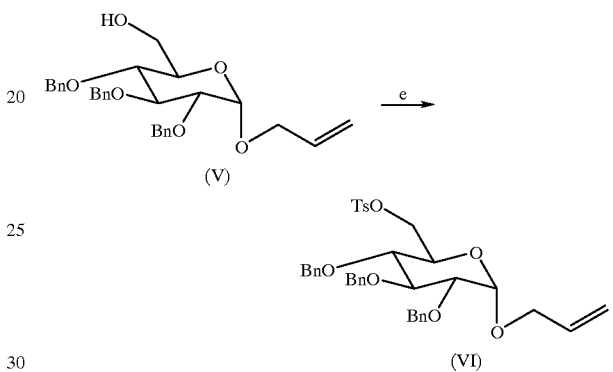

Into 200 mL of anhydrous pyridine, 10.0 g (20.4 mmol) of 2,3,4-tri-O-benzyl-1-O-(2-propenyl)-α-D-glucose (V) were dissolved, and then 134 mg (1.10 mmol) of DMAP and 9.2 g (48.3 mmol) of p-toluenesulfonyl chloride were added. The solution was reacted for 16 hours at room temperature while stirring. Then, the reaction was quenched by adding 300 mL of cold distilled water, and the reaction mixture was extracted with ethyl acetate (200 mL×3 times). The resultant organic layers were combined, acidified to pH 4 with diluted hydrochloric acid, washed with saturated aqueous sodium chloride (300 mL×2 times), dried over anhydrous sodium sulfate, filtered, concentrated in vacuo, and purified by silica gel flash chromatography (hexane:ethyl acetate=4:1) to give 12.0 g (18.6 mmol) of the tile compound with yield of 91.2%. Melting point: 77–79° C.; $[\alpha]_D$=+51. 8 ($CHCl_3$).

TABLE 5

| Absorption Peak (cm$^{-1}$) | IR Data Structure |
| --- | --- |
| 1940, 1860, 1800 | Mono-substituted Ar* |
| 1615 | Terminal double bond |
| 1593, 1480 | Ar* |
| 1170–1120, 1100–1000 | CO |
| 1180 | $SO_3$ |
| 910, 830 | α-Hexose characteristic absorption |

*Ar represents aromatics.

Figure 1B:
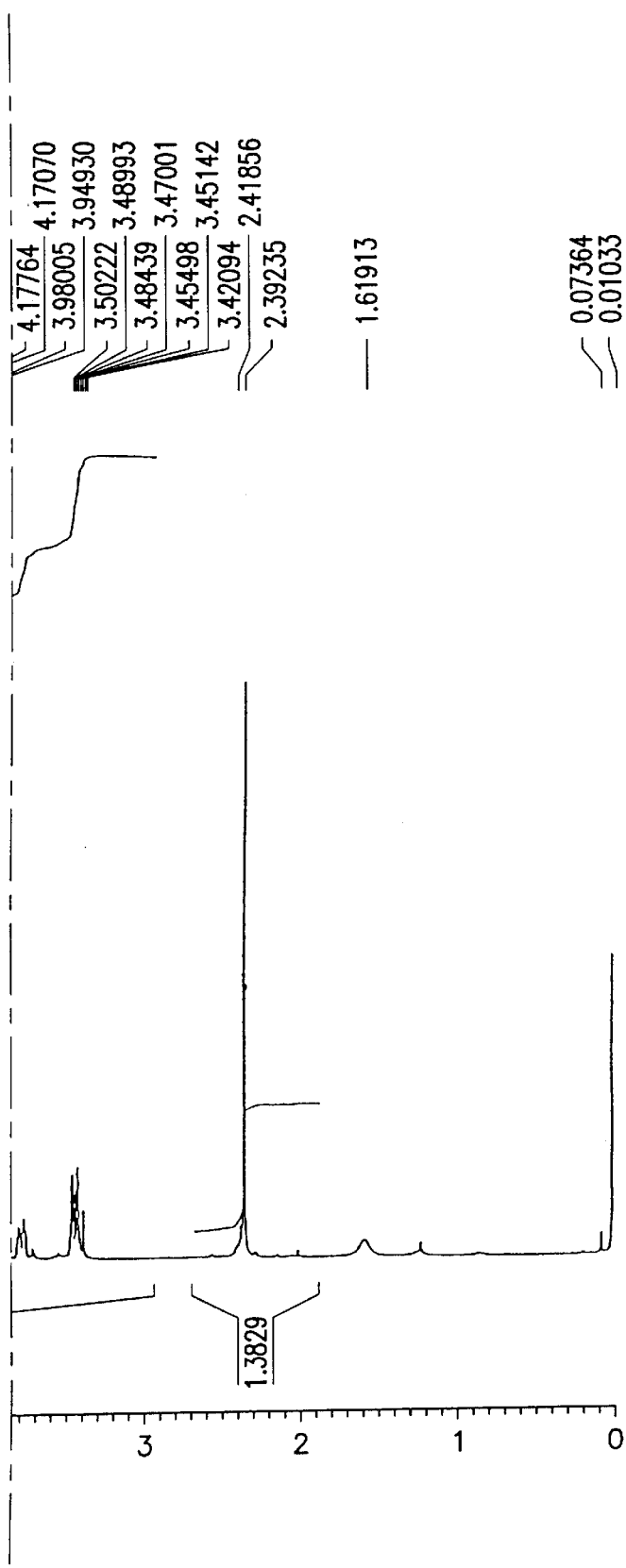
Figure 2A:
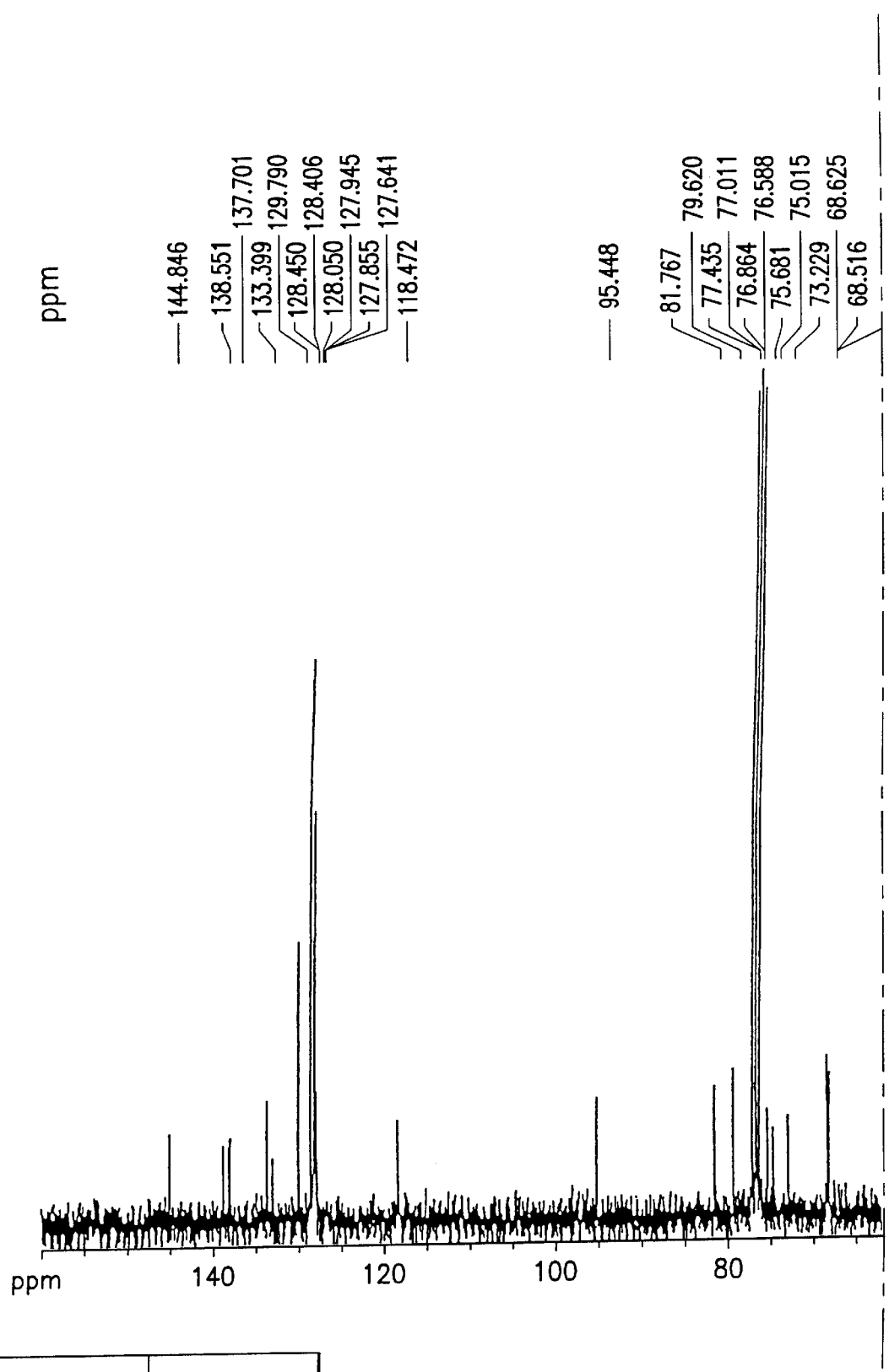
FIGS. 2A and 2B comprise a $^{13}$C NMR chart of 2,3,4-tri-O-benzyl-1-O-(2-propenyl)-6-O-(4-tolylsulfonyl)-α-D-glucose, which was produced in Example 1, which is described hereinbelow.
Figure 2B:
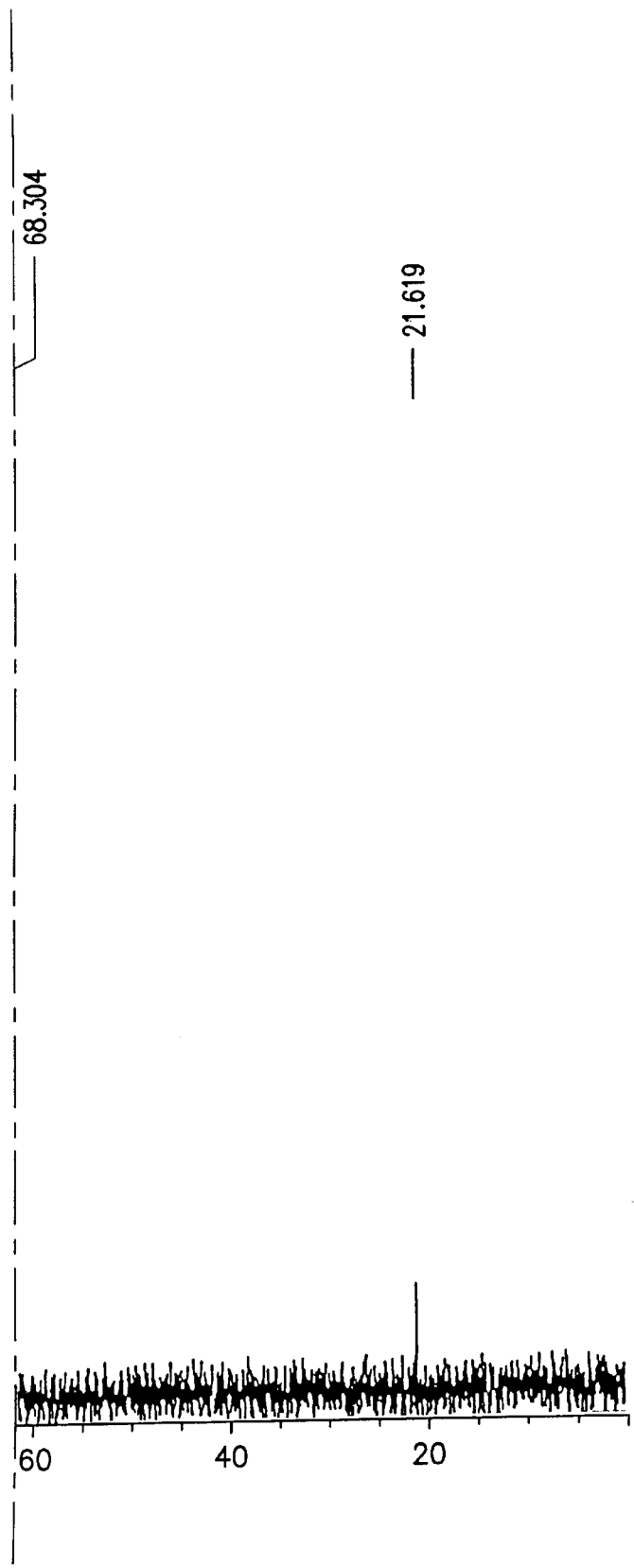

FIGS. 1A and 1B comprise a chart of $^1$H NMR (300 MHz, $CDCl_3$) in which tetramethylsilane was used as an internal standard substance, while FIGS. 2A and 2B comprise a chart of $^{13}$C NMR (300 MHz, $CDCl_3$) of the compound obtained.

Example 2

Synthesis (2) of a compound represented by Formula (A)

Starting from D-glucose (I'), 2,3,4-tri-O-(t-butyldimethylsilyl)-1-O-(2-propenyl)-6-O-(4-tolylsulfonyl)-α-D-glucose (VI') was synthesized through the following steps a'–e'.

2-1) Step a': Synthesis of 1-O-(2-propenyl)-D-glucose (II')

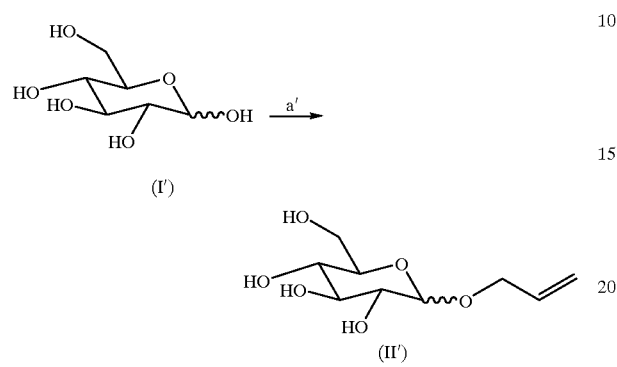

One hundred grams of D-glucose (I') were added to 250 mL of allyl alcohol and sufficiently dissolved therein. To the solution, 0.8 mL of trifluoromethanesulfonic acid were slowly added under an ice-cooled condition. Then, the solution was reacted in an oil bath at 80° C. for 30 hours while stirring. Then, the reaction mixture was neutralized by 1 mL of triethylamine, and was concentrated in vacuo to give the title compound. Thin layer chromatography demonstrated a yield of about 60–70%.

2-2) Step b': Synthesis of 1-O-(2-propenyl)-4,6-O-benzylidene-α-D-glucose (III').

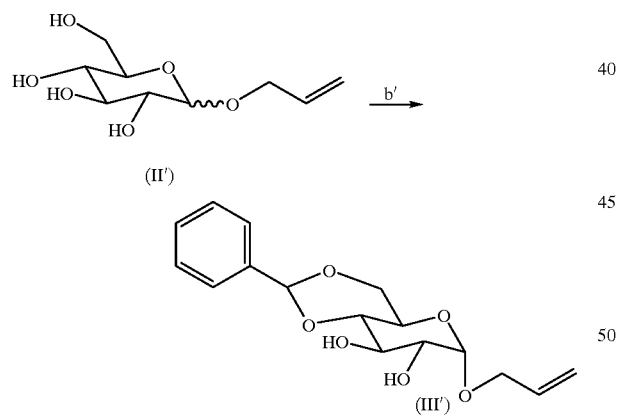

37.5 grams of 1-O-(2-propenyl)-D-glucose (II') were dissolved in 210 mL of benzaldehyde, and to the solution 98 g of zinc chloride were added. The reaction mixture was reacted at room temperature for 4 hours. Thereafter, the reaction mixture was added to 500 mL of hexane, and then 100 mL of diluted sodium hydrogen carbonate were added. The reaction mixture was allowed to stand at 0° C. for 30 minutes to be crystallized. The crystals were filtered with suction, and was dissolved into 50 mL of ethanol. The solution was allowed to stand at 0° C. for 30 minutes for recrystallization to give 21 g (68.1 mmol) of the title compound with yield of 40.0%.

2-3) Step c': Synthesis of 1-O-(2-propenyl)-α-D-glucose (IV')

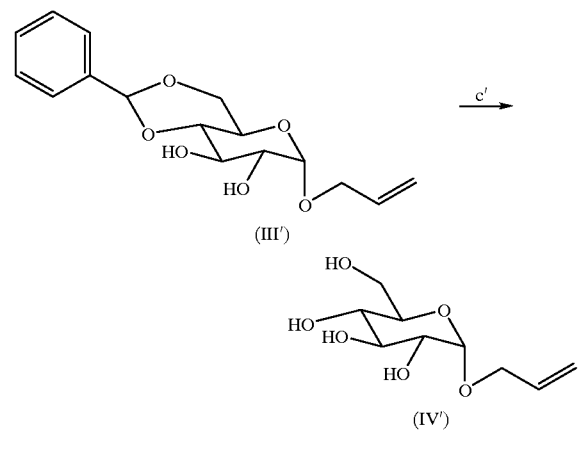

Into 260 mL of a solution of acetic acid and water (8:5), 10.7 g (34.7 mmol) of 1-O-(2-propenyl)-4,6-O-benzylidene-α-D-glucose (III') were dissolved. The solution was reacted at 100° C. for 1 hour, concentrated in vacuo, and purified by silica gel flash chromatography (dichlorormethane:methanol=6:1) to give 6.3 g (28.6 mmol) of the title compound with yield of 82.4%.

2-4) Step d': Synthesis of 1-O-(2-propenyl)-6-O-(4-tolylsulfonyl)-α-D-glucose (V')

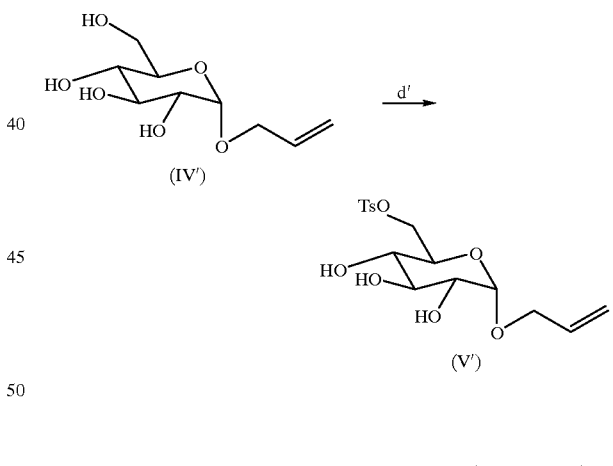

Into 200 mL of anhydrous pyridine, 6.3 g (28.6 mmol) of 1-O-(2-propenyl)-α-D-glucose (IV') were dissolved, and 195 mg of DMAP and 7.0 g of p-toluenesulfonyl chloride were added. The reaction was reacted for 16 hours at room temperature while stirring. Thereafter, the reaction was quenched by adding 20 mL of cold distilled water, and the reaction mixture was extracted with ethyl acetate (200 mL×3 times). The organic layers were combined, acidified to pH 4 with 1.0 N and 0.1 N hydrochloric acids, washed with saturated aqueous sodium chloride (200 mL×2 times), dried over anhydrous sodium sulfate, filtered, concentrated in vacuo, and purified by silica gel flash chromatography (dichloromethane:methanol=20:1) to give 8.6 g (24.0 mmol) of the title compound with yield of 83.8%.

2-5) Step e': Synthesis of 2,3,4-tri-O-(t-butyldimethylsilyl)-1-O-(2-propenyl)-6-O-(4-tolylsulfonyl)-α-D-glucose (VI')

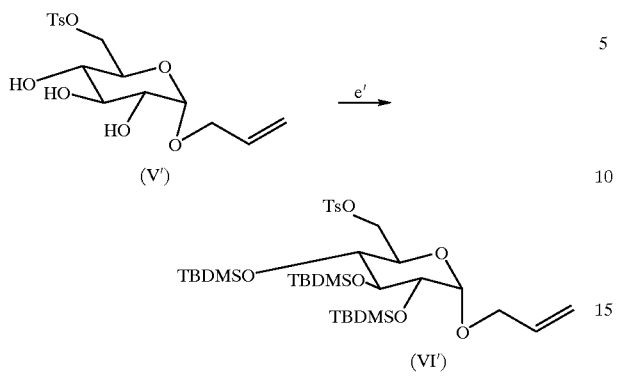

Into 25 mL of anhydrous dichloromethane, 11.2 g (29.9 mmol) of 1-O-(2-propenyl)-6-O-(4-tolylsulfonyl)-α-D-glucose (V') were dissolved and 23.8 g of t-butyldimethylsilyltrifluoromethane sulfonate and 14.4 g of 2,6-lutidine were added. The solution was reacted under nitrogen flow for 16 hours while stirring. Thereafter, the reaction was quenched by adding 150 mL of dichloromethane, and the reaction mixture was washed with saturated aqueous sodium chloride (100 mL×2 times), dried over anhydrous sodium sulfate, filtered, concentrated in vacuo, purified by silica gel flash chromatography (hexane:ethyl acetate=30:1) to give 19.6 g (27.4 mmol) of the title compound as a colorless and transparent oil.

Yield of 91.6%. $[\alpha]_D$=+39.0° (CHCl$_3$).

TABLE 6

IR DATA

| Absorption Peak (cm$^{-1}$) | Structure |
|---|---|
| 1735, 1590, 1475 | Ar |
| 1105–1000, 950 | CO |
| 1160 | SO$_3$ |
| 930, 825, 770 | α-Hexose characteristic absorption |

Figures 3, 3A:
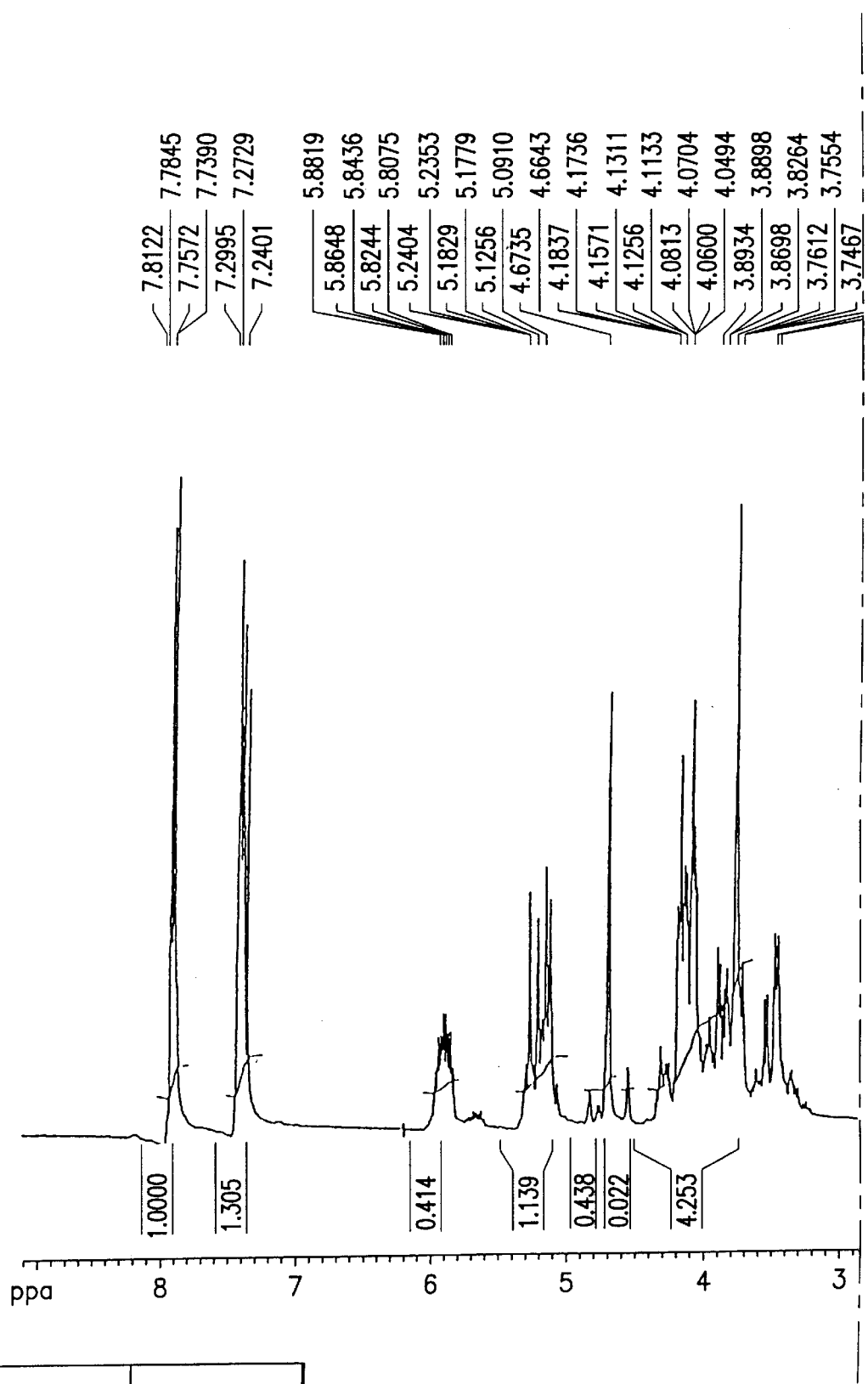
FIG. 3 is a $^1$H NMR chart of 2,3,4-tri-O-(t-butyldimethylsilyl)-1-O-(2-propenyl)-6-O-(4-tolylsulfonyl)-α-D-glucose, which was produced in Example 2 which will be described later.
FIGS. 3A and 3B comprise a ¹H NMR chart of 2,3,4-tri-O-(t-butyldimethylsilyl)-1-O-(2-propenyl)-6-O-(4-tolylsulfonyl)-α-D-glucose, which was produced in Example 2, which is described hereinbelow.
Figure 3B:
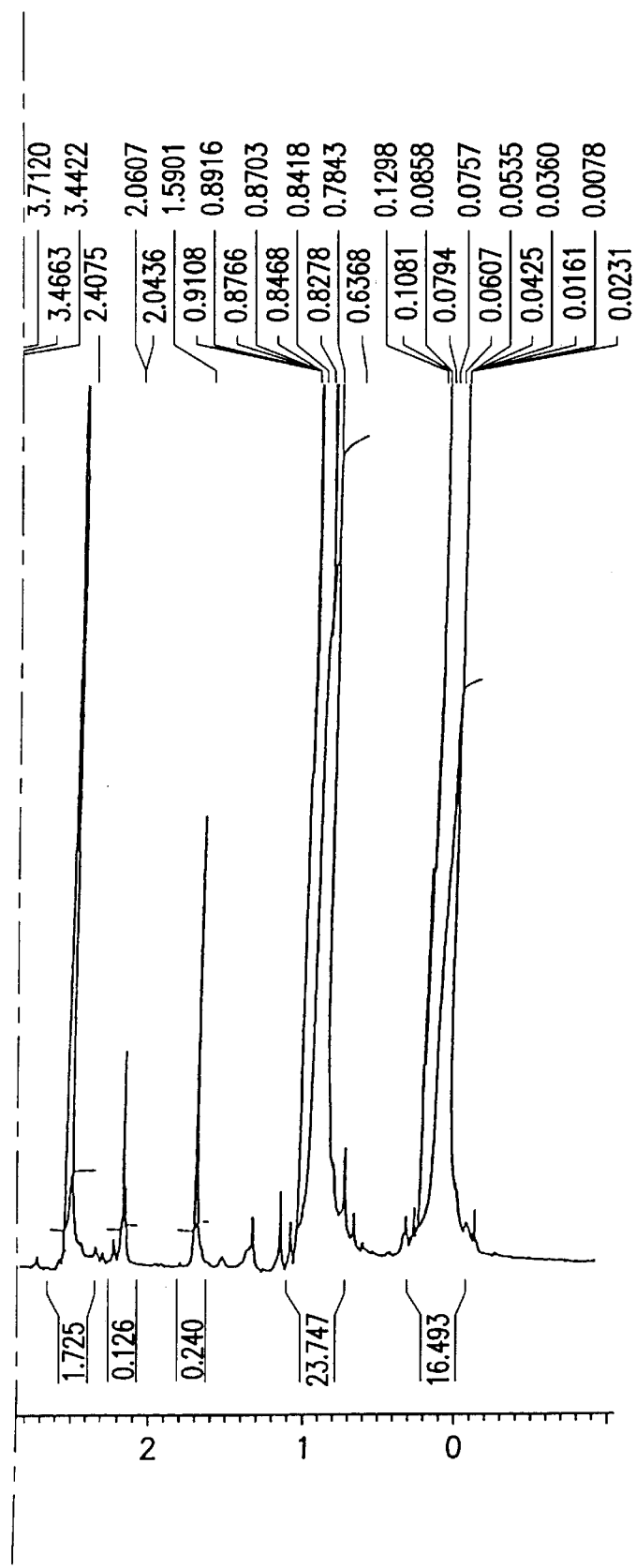
Figure 4A:
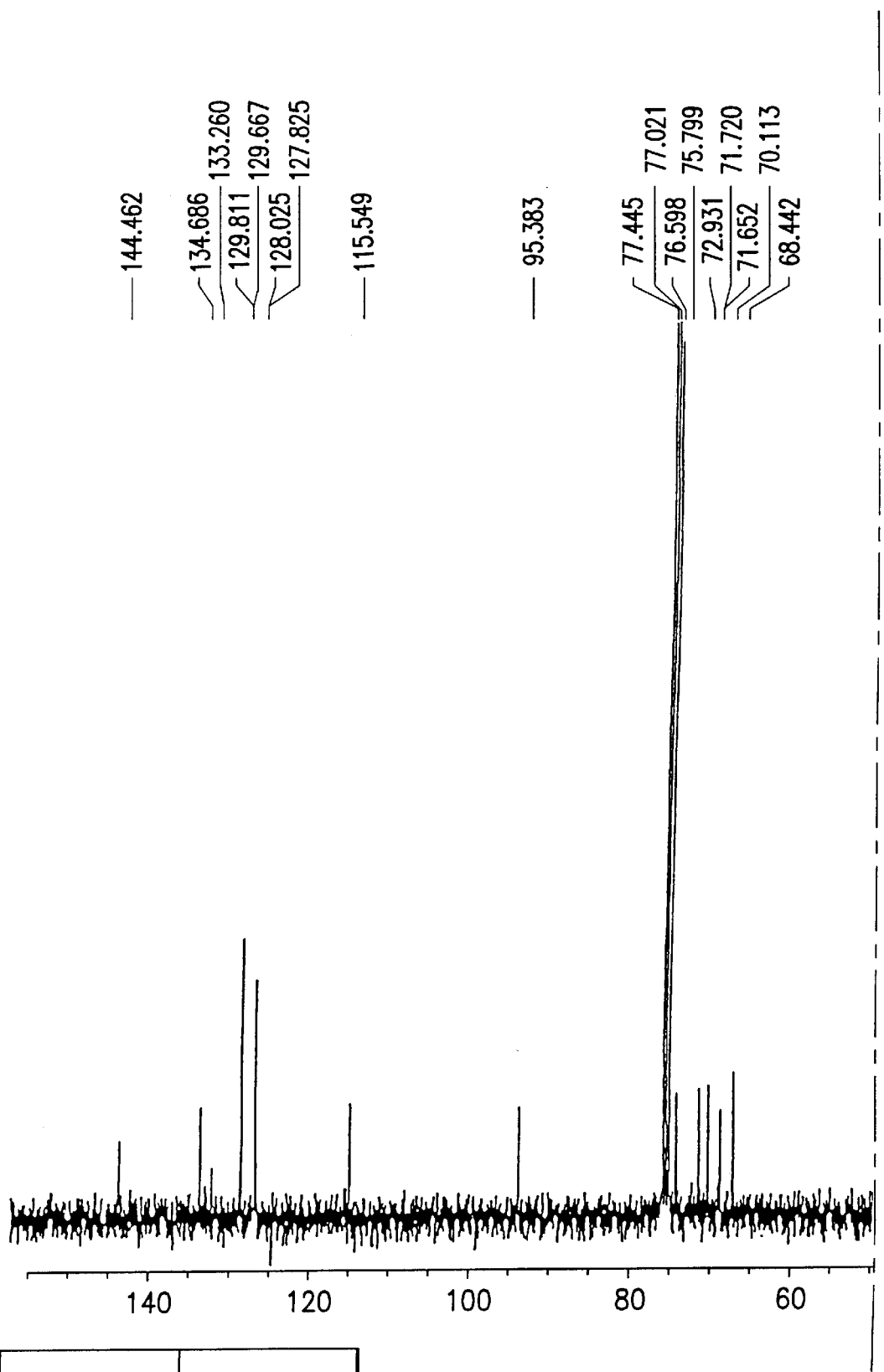
FIGS. 4A and 4B comprise a ¹³C NMR chart of 2,3,4-tri-O-(t-butyldimethylsilyl)-1-O-(2-propenyl)-6-O-(4-tolylsulfonyl)-α-D-glucose, which was produced in Example 2, which is described hereinbelow.
Figure 4B:
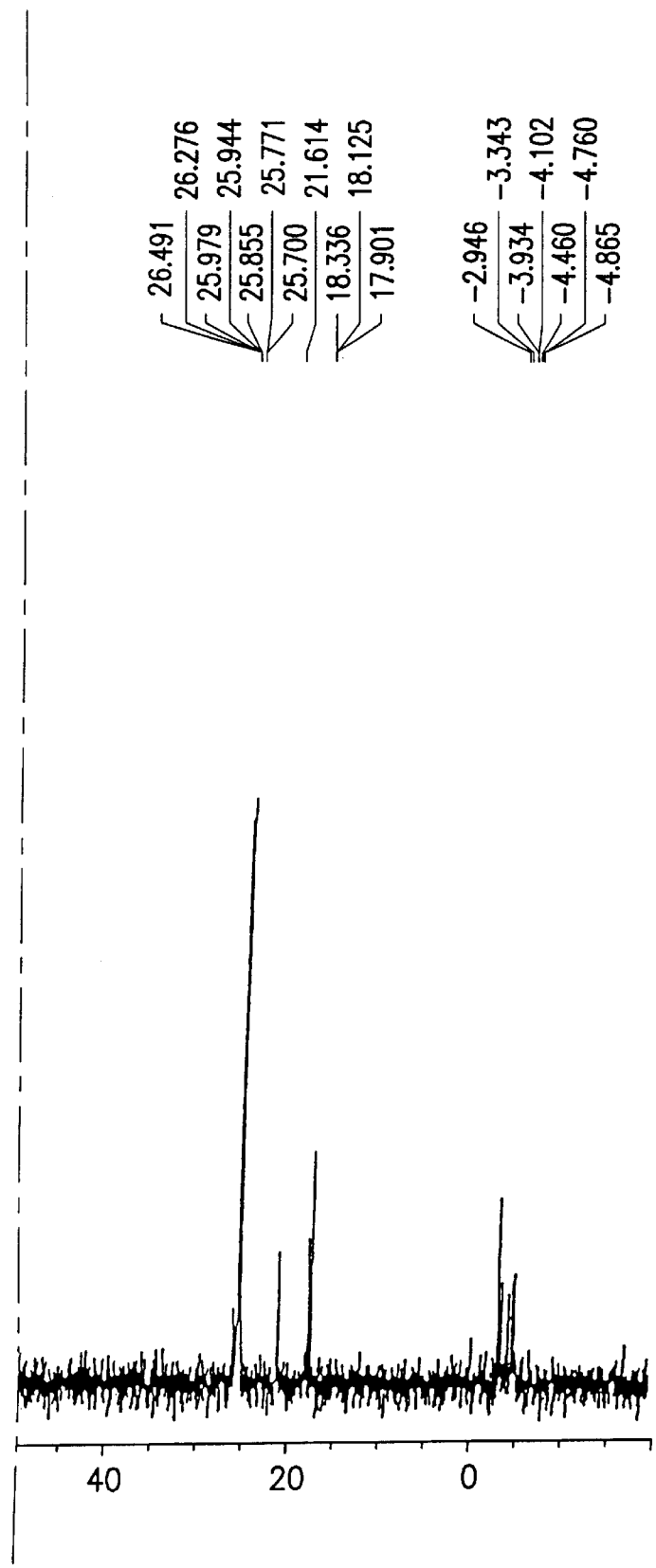

FIGS. 3A and 3B comprise a chart of $^1$H NMR (300 MHz, CDCl$_3$) in which tetramethylsilane was used as an internal standard substance, while FIGS. 4A and 4B comprise a chart of $^{13}$C NMR (300 MHz, CDCl$_3$) of the compound obtained.

Example 3

Synthesis (3) of a compound represented by Formula (A)

The steps a–e were carried out in the same manner as in Example 1 except that D-mannose was used instead of D-glucose as the starting material to give 2,3,4-tri-O-benzyl-1-O-(2-propenyl)-6-O-(4-tolylsulfonyl)-α-D-mannose (VI") as a colorless and transparent oily material.

$[\alpha]_D$=+34.1° (CHCl$_3$).

TABLE 7

IR DATA

| Absorption Peak (cm$^{-1}$) | Structure |
|---|---|
| 1945, 1860, 1790, 1700 | Mono-substituted Ar |
| 1625 | Terminal double bond |
| 1580, 1475 | Ar |
| 1105–1000, 950 | CO |
| 1160 | SO$_3$ |
| 910, 835, 795 | α-Hexose characteristic absorption |

Figure 5A:
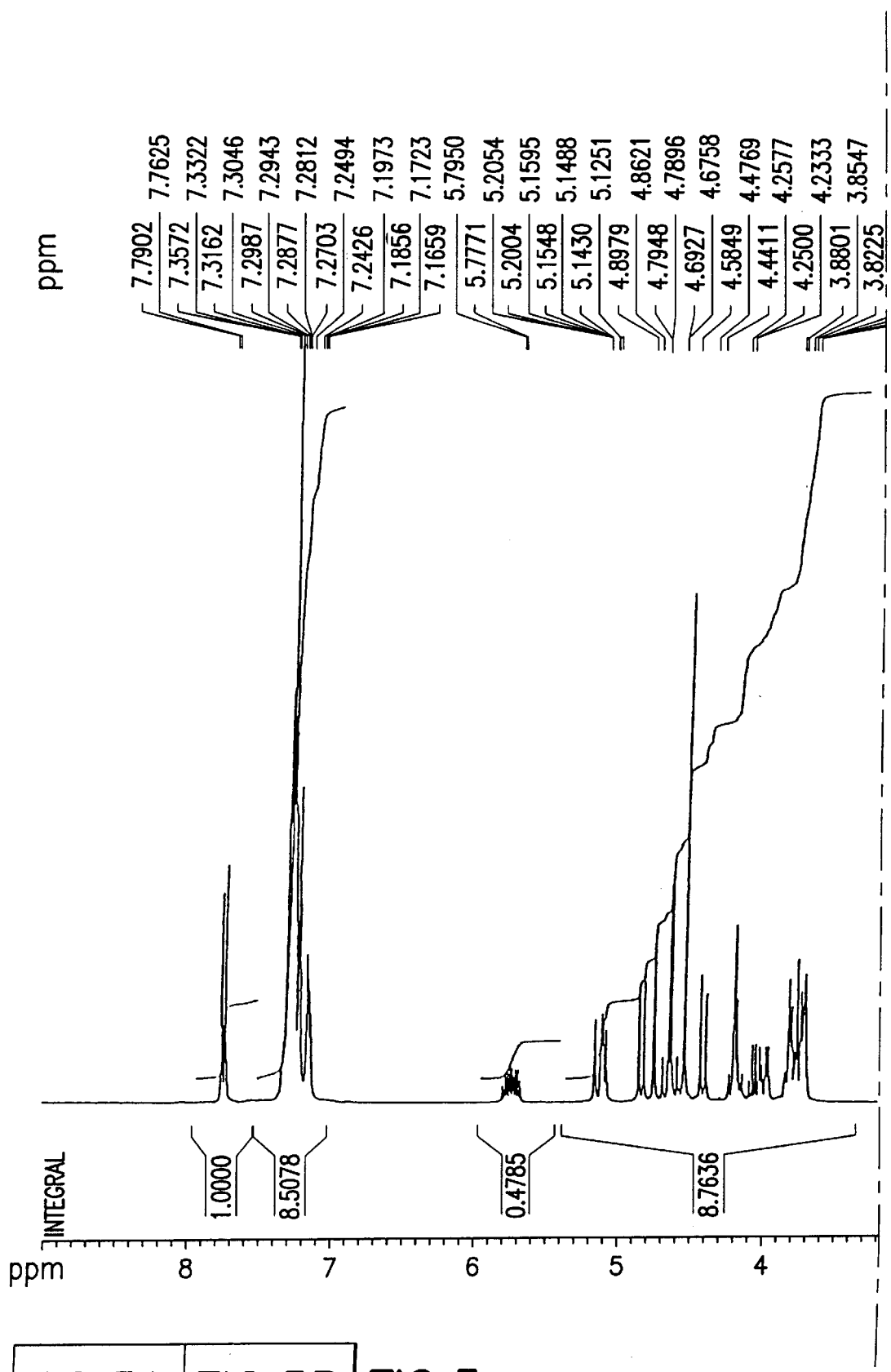
FIGS. 5A and 5B comprise a ¹H NMR chart of 2,3,4-tri-O-benzyl-1-O-(2-propenyl)-6-O-(4-tolylsulfonyl)-α-D-mannose, which was produced in Example 3, which is described hereinbelow.
Figure 5B:
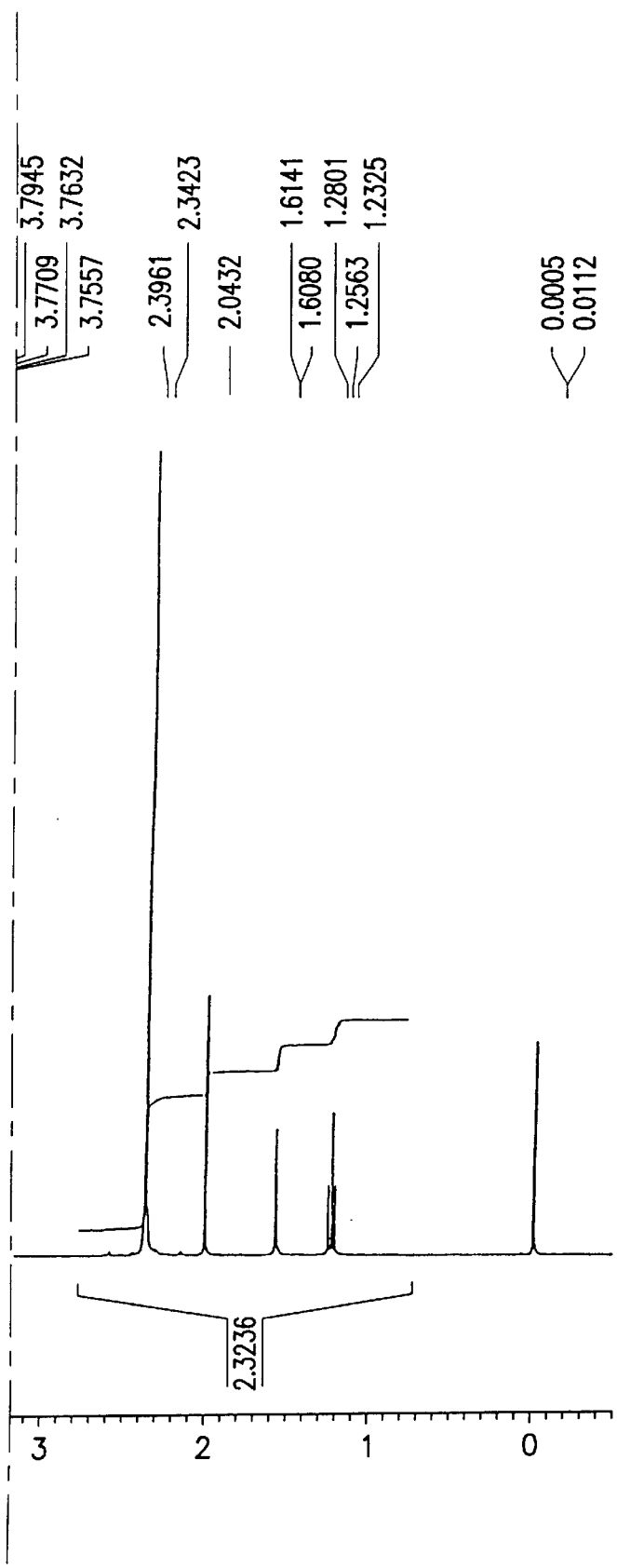
Figure 6A:
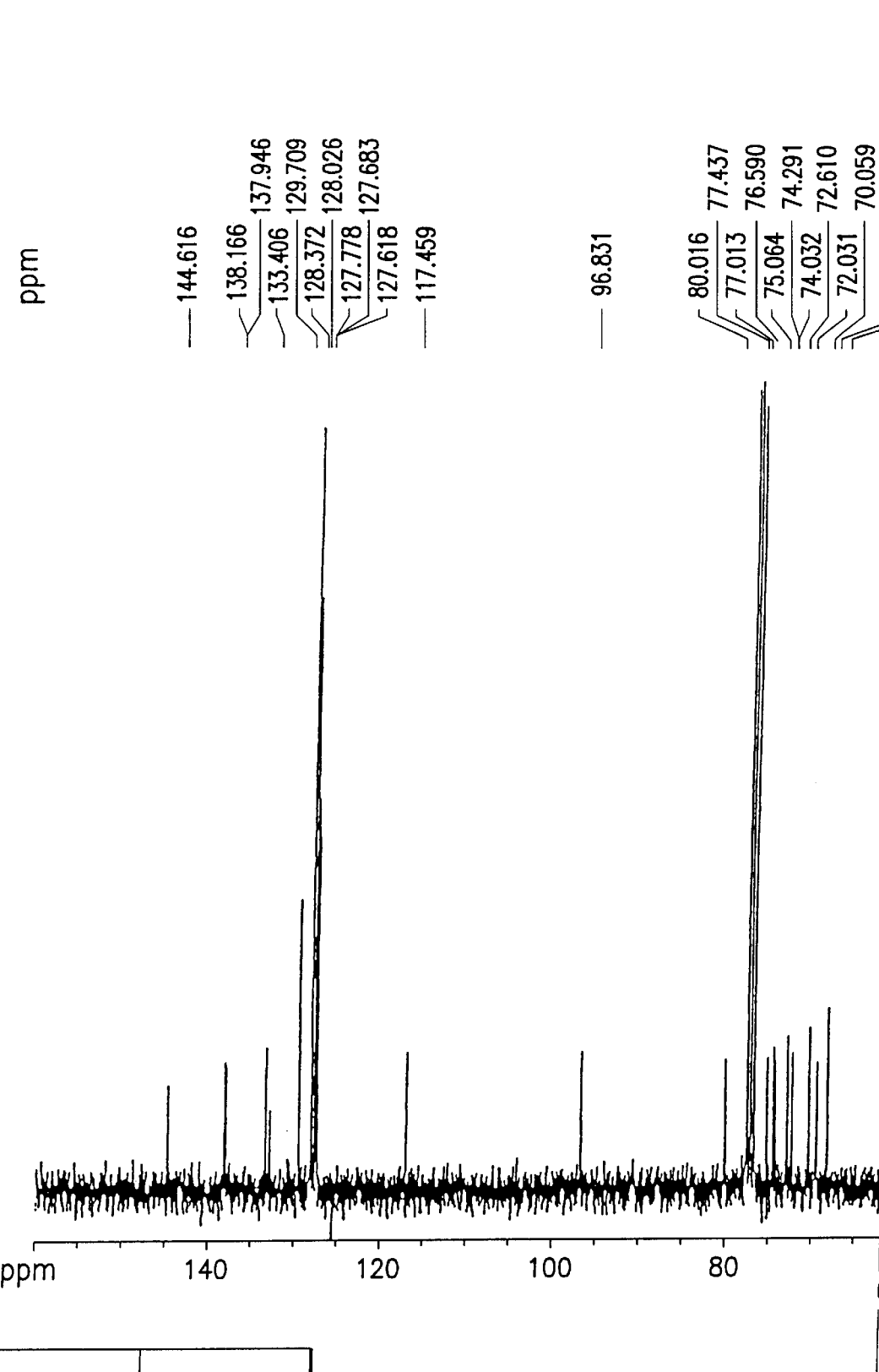
FIGS. 6A and 6B comprise a ¹³C NMR chart of 2,3,4-tri-O-benzyl-1-O-(2-propenyl)-6-O-(4-tolylsulfonyl)-α-D-mannose, which was produced in Example 3, which is described hereinbelow.
Figure 6B:
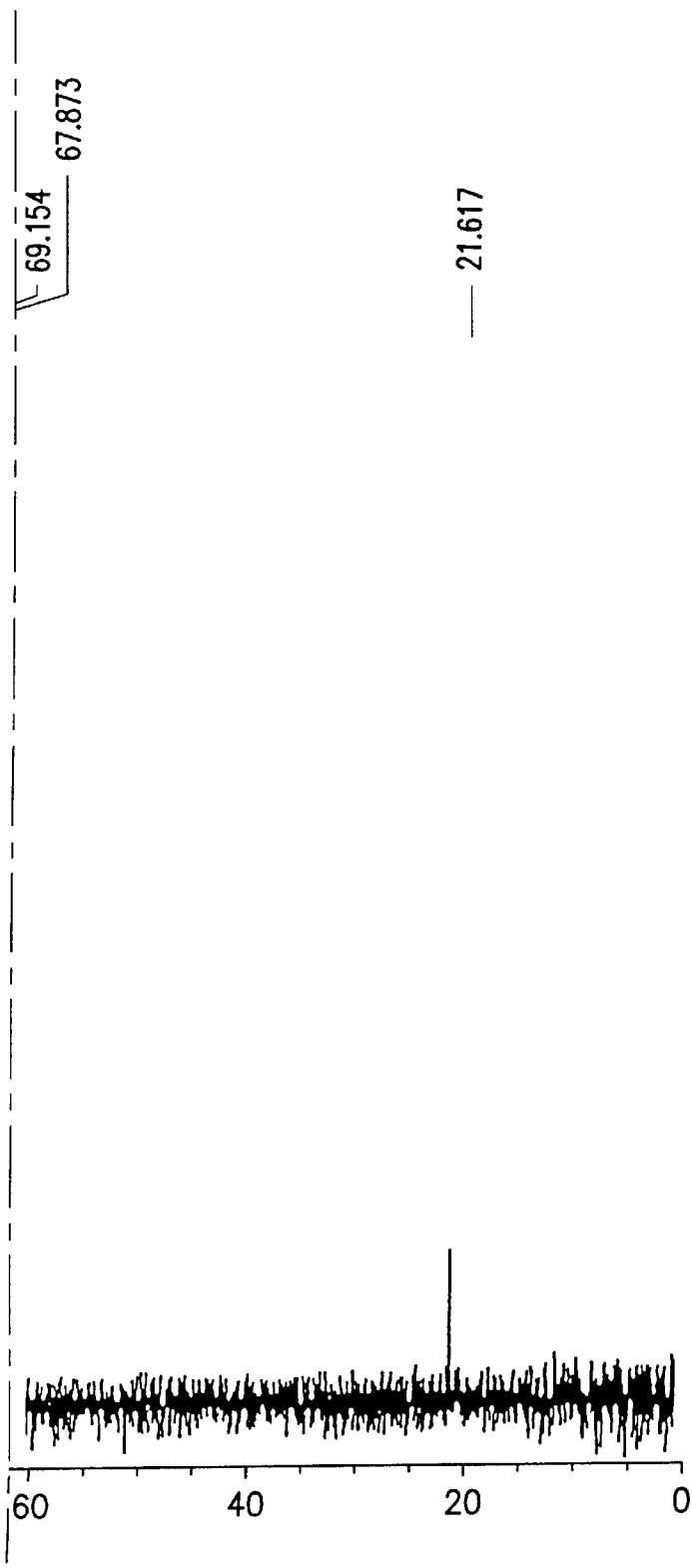

FIGS. 5A and 5B comprise a chart of $^1$H NMR (300 MHz, CDCl$_3$) in which tetramethylsilane was used as an internal standard substance, while FIGS. 6A and 6B comprise a chart of $^{13}$C NMR (300 MHz, CDCl$_3$) of the compound obtained.

Example 4

Synthesis (1) of a compound represented by Formula (B)

From 2,3,4-tri-O-benzyl-1-O-(2-propenyl)-6-O-(4-tolylsulfonyl)-α-glucose (VI) obtained in Example 1, 2,3,4-tri-O-benzyl-1-O-(2-propenyl)-6-deoxy-6-acetylthio-α-D-glucose (VII) was synthesized by the step f.

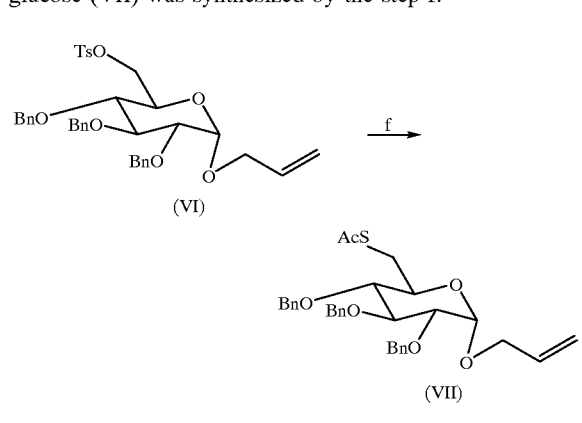

Into 250 mL of anhydrous ethanol, 11.4 g (18.6 mmol) of 2,3,4-tri-O-benzyl-1-O-(2-propenyl)-6-O-(4-tolylsulfonyl)-α-D-glucose (VI) were dissolved and then 5.6 g (49.0 mmol) of potassium thioacetate were added. The solution was reacted under reflux for 3 hours while stirring. Thereafter, the reaction was quenched by adding 300 mL of cold distilled water, and the reaction mixture was extracted with ethyl acetate (200 mL×3 times). The organic layers were combined, washed with saturated aqueous sodium chloride (300 mL×2 times), dried over anhydrous sodium sulfate, filtered, concentrated in vacuo, purified by silica gel flash chromatography (hexane:ethyl acetate=10:1) to give 9.00 g (16.4 mmol) of the title compound with yield of 88.2%.

Melting point: 61–62.5° C.; $[\alpha]_D$=+51.8° (CHCl$_3$).

TABLE 8

IR DATA

| Absorption Peak (cm$^{-1}$) | Structure |
| --- | --- |
| 1940, 1880, 1800 | Mono-substituted Ar |
| 1680 | SCOCH$_3$ |
| 1600, 1580, 1490 | Ar |
| 1160–1120, 1090–1060 | CO |
| 1180 | SO$_3$ |
| 905, 830 | α-Hexose characteristic absorption |

Figure 7A:
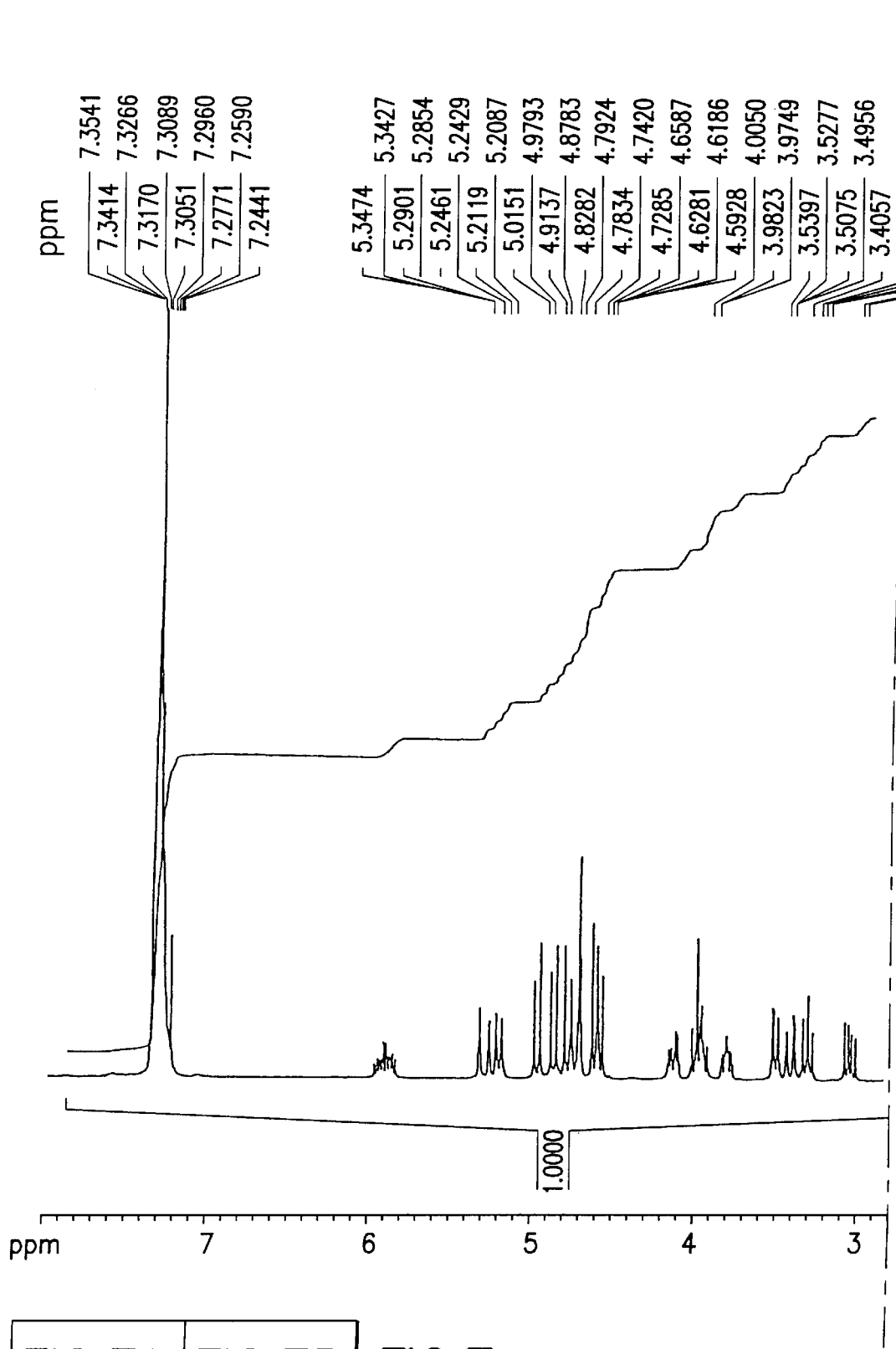
FIGS. 7A and 7B comprise a ¹H NMR chart of 2,3,4-tri-O-benzyl-6-deoxy-1-O-(2-propenyl)-6-acetylthio-α-D-glucose, which was produced in Example 4, which is described hereinbelow.
Figure 7B:
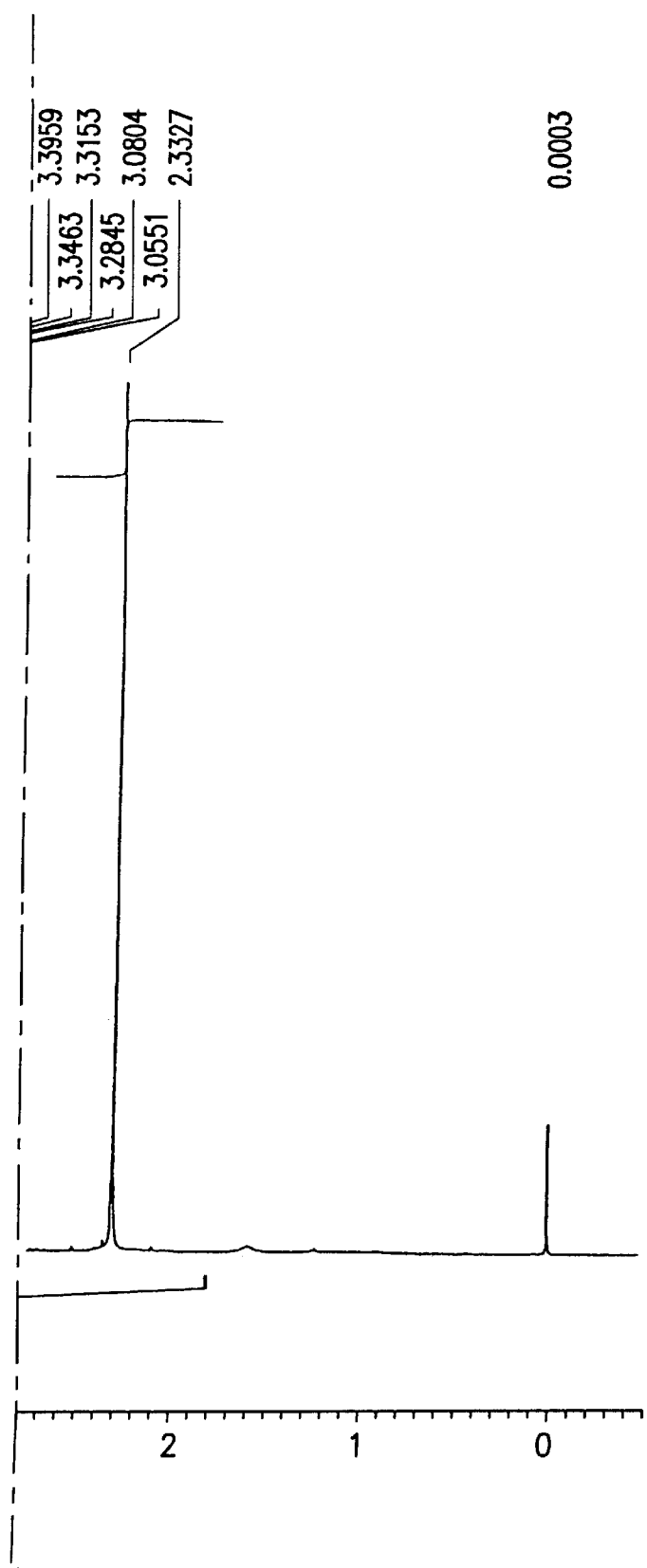
Figure 8A:
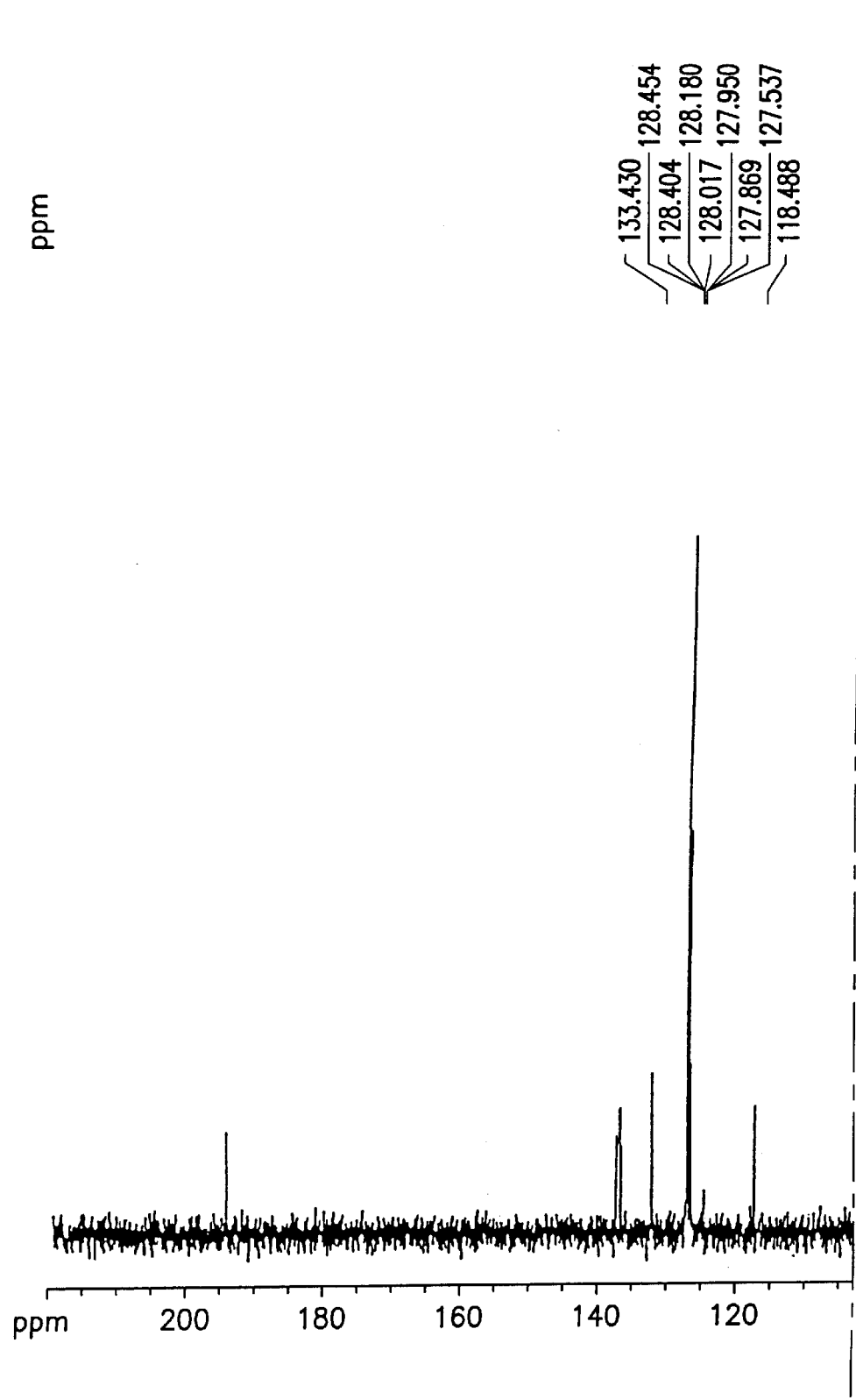
FIGS. 8A and 8B comprise a ¹³C NMR chart of 2,3,4-tri-O-benzyl-6-deoxy-1-O-(2-propenyl)-6-acetylthio-α-D-glucose, which was produced in Example 4, which is described hereinbelow.
Figure 8B:
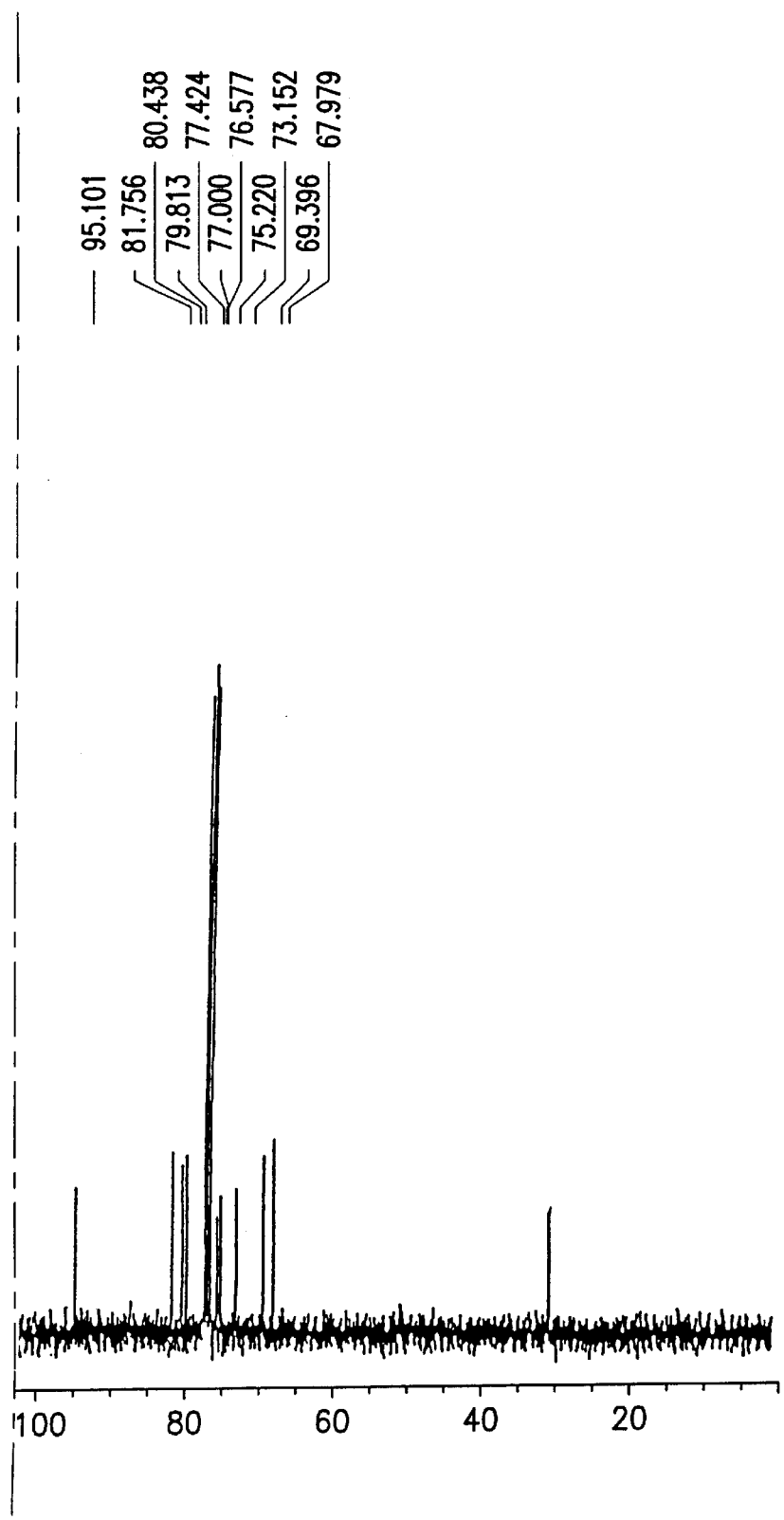

FIGS. 7A and 7B comprise a chart of $^1$H NMR (300 MHz, CDCl$_3$) in which tetramethylsilane was used as an internal standard substance, while FIGS. 8A and 8B comprise a chart of $^{13}$C NMR (300 MHz, CDCl$_3$) of the compound obtained.

Example 5

Synthesis (2) of a compound represented by Formula (B)

From 2,3,4-tri-O-(t-butyldimethylsilyl)-1-O-(2-propenyl)-6-O-(4-tolylsulfonyl)-α-D-glucose (VI') obtained in Example, 2,3,4-tri-O-(t-butyldimethylsilyl)-1-O-(2-propenyl)-6-deoxy-acetylthio-α-D-glucose (VII') was synthesized by the step f'.

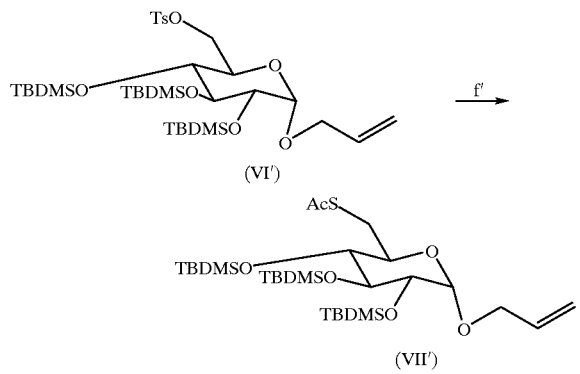

Into 20 mL of anhydrous ethanol, 7.9 g (11.0 mmol) of 2,3,4-tri-O-(t-butyldimethylsilyl)-1-O-(2-propenyl)-6-O-(4-tolylsulfonyl)-α-D-glucose (VI') were dissolved, and then 1.8 g of potassium thioacetate were added. The solution was reacted under reflux for 3 hours while stirring. Thereafter, the reaction was quenched by adding 100 mL of cold distilled water, and the reaction mixture was extracted with ethyl acetate (200 ml×3 times). The organic layers were combined, washed with saturated aqueous sodium chloride (200 mL×2 times), dried over anhydrous sodium sulfate, filtered, concentrated in vacuo, and purified by silica gel flash chromatography (hexane:ethyl acetate=50:1) to give 5.6 g (9.02 mmol) of the title compound as a colorless and transparent oily material. Yield of 82.0%.

$[\alpha]_D$=+60.9° (CHCl$_3$).

TABLE 9

IR DATA

| Absorption Peak (cm$^{-1}$) | Structure |
| --- | --- |
| 1670 | SCOCH$_3$ |
| 1620 | Terminal double bond |
| 1140–1000 | CO |
| 910, 810, 755 | α-Hexose characteristic absorption |

Figure 9A:
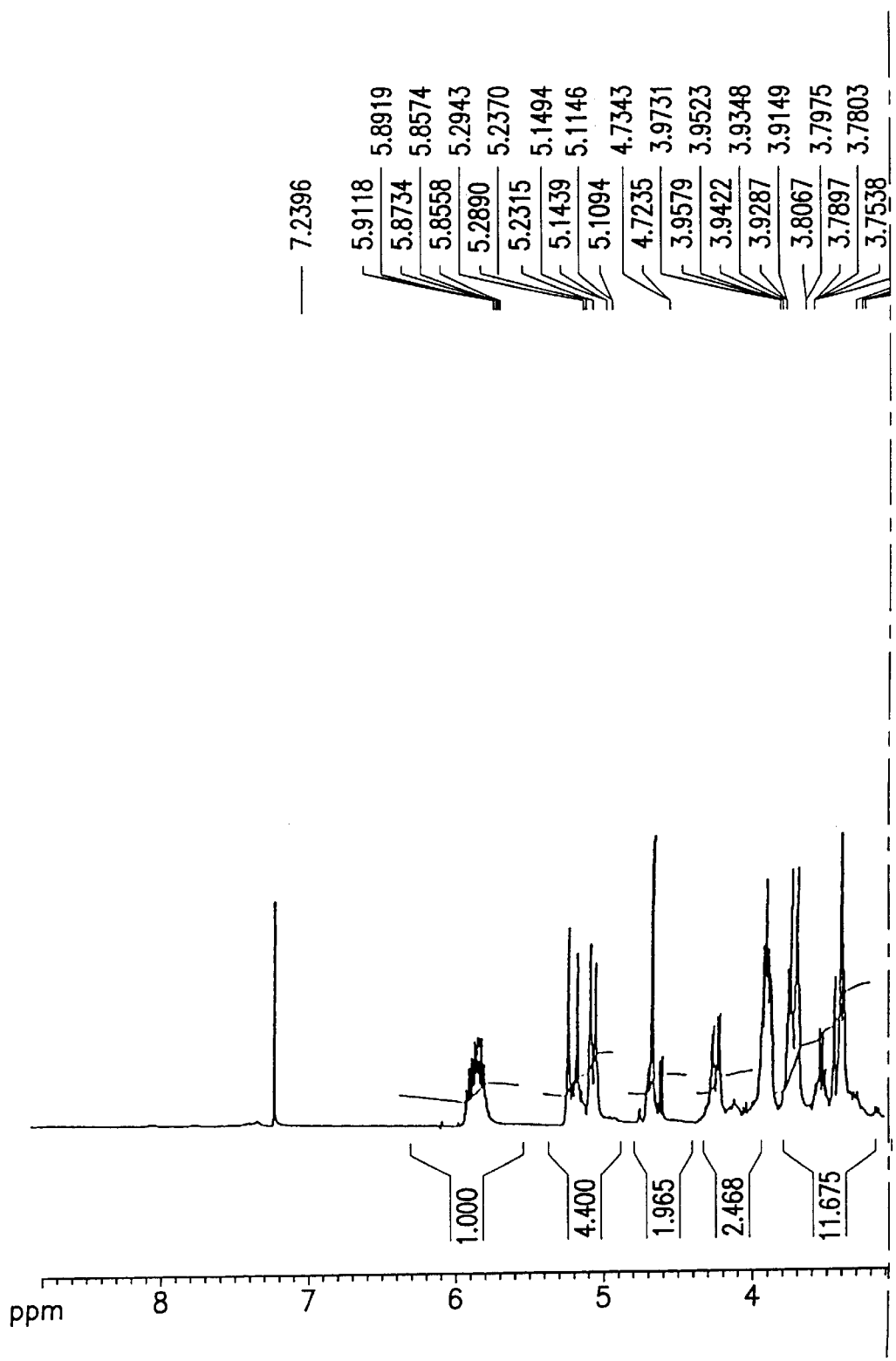
FIGS. 9A and 9B comprise a ¹H NMR chart of 2,3,4-tri-O-(t-butyldimethylsilyl)-6-deoxy-1-O-(2-propenyl)-6-acetylthio-α-D-glucose, which was produced in Example 5, which is described hereinbelow.
Figure 9B:
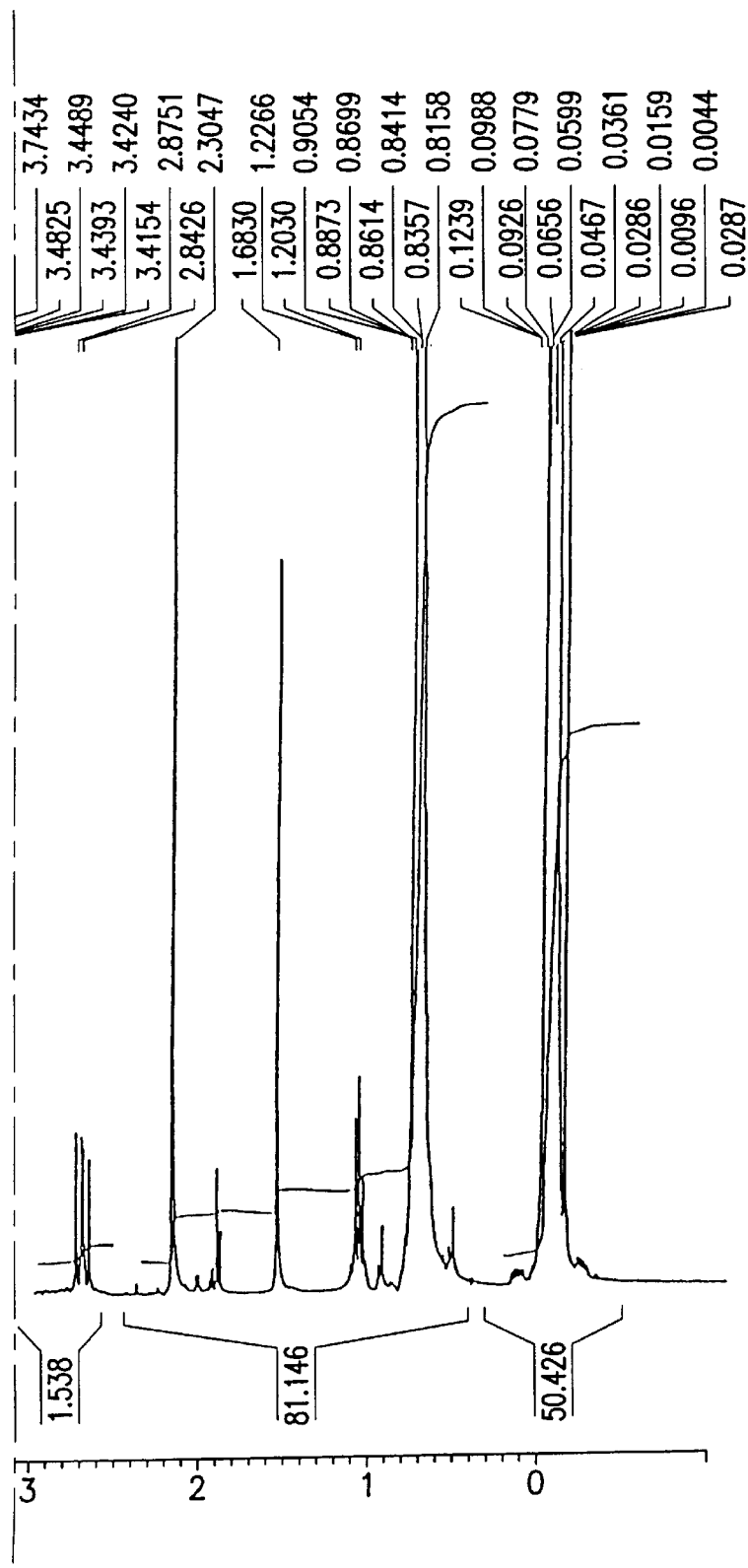
Figure 10A:
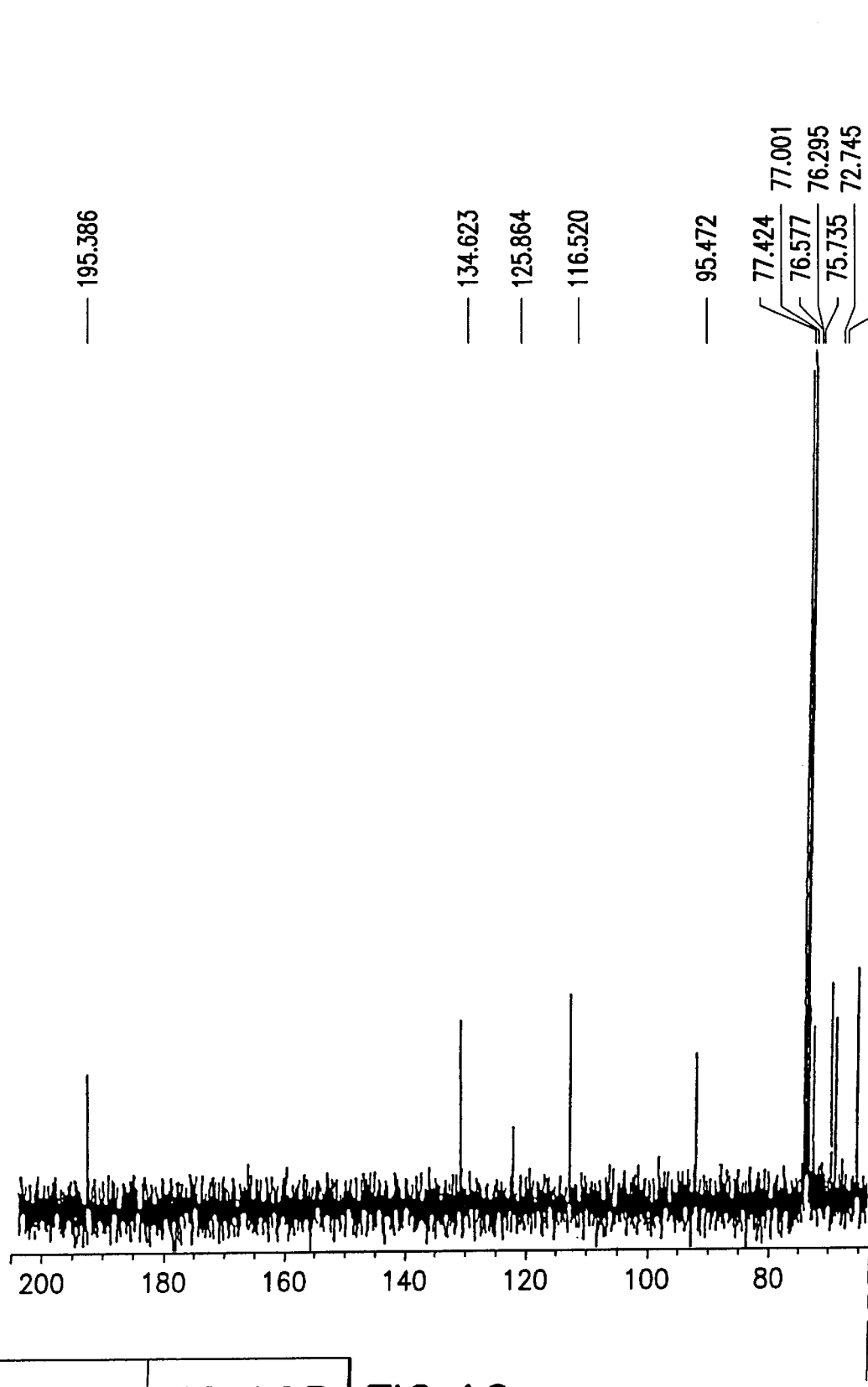
FIGS. 10A and 10B comprise a ¹³C NMR chart of 2,3,4-tri-O-(t-butyldimethylsilyl)-6-deoxy-1-O-(2-propenyl)-6-acetylthio-α-D-glucose, which was produced in Example 5, which is described hereinbelow.
Figure 10B:
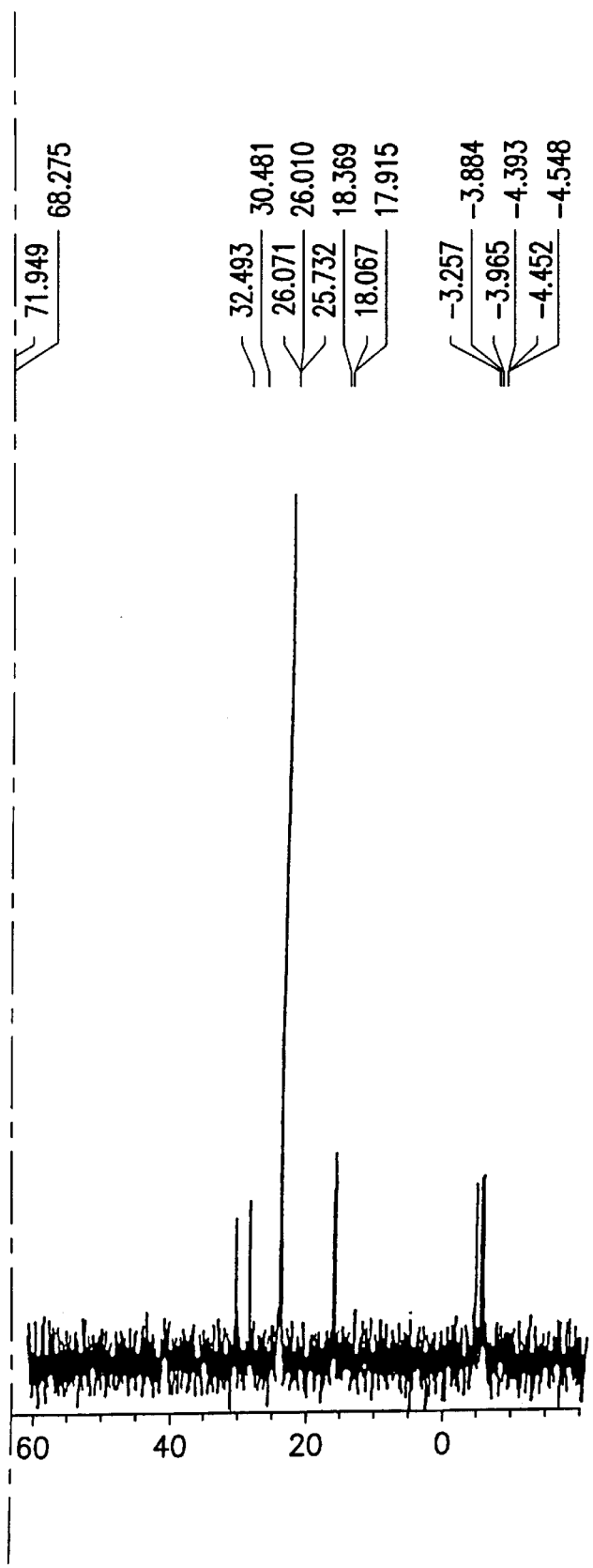

FIGS. 9A and 9B comprise a chart of $^1$H NMR (300 MHz, CDCl$_3$) in which tetramethylsilane was used as an internal standard substance, while FIGS. 10A and 10B comprise a chart of $^{13}$C NMR (300 MHz, CDCl$_3$) of the compound obtained.

Example 6

Synthesis (3) of a compound represented by Formula (B)

In the same manner as in the step f in Example 4, from 2,3,4-tri-O-benzyl-1-O-(2-propenyl)-6-O-(4-tolylsulfonyl)-α-D-mannose (VI'') obtained in Example 3, 2,3,4-tri-O-benzyl-6-deoxy-1-O-(2-propenyl)-6-acetylthio-α-D-mannose (VII'') was synthesized as a pale yellow and transparent material.

$[\alpha]_D$=+32.1° (CHCl$_3$).

TABLE 10

IR DATA

| Absorption Peak (cm$^{-1}$) | Structure |
| --- | --- |
| 3120, 3040 | Ar |
| 1950, 1870, 1800, 1750 | Mono-substituted Ar |
| 1680 | SCOCH$_3$ |
| 1640 | Terminal double bond |
| 1595, 1575, 1490 | Ar |
| 1135–950 | CO |
| 910, 830, 785 | α-Hexose characteristic absorption |

Figure 11A:
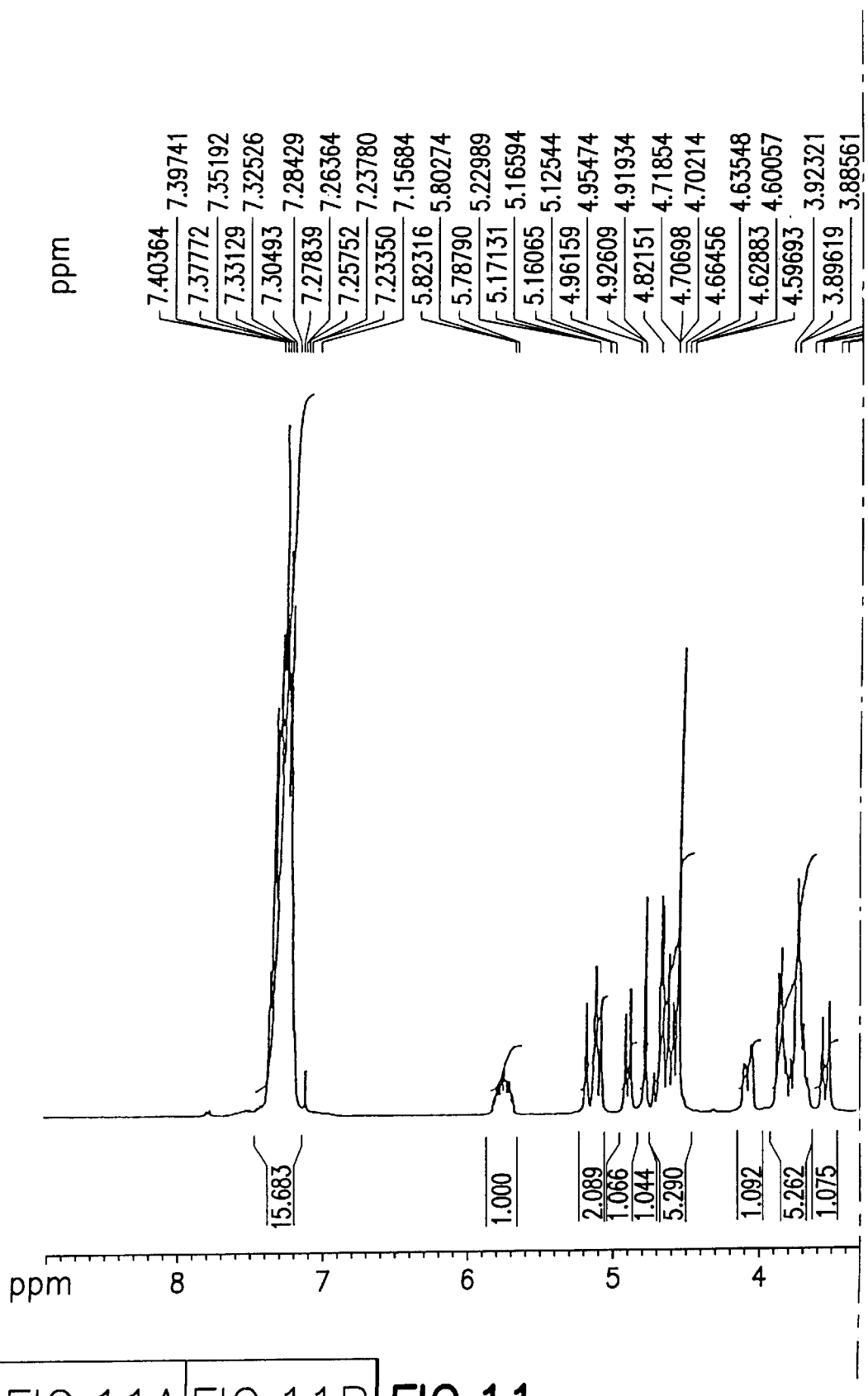
FIGS. 11A and 11B comprise a ¹H NMR chart of 2,3,4-tri-O-benzyl-6-deoxy-1-O-(2-propenyl)-6-acetylthio-α-D-mannose, which was produced in Example 6, which is described hereinbelow.
Figure 11B:
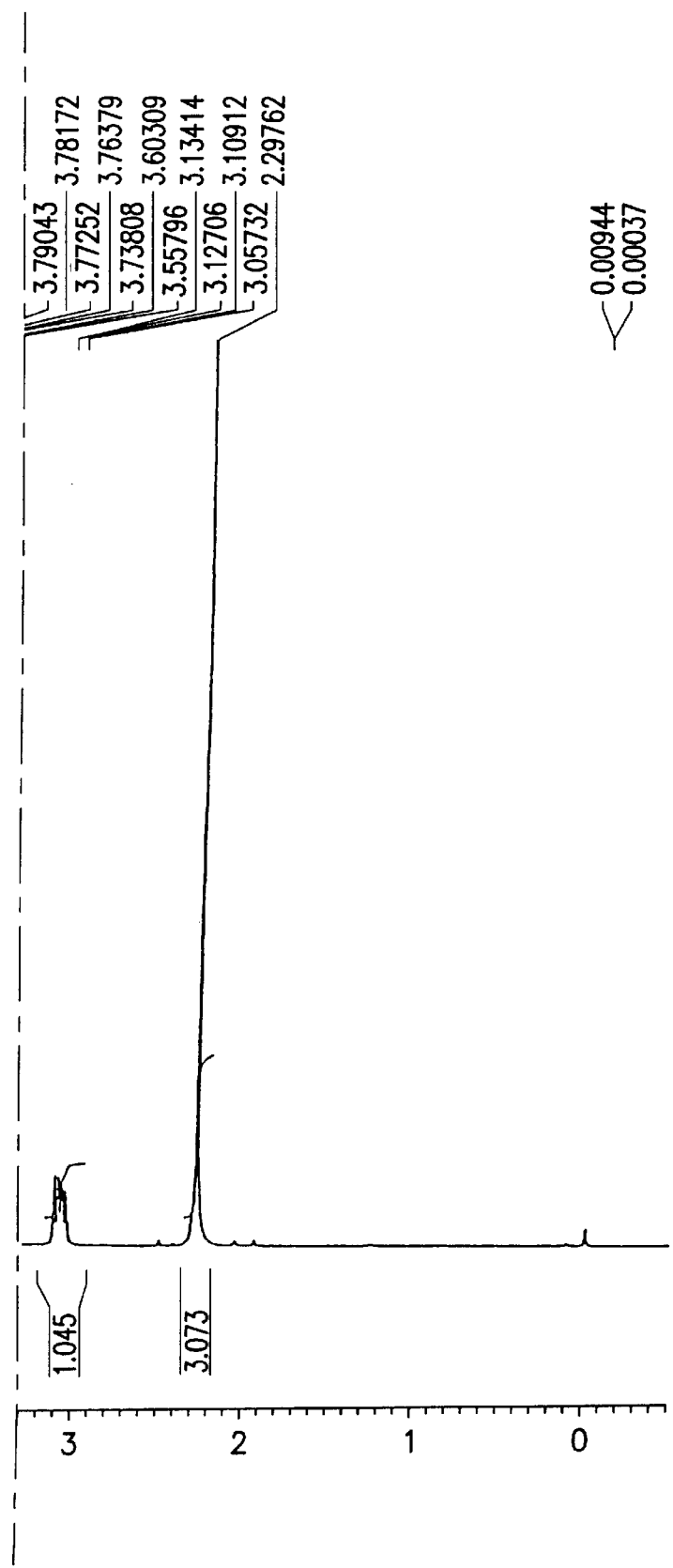
Figure 12A:
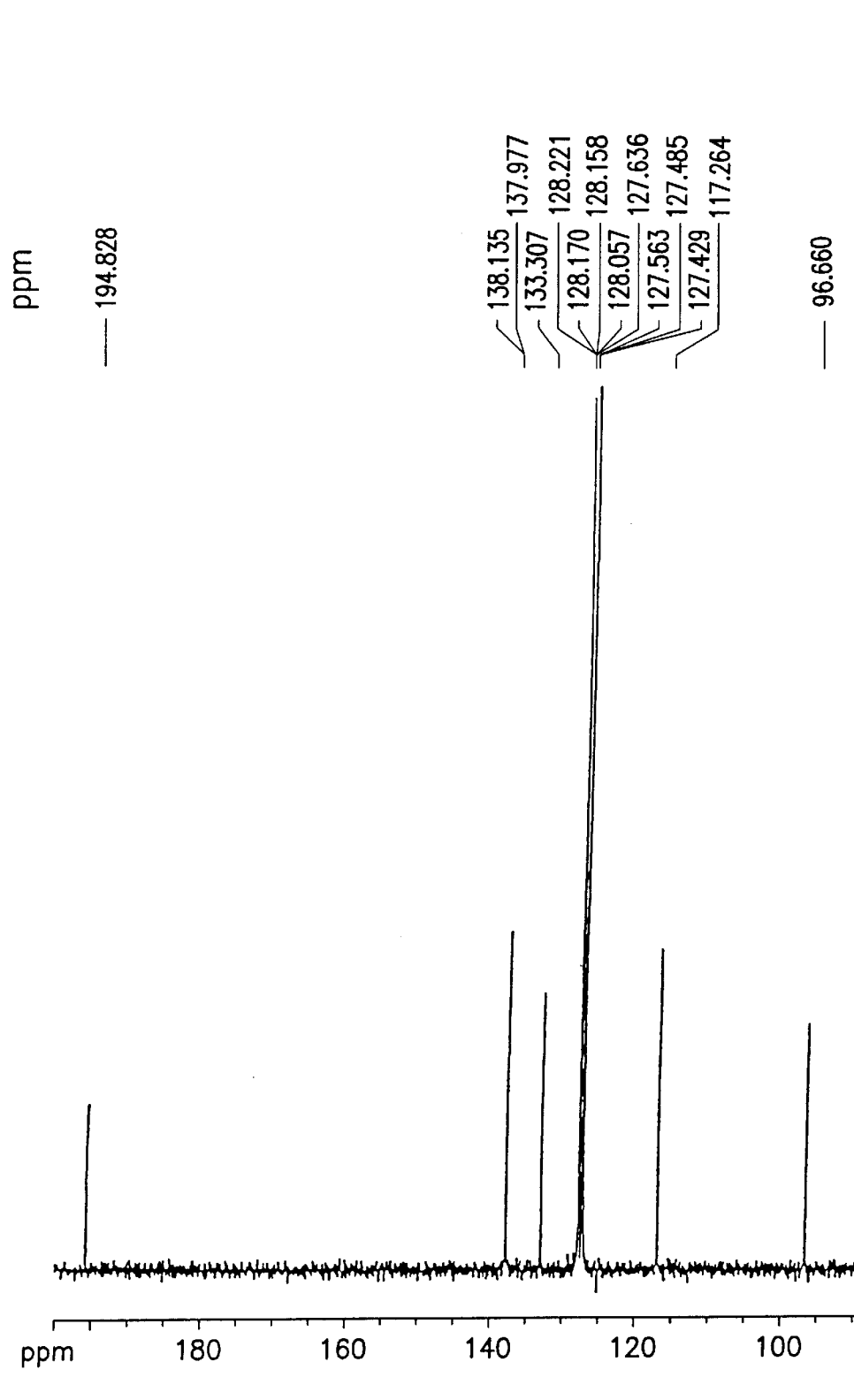
FIGS. 12A and 12B comprise a ¹³C NMR chart of 2,3,4-tri-O-benzyl-6-deoxy-1-O-(2-propenyl)-6-acetylthio-α-D-mannose, which was produced in Example 6, which is described hereinbelow.
Figure 12B:
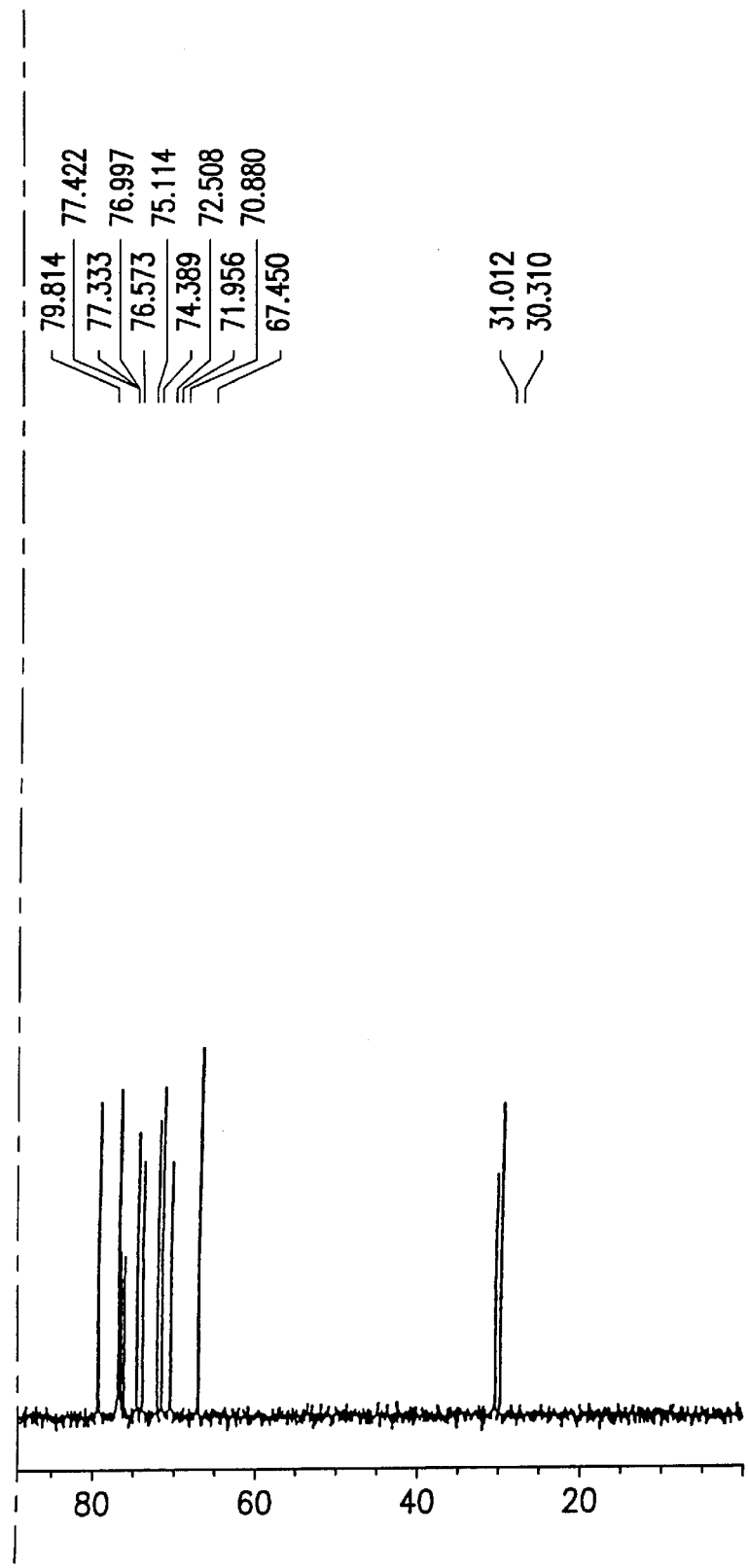

FIGS. 11A and 11B comprise a chart of $^1$H NMR (300 MHz, CDCl$_3$) in which tetramethylsilane was used as an internal standard substance, while FIGS. 12A and 12B comprise a chart of $^{13}$C NMR (300 MHz, CDCl$_3$) of the compound obtained.

Example 7

Synthesis (1) of a sulfoquinovosylacylglycerol derivative

From 2,3,4-tri-O-benzyl-1-O-(2-propenyl)-6-deoxy-6-acetylthio-α-D-glucose (VII) obtained in Example 4, a sulfoquinovosylacylglycerol derivative was synthesized through the steps g–j.

7-1) Step g: Synthesis of 3-O-(2,3,4-tri-O-benzyl-6-deoxy-6-acetylthio-α-D-glucopyranosyl)-glycerol (VIII)

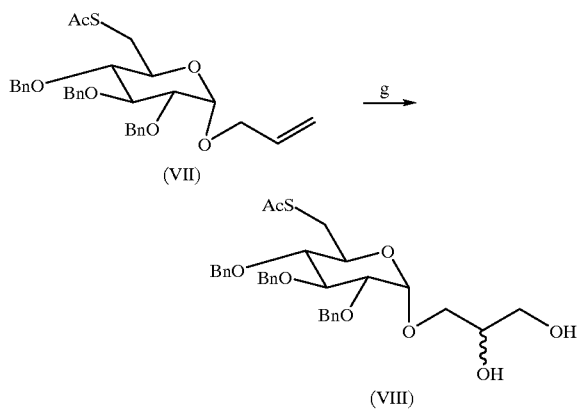

In a mixture of t-butanol and H$_2$O (=4:1), 8.30 g (15.1 mmol) of 2,3,4-tri-O-benzyl-6-deoxy-1-O-(2-propenyl)-6-acetylthio-α-D-glucose (VII) were dissolved and then 2.5 g (22.5 mmol) of trimethylamine N-oxide dihydrate and 20 mL (0.04 M) of a t-butanol solution of osmium tetraoxide were added. The solution was reacted at room temperature for 30 hours while stirring. Thereafter, 15 g of activated carbon were added, and then the reaction mixture was allowed to stand while stirring for 1.5 hours to adsorb the osmium tetraoxide on the activated carbon. After filtration with suction, the reaction was quenched by adding 250 mL of cold distilled water, and the reaction mixture was extracted with ethyl acetate (200 ml×3 times). The organic layers were combined, washed with saturated aqueous sodium chloride (300 mL×2 times), dried over anhydrous sodium sulfate, filtered, concentrated in vacuo, and purified by silica gel flash chromatography (hexane:ethyl acetate= 1:1) to give 5.00 g (8.59 mmol) of the title compound with yield of 56.9%.

7-2) Step h: Synthesis of 3-O-(2,3,4-tri-O-benzyl-6-deoxy-6-acetylthio-α-D-glucopyranosyl)-1,2-di-O-palmitoylglycerol (IX-1) and 3-O-(2,3,4-tri-O-benzyl-6-deoxy-6-acetylthio-α-D-glucopyranosyl)-1-O-palmitoylglycerol (IX-2)

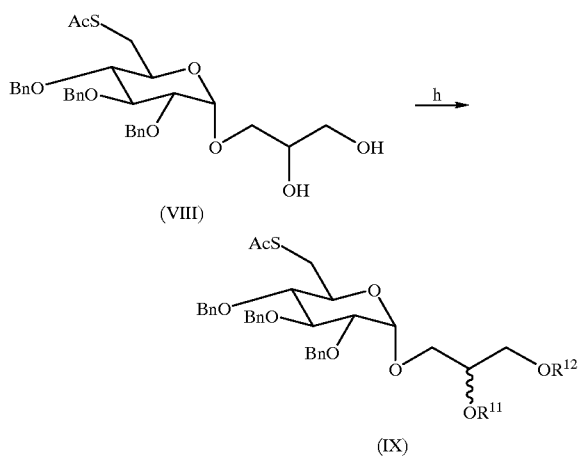

where IX-1: R$_{11}$=R$_{12}$=palmitate; IX-2: R$_{11}$=H, R$_{12}$=palmitate.

Into 5 mL of dichloromethane, 20.3 mg (34.3 μmol) of 3-O-(2,3,4-tri-O-benzyl-6-deoxy-6-acetylthio-α-D-glucopyranosyl)-glycerol (VIII) were dissolved and then 19.4 g (101 μmol) of EDCl, 5.70 mg (46.7 μmol) of DMAP, and 14.1 g (54.9 μmol) of palmitic acid were added. The solution was reacted at room temperature for 16 hours while stirring. Thereafter, the reaction was quenched by adding 20 mL of dichloromethane, and the reaction mixture was washed with saturated aqueous sodium chloride (20 mL×2 times), dried over anhydrous sodium sulfate, filtered, concentrated in vacuo, and applied to silica gel flash chromatography (hexane:ethyl acetate=7:1→3:1) to separate and purify the diester and monoester. The diester was obtained in 14.7 mg (13.9 μmol), while the monoester was obtained in 9.10 mg (11.1 μmol), with yield (total of both the esters) of 72.9%.

7-3-1) Step i-1: Synthesis of a sodium salt of 3-O-(2,3,4-tri-O-benzyl-6-deoxy-6-sulfo-α-D-glucopyranosyl)-1,2-di-O-palmitoylglycerol (X-1)

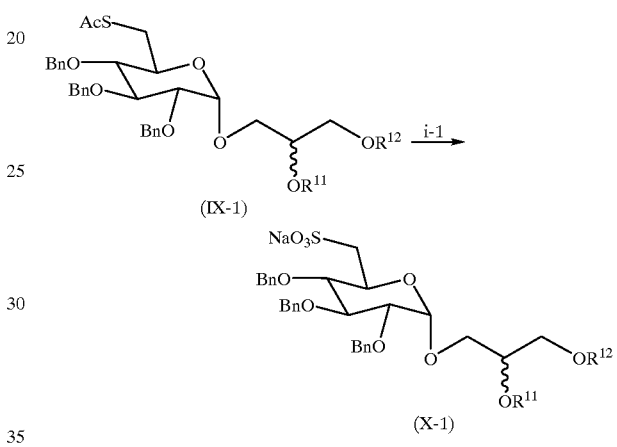

where R$_{11}$=R$_{12}$=palmitate.

Into 7 mL of glacial acetic acid, 133 mg (125 μmol) of 3-O-(2,3,4-tri-O-benzyl-6-deoxy-6-acetylthio-α-D-glucopyranosyl)-1,2-di-O-palmitoylglycerol (IX-1) were dissolved and then 814 mg of potassium acetate and 228 mg of OXONE were added. The solution was reacted for 16 hours at room temperature while stirring. Thereafter, the reaction was quenched by adding 20 mL of cold distilled water, and the reaction mixture was extracted with ethyl acetate (20 mL×5 times). The organic layers were combined, neutralized with saturated sodium hydrogencarbonate (70 mL×5 times), washed with saturated aqueous sodium chloride (60 mL×2 times), dried over anhydrous sodium sulfate, filtered, concentrated in vacuo, and purified by silica gel flash chromatography (dichloromethane:methanol=10:1) to give 57.9 mg (13.9 μmol) of the title compound with yield of 43.4%.

7-3-2) Step i-2: Synthesis of a sodium salt of 3-O-(2,3,4-tri-O-benzyl-6-deoxy-6-sulfo-α-D-glucopyranosyl)-1-O-palmitoylglycerol (X-2)

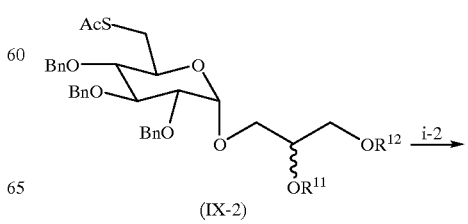

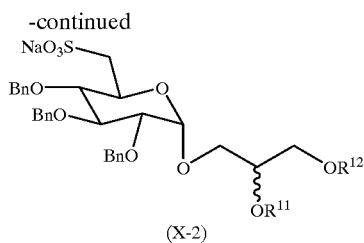

(X-2)

where $R_{11}$=H, $R_{12}$=palmitate.

Into 2 mL of glacial acetic acid, 52.1 mg (63.5 μmol) of 3-O-(2,3,4-tri-O-benzyl-6-deoxy-6-acetylthio-α-D-glucopyranosyl)-1-O-palmitoylglycerol (IX-2) were dissolved and then 102 mg of potassium acetate and 116 mg of OXONE were added. The solution was reacted at room temperature for 16 hours while stirring. Thereafter, the reaction was quenched by adding 15 mL of cold distilled water, and the reaction mixture was extracted with ethyl acetate (20 mL×5 times). The organic layers were combined, neutralized with saturated sodium hydrogen carbonate (70 mL×5 times), washed with saturated aqueous sodium chloride (60 mL×2 times), dried over anhydrous sodium sulfate, filtered, concentrated in vacuo, and purified by silica gel flash chromatography (dichloromethane:methanol=10:1) to give 35.1 mg (42.4 μmol) of the tile compound with yield of 66.8%.

7-4-1) Step j-1: Synthesis a sodium salt of 3-O-(6-deoxy-6-sulfo-α-D-glucopyranosyl)-1,2-di-O-palmitoylglycerol (XI-1)

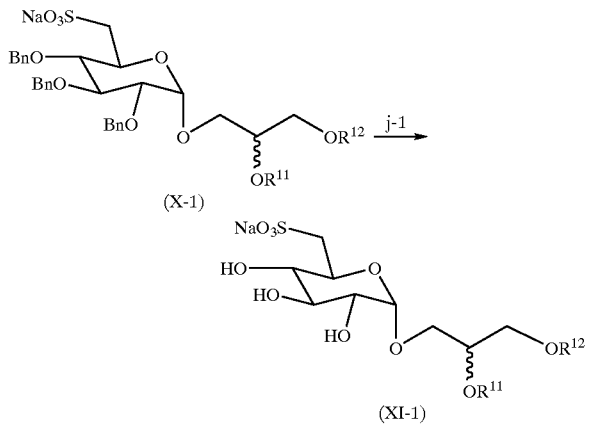

where $R_{11}$, $R_{12}$=palmitate.

Into 50 mL of ethanol, 359 mg (330 μmol) of a sodium salt of 3-O-(2,3,4-tri-O-benzyl-6-deoxy-6-sulfo-α-D-glucopyranosyl)-1,2-di-O-palmitoylglycerol(X-1) were dissolved and then 1.30 g of Pd—C were added. After substitution of the atmosphere in the flask with $H_2$, the solution mixture was reacted at room temperature for 16 hours while stirring. Then, the reaction mixture was filtered with suction, concentrated in vacuo, and purified by silica gel flash chromatography (dichloromethane:methanol=10:1→dichloromethane:methanol:water=65:25:4) to give 129 mg (168 μmol) of the title compound with yield of 50.9%.

7-4-2) Step j-2: Synthesis of a sodium salt of 3-O-(6-deoxy-6-sulfo-α-D-glucopyranosyl)-1-O-palmitoylglycerol (XI-2)

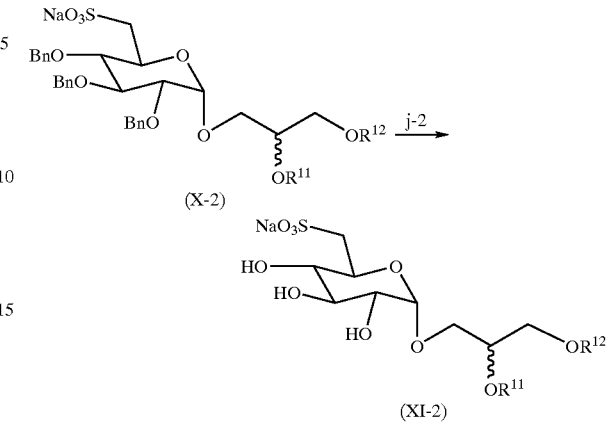

where $R_{11}$=H, $R_{12}$=palmitate.

Into 25 mL of ethanol, 202 mg (238 μmol) of a sodium salt of 3-O-(2,3,4-tri-O-benzyl-6-deoxy-6-sulfo-α-D-glucopyranosyl)-1-O-palmitoylglycerol (X-2) were dissolved and then 1.00 g of Pd—C was added. After substitution of the atmosphere in the flask with $H_2$, the solution was reacted at room temperature for 16 hours while stirring. Thereafter, the reaction mixture was filtered with suction, concentrated in vacuo, and purified by silica gel flash chromatography (dichloromethane:methanol=10:1→dichloromethane:methanol:water=65:25:4) to give 57.2 mg (168 μmol) of the title compound with yield of 43.3%.

Example 8

Synthesis (2) of a sulfoquinovosylacylglycerol derivative

From 2,3,4-tri-O-(t-butyldimethylsilyl)-6-deoxy-1-O-(2-propenyl)-6-acetylthio-α-D-glucose (VII') obtained in Example 5, a sulfoquinovosylacylglycerol derivative was synthesized through the steps g'–j'.

8-1) Step g': Synthesis of 3-O-[2,3,4-tri-O-(t-butyldimethylsilyl)-6-deoxy-6-acetylthio-α-D-glucopyranosyl)-glycerol (VIII')

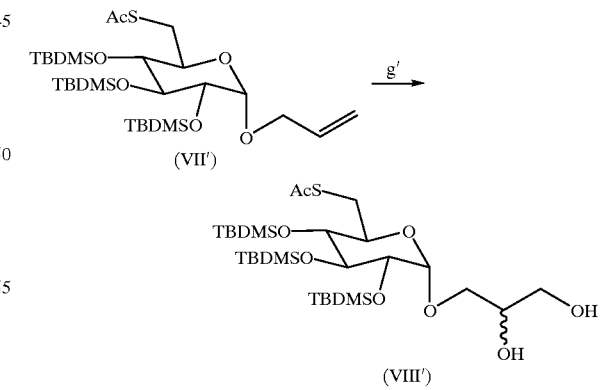

Into a mixture of t-butanol and $H_2O$ (=4:1), 5.6 g (9.02 mmol) of 2,3,4-tri-O-(t-butyldimethylsilyl)-6-deoxy-1-O-(2-propenyl)-6-acetylthio-α-D-glucose (VII') were dissolved and then 1.5 g of trimethylamine N-oxide dihydrate and 15 mL (0.04 M) of a t-butanol solution of osmium tetraoxide were added. The solution was reacted at room temperature for 22 hours while stirring. Thereafter, 15 g of activated carbon were added, and the reaction mixture was allowed to stand while stirring for 1.5 hours to adsorb the osmium tetraoxide on the activated carbon. After filtration with suction, the reaction was quenched by adding 200 mL of cold distilled water, and the reaction mixture was extracted with ethyl acetate (200 ml×3 times). The organic layers were combined, washed with saturated aqueous sodium chloride (300 mL×2 times), dried over anhydrous sodium sulfate, filtered, concentrated in vacuo, and purified by silica gel flash chromatography (hexane:ethyl acetate= 3:1→2:1) to give 5.2 g (7.94 mmol) of the title compound with yield of 88.0%.

8-2) Step h': Synthesis of 3-O-[2,3,4-tri-O-(t-butyldimethylsilyl)-6-deoxy-6-acetylthio-α-D-glucopyranosyl]-1,2-di-O-oleoyl-glycerol (IX'-1) and 3-O-[2,3,4-tri-O-(t-butyldimethylsilyl)-6-deoxy-6-acetylthio-α-D-glucopyranosyl]-1-O-oleoyl-glycerol (IX'-2)

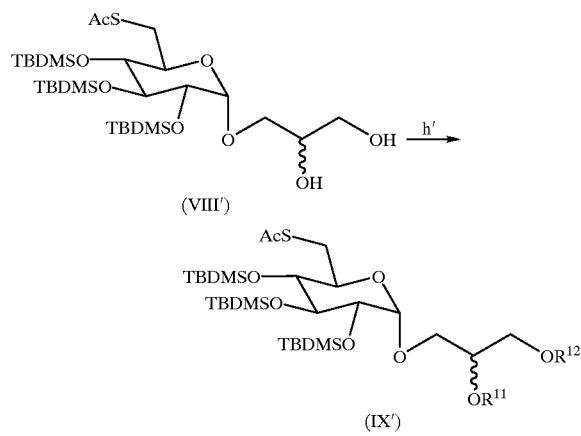

where IX'-1: $R_{11}$=$R_{12}$=oleoate; IX'-2: $R_{11}$=H, $R_{12}$=oleoate.

Into 20 mL of anhydrous dichloromethane, 1.37 g (2.09 mmol) of 3-O-[2,3,4-tri-O-(t-butyldimethylsilyl)-6-deoxy-6-acetylthio-α-D-glucopyranosyl)-glycerol (VIII') were dissolved and then 1.46 g of EDCl, 538 mg of DMAP, and 660 mg of oleic acid were added. The solution was reacted at room temperature for 16 hours while stirring. Thereafter, the reaction was quenched by adding 200 mL of dichloromethane, and the reaction mixture was washed with saturated aqueous sodium chloride (100 mL×2 times), dried over anhydrous sodium sulfate, filtered, concentrated in vacuo, and purified by silica gel flash chromatography (hexane:ethyl acetate=20:1→10:1→7:1) to give 772 mg (652 μmol) of the diester and 895 mg (974 μmol) of the monoester, with yield (total of both the esters) of 78.0%.

8-3-1) Step i'-1: Synthesis of a sodium salt of 3-O-[2,3,4-tri-O-(t-butyldimethylsilyl)-6-deoxy-6-sulfo-α-D-glucopyranosyl]-1,2-di-O-oleoyl-glycerol (X'-1)

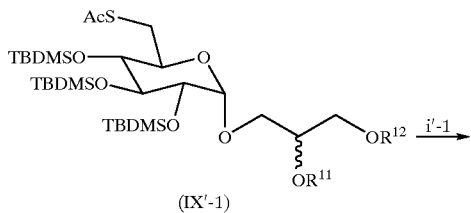

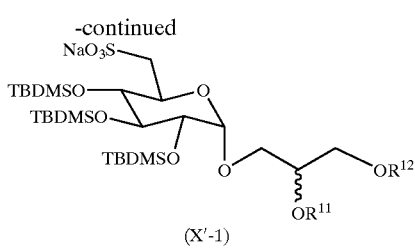

where $R_{11}$=$R_{12}$=oleoate.

Into 28 mL of glacial acetic acid, 566 mg (478 μmol) of 3-O-[2,3,4-tri-O-(t-butyldimethylsilyl)-6-deoxy-6-acetylthio-α-D-glucopyranosyl]-1,2-di-O-oleoyl-glycerol (IX'-1) were dissolved and then 3.2 g of potassium acetate and 980 mg of OXONE were added. The solution was reacted at room temperature for 6 hours while stirring. Thereafter, the reaction was quenched by adding 15 mL of cold distilled water, and the reaction mixture was extracted with ethyl acetate (20 mL×5 times). The organic layers were combined, neutralized with saturated sodium hydrogencarbonate (70 mL×5 times), washed with saturated aqueous sodium chloride (60 mL×2 times), dried over anhydrous sodium sulfate, filtered, concentrated in vacuo, and purified by silica gel flash chromatography (dichloromethane:methanol=50:1→10:1) to give 152 mg (126 μmol) of the title compound with yield of 26.4%.

8-3-2) Step i'-2: Synthesis of a sodium salt of 3-O-[2,3,4-tri-O-(t-butyldimethylsilyl)-6-deoxy-6-sulfo-α-D-glucopyranosyl]-1-O-oleoyl-glycerol (X'-2)

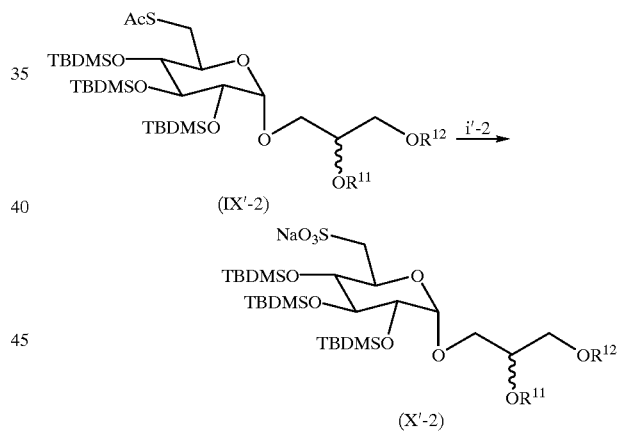

where $R_{11}$=H, $R_{12}$=oleoate.

Into 3.5 mL of glacial acetic acid, 21.4 mg (23.2 μmol) of 3-O-[2,3,4-tri-O-(t-butyldimethylsilyl)-6-deoxy-6-acetylthio-α-D-glucopyranosyl]-1-O-oleoyl-glycerol (IX'-2) were dissolved and then 500 mg of potassium acetate and 35.4 mg of OXONE were added. The solution was reacted at room temperature for 6 hours while stirring. Thereafter, the reaction was quenched by adding 15 mL of cold distilled water, and the reaction mixture was extracted with ethyl acetate (20 mL×5 times). The organic layers were combined, neutralized with saturated sodium hydrogen carbonate (70 mL×5 times), washed with saturated aqueous sodium chloride (60 mL×2 times), dried over anhydrous sodium sulfate, filtered, concentrated in vacuo, and purified by silica gel flash chromatography (dichloromethane:methanol= 50:1→20:1) to give 7.70 mg (8.13 μmol) of the title compound with yield of 34.9%.

8-4-1) Step j'-1: Synthesis of a sodium salt of 3-O-(6-deoxy-6-sulfo-α-D-glucopyranosyl)-1,2-di-O-oleoyl-glycerol (XI'-1)

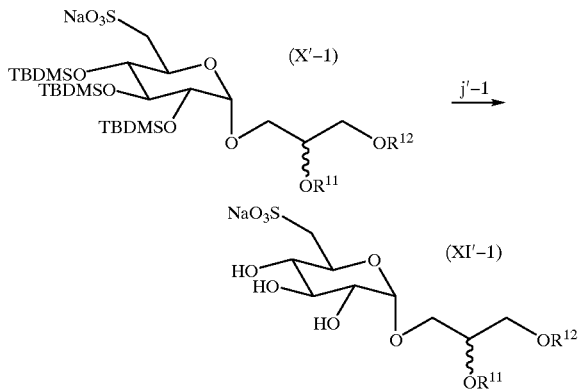

where $R_{11}$, $R_{12}$=oleoate.

Into 5 mL of a mixture of acetic acid, tetrahydrofuran, trifluoroacetic acid and water (3:1:0.4:1), 214 mg (176 μmol) of a sodium salt (X'-1) of 3-O-[2,3,4-tri-O-(t-butyldimethylsilyl)-6-deoxy-6-sulfo-α-D-glucopyranosyl]-1,2-di-O-oleoyl-glycerol were dissolved. The solution was reacted at room temperature for 16 hours while stirring, and the reaction mixture was extracted with ethyl acetate (10 mL×3 times). The organic layers were combined, washed with saturated sodium chloride solution (20 mL×2 times), dried over anhydrous sodium sulfate, filtered, concentrated in vacuo, and purified by silica gel flash chromatography (dichloromethane:methanol=10:1→dichloromethane:methanol:water=65:25:4) to give 84.1 mg (99.1 μmol) of the title compound with yield of 56.3%.

8-4-2) Step j'-2: Synthesis of a sodium salt of 3-O-(6-deoxy-6-sulfo-α-D-glucopyranosyl)-1-O-oleoyl-glycerol (XI'-2)

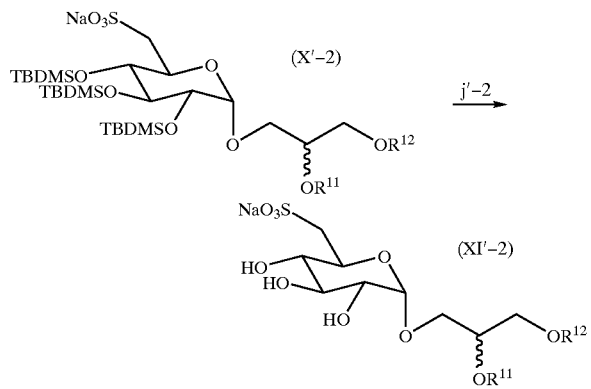

where $R_{11}$=H, $R_{12}$=oleoate.

Into 7 mL of a mixture of acetic acid, tetrahydrofuran, trifluoroacetic acid and water (3:1:0.4:1), 358 mg (378 μmol) of a sodium salt of 3-O-[2,3,4-tri-O-(t-butyldimethylsilyl)-6-deoxy-6-sulfo-α-D-glucopyranosyl]-1-O-oleoyl-glycerol (X'-2) were dissolved. The solution was reacted at room temperature for 16 hours while stirring, and the reaction mixture was extracted with ethyl acetate (10 mL×3 times). The organic layers were combined, washed with saturated sodium chloride solution (20 mL×2 times), dried over anhydrous sodium sulfate, filtered, concentrated in vacuo, and purified by silica gel flash chromatography (dichloromethane:methanol=10:1→dichloromethane:methanol:water=65:25:4) to give 138 mg (237 μmol) of the title compound with yield of 62.7%.

Example 9

Synthesis of a compound represented by Formula (2)

A sodium salt of 3-O-(6-deoxy-6-sulfo-β-D-glucopyranosyl)-1-O-palmitoylglycerol was synthesized as follows.

Using 2,3,4-tri-O-benzyl-1-O-(2-propenyl)-6-O-(4-tolylsulfonyl)-β-D-glucose, which has been isolated after the step d in Example 11, the same manners as in the step f in Example 4, as well as the steps g, h, i-2 and j-2 in Example 7 were carried out to yield 1.52 mg (3.10 μmol) of the title compound as a white crystal, with yield of 22.5%.

Melting point: 80–82° C.; $[\alpha]_D$=+0.4° (CHCl$_3$).

Figure 13A:
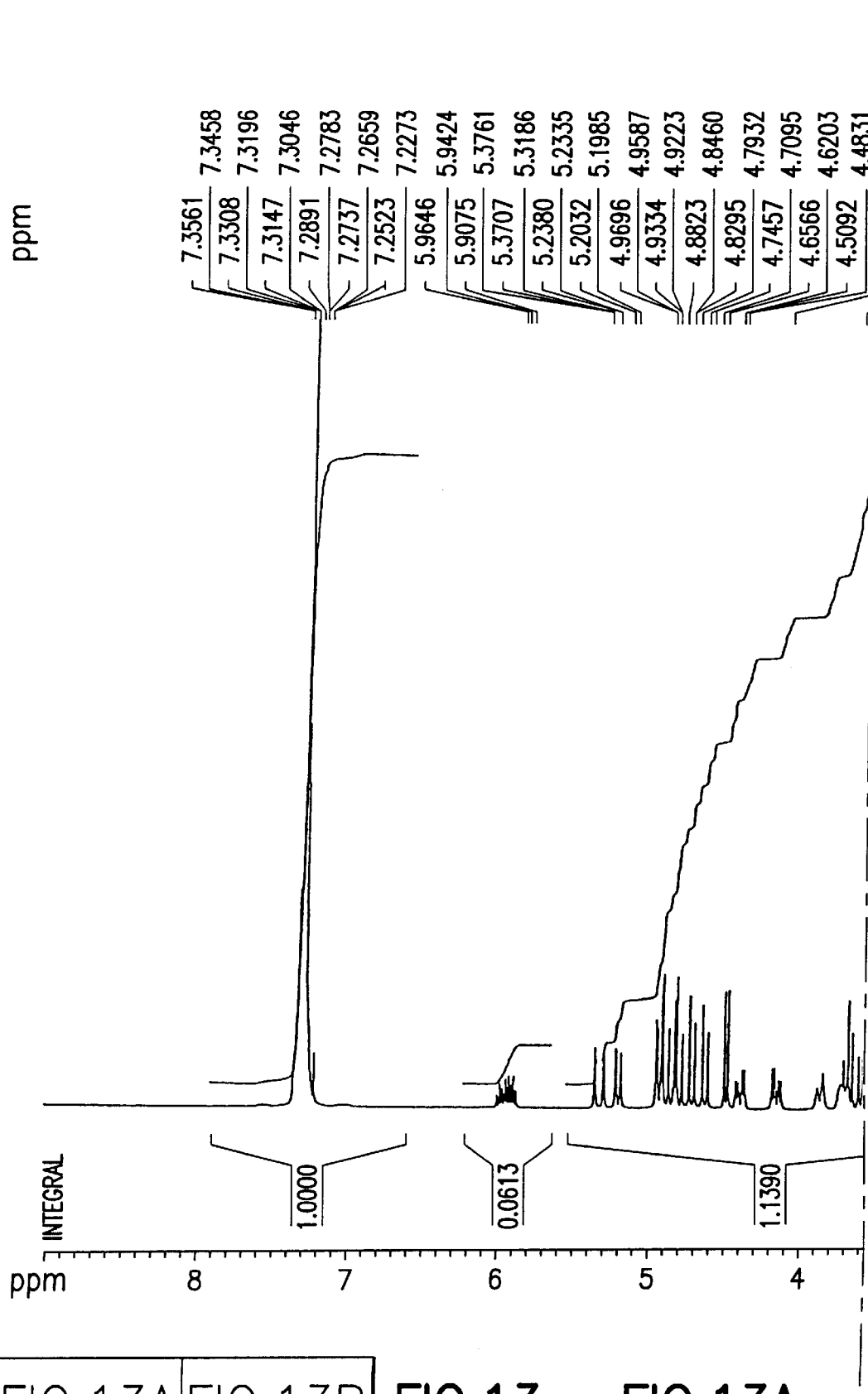
FIGS. 13A and 13B comprise a ¹H NMR chart of a sodium salt of 3-O-(6-deoxy-6-sulfo-β-D-glucopyranosyl)-1-O-palmitoylglycerol, which was produced in Example 9, which is described hereinbelow.
Figure 13B:
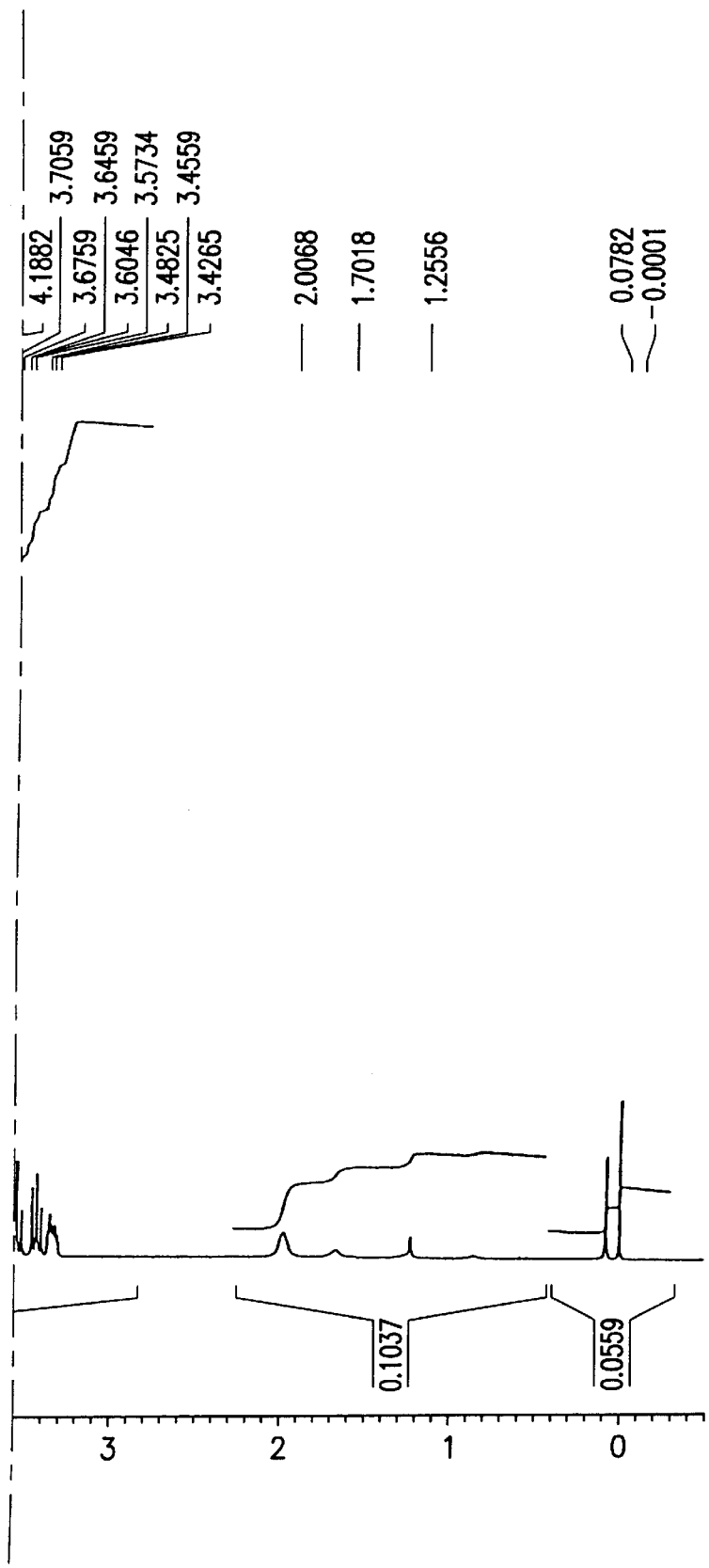
Figure 14A:
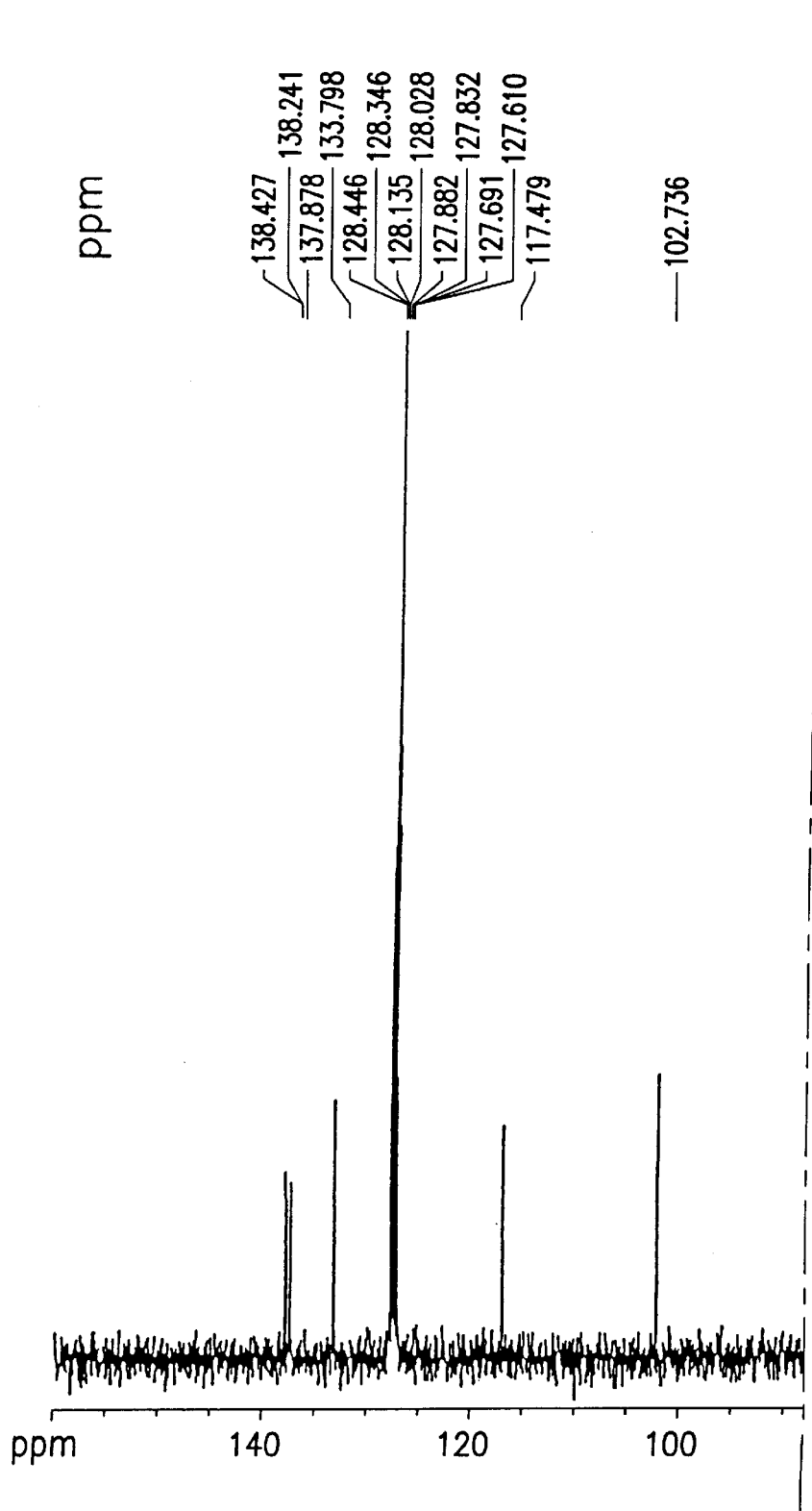
FIGS. 14A and 14B comprise a ¹³C NMR chart of a sodium salt of 3-O-(6-deoxy-6-sulfo-β-D-glucopyranosyl)-1-O-palmitoylglycerol, which was produced in Example 9, which is described hereinbelow.
Figure 14B:
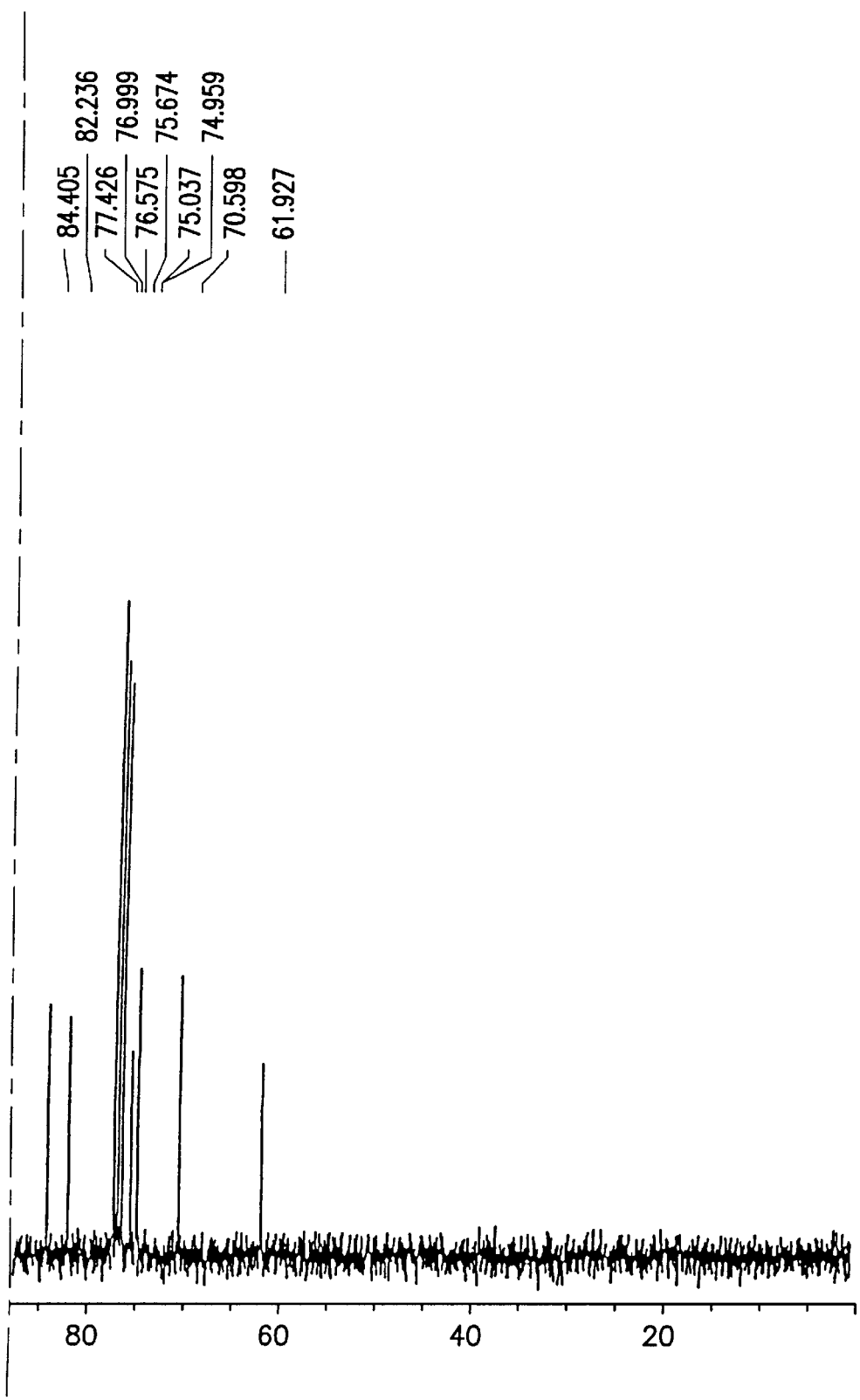

FIGS. 13A and 13B comprise a chart of $^1$H NMR (300 MHz, CDCl$_3$) in which tetramethylsilane was used as an internal standard substance, while FIGS. 14A and 14B comprise a chart of $^{13}$C NMR (300 MHz, CDCl$_3$) of the compound obtained.

As described above, the sulfoquinovosylacylglycerol derivatives represented by Formula (1) of the invention have a significant anticancer effect. The anticancer drug of the present invention comprising, as an effective ingredient, at least one compound selected from the group consisting of such sulfoquinovosylacylglycerol derivatives and pharmaceutically acceptable salts thereof are greatly expected as a medicinal drug.

The present invention also provides novel sulfoquinovosylacylglycerol β-derivatives.

The sulfoquinovosylacylglycerol derivatives represented by Formula (1) which are used as effective ingredients in the anticancer drug of the present invention have an inhibitory effect against DNA polymerase α (see the Assay 1). It is known that there are DNA polymerases β, γ, δ and ε, in addition to the DNA polymerase α. Among these DNA polymerases, the δ and ε are biochemical analogues to the α. The biochemical analogues mean that they are common in enzymatic functions as follows. (i) Existence or nonexistence of sensitivity to a specific compound: For example, these three types of DNA polymerases have sensitivity to N-ethylmaleimide and butylphenyl-dGTP, but do not have sensitivity to dideoxy TTP (ddTTP). (ii) Fidelity: They have high accuracy in DNA synthesis with respect to a template DNA. (iii) Reaction site: These three types of DNA polymerases are directly involved in DNA replication which is cooperated with cell division.

The DNA polymerase α (including δ and ε as biochemical analogues) is generally considered to control DNA synthesis correspondingly to the cell cycle. The inventors consider that the compounds represented by Formula (1) according to the present invention have inhibitory activity against not only the DNA polymerase a but also the DNA polymerases δ and ε.

The pyranosides of Formula (A) of the present invention, and the pyranosides of Formula (B) of the present invention, which can be produced from the pyranosides of Formula (A), are compounds useful as intimidates for producing sulfopyranosylacylglycerol derivatives. In other words, the pyranosides represented by Formulae (A) and (B) of the present invention can be used as intermediates for industrially producing sulfopyranosylacylglycerol derivatives in high yields and large quantities at low costs.

The following is the reason why the pyranosides represented by Formulae (A) and (B) of the invention can be used as intermediates for producing sulfopyranosylacylglycerol derivatives to make the steps for producing them fewer than conventional methods.

As already described earlier, in conventional methods for synthesizing glyceroglycolipids it is necessary to protect and de-protect the hydroxyl group bonded to the C-1 of the sugar before introducing a target glycerol derivative. Specifically, in the conventional methods, all hydroxyl groups of the sugar are first acetylated, and then the C-1 is halogenated. Thereafter, a glycerol derivative is introduced to the C-1, and then the group first acetylated is deacetylated. The hydroxyl groups of the sugar are then protected again. Next, the protecting group of the glycerol derivative is eliminated, and a fatty acid is introduced to the glycerol. Finally, the protecting groups of the sugar are eliminated. On the other hand, the pyranoside of Formula (A) according to the present invention can be obtained by reaction in the step A, that is, reaction for 2-propenylation of the hydroxyl group bonded to the C-1 of the sugar to protect the C-1. By using the 2-propenylated sugar as an intermediate of glyceroglycolipid, the skeleton comprising three carbons of the 2-propenyl group introduced as a protecting group can be, as it is, used as a glycerol skeleton. Thus, in fewer steps glyceroglycolipid can be synthesized.

Although the protection of hydroxyl groups by 2-propenylation is known per se, the reaction is novel that in the process for producing sulfolipid, in particular glyceroglycolipid, the C-1 of the sugar is 2-propenylated and then the resultant skeleton, as it is, is used as a glycerol skeleton.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method for treating colon cancer or gastric cancer comprising administering to a patient in need thereof and suffering from colon cancer or gastric cancer, a pharmaceutically effective amount of at least one sulfoquinovosylacylglycerol compound represented by formula (1):

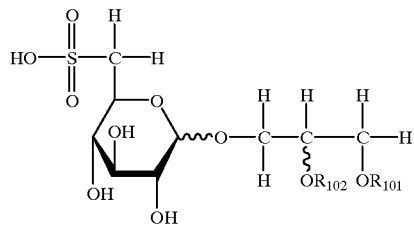

(1)

wherein the bond between the D-glucosyl moiety and the glyceridyl moiety is in the α-configuration, $R_{101}$ is represented by $CH_3(CH_2)_nCO—$, wherein n is an integer of 12 to 24, and $R_{102}$ is a hydrogen atom or $CH_3(CH_2)_nCO—$,
wherein n is an integer of 12 to 24, or a pharmaceutically acceptable salt thereof, alone or in combination with a pharmaceutically acceptable carrier.

2. The method according to claim 1, wherein each n is an even number of 12 to 24.

3. The method according to claim 1, wherein $R_{102}$ is a hydrogen atom.

4. The method according to claim 1, wherein $R_{101}$ is $CH_3(CH_2)_{12}CO—$ and $R_{102}$ is $CH_3(CH_2)_{12}CO—$.

5. The method according to claim 1, which consists in administering to said patient one sulfoquinovosylacylglycerol compound of formula (1) or said pharmaceutically acceptable salt thereof, alone or in combination with a pharmaceutically acceptable carrier.

6. The method according to claim 5, wherein $R_{101}$ is $CH_3(CH_2)_{12}CO—$ and $R_{102}$ is $CH_3(CH_2)_{12}CO—$.

7. The method according to claim 5, wherein $R_{101}$ is $CH_3(CH_2)_{12}CO—$ and $R_{102}$ is a hydrogen atom.

8. The method according to claim 5, wherein $R_{101}$ is $CH_3(CH_2)_{14}CO—$ and $R_{102}$ is a hydrogen atom.

9. The method according to claim 5, wherein $R_{101}$ is $CH_3(CH_2)_{16}CO—$ and $R_{102}$ is a hydrogen atom.

10. The method according to claim 5, wherein $R_{101}$ is $CH_3(CH_2)_{18}CO—$ and $R_{102}$ is a hydrogen atom.

11. The method according to claim 5, wherein $R_{101}$ is $CH_3(CH_2)_{20}CO—$ and $R_{102}$ is a hydrogen atom.

12. The method according to claim 5, wherein $R_{101}$ is $CH_3(CH_2)_{22}CO—$ and $R_{102}$ is a hydrogen atom.

13. The method according to claim 5, wherein $R_{101}$ is $CH_3(CH_2)_{24}CO—$ and $R_{102}$ is a hydrogen atom.

* * * * *